(12) United States Patent
Yan et al.

(10) Patent No.: US 12,285,473 B2
(45) Date of Patent: Apr. 29, 2025

(54) CANCER VACCINES TARGETING MUC16 AND USES THEREOF

(71) Applicant: Inovio Pharmaceuticals, Inc., Plymouth Meeting, PA (US)

(72) Inventors: Jian Yan, Wallingford, PA (US); Anna Slager, Lansdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 528 days.

(21) Appl. No.: 17/559,824

(22) Filed: Dec. 22, 2021

(65) Prior Publication Data

US 2022/0111026 A1 Apr. 14, 2022

Related U.S. Application Data

(62) Division of application No. 16/219,460, filed on Dec. 13, 2018, now Pat. No. 11,235,044.

(60) Provisional application No. 62/598,314, filed on Dec. 13, 2017.

(51) Int. Cl.
| | | |
|---|---|---|
| *C12N 15/00* | (2006.01) | |
| *A61K 39/00* | (2006.01) | |
| *C07K 14/47* | (2006.01) | |
| *C12N 15/86* | (2006.01) | |

(52) U.S. Cl.
CPC .... *A61K 39/00117* (2018.08); *C07K 14/4727* (2013.01); *C07K 14/4748* (2013.01); *A61K 2039/53* (2013.01); *A61K 2039/54* (2013.01); *A61K 2039/572* (2013.01)

(58) Field of Classification Search
CPC .......... A61K 39/00117; A61K 2039/53; A61K 2039/54; A61K 2039/572; C07K 14/4727; C07K 14/4748; C12N 15/00; C12N 15/86
USPC ...................................................... 424/85.2
See application file for complete search history.

(56) References Cited

U.S. PATENT DOCUMENTS

| | | | |
|---|---|---|---|
| 4,510,245 A | 4/1985 | Cousens et al. | |
| 4,554,101 A | 11/1985 | Hopp | |
| 4,722,848 A | 2/1988 | Paoletti et al. | |
| 4,790,987 A | 12/1988 | Compans et al. | |
| 4,797,368 A | 1/1989 | Carter et al. | |
| 4,920,209 A | 4/1990 | Davis et al. | |
| 4,945,050 A | 7/1990 | Sanford et al. | |
| 5,017,487 A | 5/1991 | Stunnenberg et al. | |
| 5,036,006 A | 7/1991 | Sanford et al. | |
| 5,077,044 A | 12/1991 | Stocker | |
| 5,110,587 A | 5/1992 | Paoletti et al. | |
| 5,112,749 A | 5/1992 | Brey et al. | |
| 5,174,993 A | 12/1992 | Paoletti | |
| 5,223,424 A | 6/1993 | Cochran et al. | |
| 5,225,336 A | 7/1993 | Paoletti | |
| 5,240,703 A | 8/1993 | Cochran | |
| 5,242,829 A | 9/1993 | Panicali et al. | |
| 5,273,525 A | 12/1993 | Hofmann | |
| 5,294,441 A | 3/1994 | Curtiss, III | |
| 5,294,548 A | 3/1994 | Mclinden et al. | |
| 5,310,668 A | 5/1994 | Ellis et al. | |
| 5,387,744 A | 2/1995 | Curtiss et al. | |
| 5,389,368 A | 2/1995 | Curtiss, III | |
| 5,424,065 A | 6/1995 | Curtiss et al. | |
| 5,451,499 A | 9/1995 | Cochran | |
| 5,453,364 A | 9/1995 | Paoletti | |
| 5,462,734 A | 10/1995 | Letchworth et al. | |
| 5,470,734 A | 11/1995 | Sondermeijer et al. | |
| 5,474,935 A | 12/1995 | Chatterjee et al. | |
| 5,482,713 A | 1/1996 | Paoletti | |
| 5,580,859 A | 12/1996 | Felgner et al. | |
| 5,591,439 A | 1/1997 | Plotkin et al. | |
| 5,593,972 A | 1/1997 | Weiner et al. | |
| 5,643,579 A | 7/1997 | Hung et al. | |
| 5,650,309 A | 7/1997 | Wong-Staal et al. | |
| 5,676,594 A | 10/1997 | Joosten | |
| 5,698,202 A | 12/1997 | Ertl et al. | |
| 5,703,055 A | 12/1997 | Felgner et al. | |
| 5,739,118 A | 4/1998 | Carrano et al. | |
| 5,817,637 A | 10/1998 | Weiner et al. | |
| 5,830,876 A | 11/1998 | Weiner et al. | |
| 5,955,088 A | 9/1999 | Ghiasi et al. | |

(Continued)

FOREIGN PATENT DOCUMENTS

| | | |
|---|---|---|
| CN | 102321923 A | 1/2012 |
| JP | 2005-514901 A | 5/2005 |

(Continued)

OTHER PUBLICATIONS

Yun Yang et al.; "Expression and purification of mucin 16 and preparation and characterization of anti-mucin 16 1 monoclonal antibody"; Chinese Journal of Cellular and Molecular Immunology; vol. 28(9); Sep. 2012; p. 960-963 (abstract only).

Andre et al., "Increased Immune Response Elicited by DNA Vaccination with a Synthetic gp120 Sequence with Optimized Codon Usage" Journal of Virology, vol. 72, No. 2, Feb. 1998, pp. 1497-1503.

(Continued)

*Primary Examiner* — Yan Xiao
(74) *Attorney, Agent, or Firm* — BakerHostetler

(57) ABSTRACT

Disclosed herein are nucleic acid molecules comprising one or more nucleic acid sequences that encode a modified consensus MUC16 antigen. Vectors, compositions, and vaccines comprising one or more nucleic acid sequences that encode a modified consensus MUC16 antigen are disclosed. Methods of treating a subject with a MUC16-expressing tumor and methods of preventing a MUC16-expressing tumor are disclosed. Modified consensus MUC16 antigen is disclosed.

16 Claims, 33 Drawing Sheets

Specification includes a Sequence Listing.

(56) References Cited

U.S. PATENT DOCUMENTS

| | | | |
|---|---|---|---|
| 5,962,428 A | 10/1999 | Carrano et al. | |
| 5,981,505 A | 11/1999 | Weiner et al. | |
| 6,034,298 A | 3/2000 | Lam et al. | |
| 6,042,836 A | 3/2000 | Berman et al. | |
| 6,110,161 A | 8/2000 | Mathiesen et al. | |
| 6,156,319 A | 12/2000 | Cohen et al. | |
| 6,261,281 B1 | 7/2001 | Mathiesen et al. | |
| 6,589,529 B1 | 7/2003 | Choi et al. | |
| 6,697,669 B2 | 2/2004 | Dev et al. | |
| 6,939,862 B2 | 9/2005 | Bureau et al. | |
| 6,958,060 B2 | 10/2005 | Mathiesen et al. | |
| 7,238,522 B2 | 7/2007 | Hebel et al. | |
| 7,245,963 B2 | 7/2007 | Draghia-Akli et al. | |
| 7,328,064 B2 | 2/2008 | Mathiesen et al. | |
| 8,008,265 B2 | 8/2011 | Weiner et al. | |
| 8,119,395 B1 | 2/2012 | Weiner et al. | |
| 9,452,285 B2 | 9/2016 | Draghia-Akli et al. | |
| 2003/0078399 A1* | 4/2003 | Lloyd ............... | C12Q 1/6886 536/23.1 |
| 2004/0175727 A1 | 9/2004 | Draghia-Akli et al. | |
| 2005/0005263 A1 | 1/2005 | Miyazaki | |
| 2005/0052630 A1 | 3/2005 | Smith et al. | |
| 2007/0015907 A1 | 1/2007 | O'Brien et al. | |
| 2009/0004716 A1 | 1/2009 | Draghia-Akli et al. | |
| 2009/0087849 A1 | 4/2009 | Malinowski et al. | |
| 2010/0331536 A1 | 12/2010 | O'Brien et al. | |
| 2012/0035529 A1 | 2/2012 | Coukos et al. | |
| 2012/0231090 A1 | 9/2012 | Bajic et al. | |

FOREIGN PATENT DOCUMENTS

| | | |
|---|---|---|
| WO | 93/24640 A2 | 12/1993 |
| WO | 94/16737 A1 | 8/1994 |
| WO | 98/17799 A1 | 4/1998 |
| WO | 99/43839 A1 | 9/1999 |
| WO | 2002/083866 A2 | 10/2002 |
| WO | 2002/092836 A2 | 11/2002 |
| WO | 2005/000235 A2 | 1/2005 |
| WO | 2005/051991 A2 | 6/2005 |
| WO | 2007/050095 A2 | 5/2007 |
| WO | 2007/087178 A2 | 8/2007 |
| WO | 2009/124309 A2 | 10/2009 |
| WO | 2011/032179 A1 | 3/2011 |
| WO | 2011/097640 A1 | 8/2011 |

OTHER PUBLICATIONS

Chekhun et al.; "Anti-tumor vaccines"; Oncology; vol. 10 No. 2; 2008; p. 204-205 (contains English Translation).

Demi et al., "Multiple Effects of Codon Usage Optimization on Expression and Immunogenicity of DNA Candidate Vaccines Encoding the Human Immunodeficiency Virus Type 1 Gag Protein" Journal of Virology, vol. 75, No. 22, Nov. 2001, pp. 10991-11001.

International Search Report and Written Opinion issued in PCT/US18/65524, dated May 14, 2019.

Kyte et al., "A Simple Method for Displaying the Hydropathic Character of a Protein" J. Mol. Biol., vol. 157, 1982, pp. 105-132.

Muthumani et al., "Novel engineered HIV-1 East African Clade-A gp160 plasmid construct induces strong humoral and cell-mediated immune responses in vivo" Virology vol. 314, 2003, pp. 134-146.

O'Brien et al., "The CA 125 Gene: An Extracellular Superstructure Dominated by Repeat Sequences" Research Article Tumor Biology, vol. 22, 2001, pp. 348-366.

Rao et al., "Expression of the Carboxy-Terminal Portion of MUC16/CA125 Induces Transformation and Tumor nvasion" Research Article PLOS ONE, May 12, 2015, 22 Pages.

Schneider, et al., "Inactivation of the Human Immunodeficiency Virus Type 1 Inhibitory Elements Allows Rev-Independent Expression of Gag and Gag/Protease and Particle Formation" Journal of Virology, vol. 71, No. 7, Jul. 1997, pp. 4892-4903.

Yang et al.," Induction of Potent Th1-Type Immune Responses from a Novel DNA Vaccine or West Nile Virus New York Isolate (WNV-NY1999)" The Journal of infectious Diseases, vol. 184, 2001, pp. 809-816.

* cited by examiner

| | | |
|---|---|---|
| synthetic consensus MUC16 CTD.pro | I A L L R D I Q D K V T T L Y K G S Q L H D T F R F C L V T N L T M D S M L V T | 40 |
| Hu MUC16 CTD (AAL65133.2).pro | I T L L R D I Q D K V T T L Y K G S Q L H D T F R F C L V T N L T M D S V L V T | 40 |
| synthetic consensus MUC16 CTD.pro | V K A L F S S N L D P S L V E Q V F L D K T L N A S S H W L G S T Y Q L V D I H | 80 |
| Hu MUC16 CTD (AAL65133.2).pro | V K A L F S S N L D P S L V E Q V F L D K T L N A S F H W L G S T Y Q L V D I H | 80 |
| synthetic consensus MUC16 CTD.pro | V T E M E P S V Y Q P T S S S S T Q H F Y L N F T I T N L P Y S Q D I A Q P G T | 120 |
| Hu MUC16 CTD (AAL65133.2).pro | V T E M E S S V Y Q P T S S S S T Q H F Y L N F T I T N L P Y S Q D K A Q P G T | 120 |
| synthetic consensus MUC16 CTD.pro | T N Y Q R N K R N I E D A L N Q L F R N S S I K S Y F S D C Q V S T F R S V P N | 160 |
| Hu MUC16 CTD (AAL65133.2).pro | T N Y Q R N K R N I E D A L N Q L F R N S S I K S Y F S D C Q V S T F R S V P N | 160 |
| synthetic consensus MUC16 CTD.pro | S H H T G V D S L C A F S P L A R R V D R V A I Y E E F L R M T R A G T Q L Q A | 200 |
| Hu MUC16 CTD (AAL65133.2).pro | R H H T G V D S L C N F S P L A R R V D R V A I Y E E F L R M T R N G T Q L Q N | 200 |
| synthetic consensus MUC16 CTD.pro | F T L D R S S V L V D G Y S P N R N E P L T G N S D L P F W A I L I C L A G L | 240 |
| Hu MUC16 CTD (AAL65133.2).pro | F T L D R S S V L V D G Y S P N R N E P L T G N S D L P F W A V I L I G L A G L | 240 |
| synthetic consensus MUC16 CTD.pro | L G L I T C L I C G F L V | 253 |
| Hu MUC16 CTD (AAL65133.2).pro | L G L I T C L I C G V L V | 253 |

Decoration 'Decoration #1': Shade (with solid light gray) residues that differ from Hu MUC16 CTD (AAL65133.2).pro.

FIG. 5

Synthetic consensus
MUC16 IRC + R59

FIG. 7

FIG. 8B
FIG. 8C
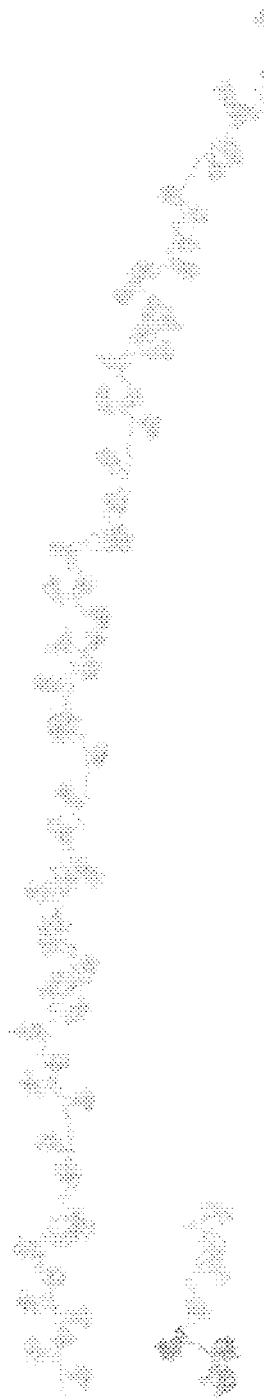
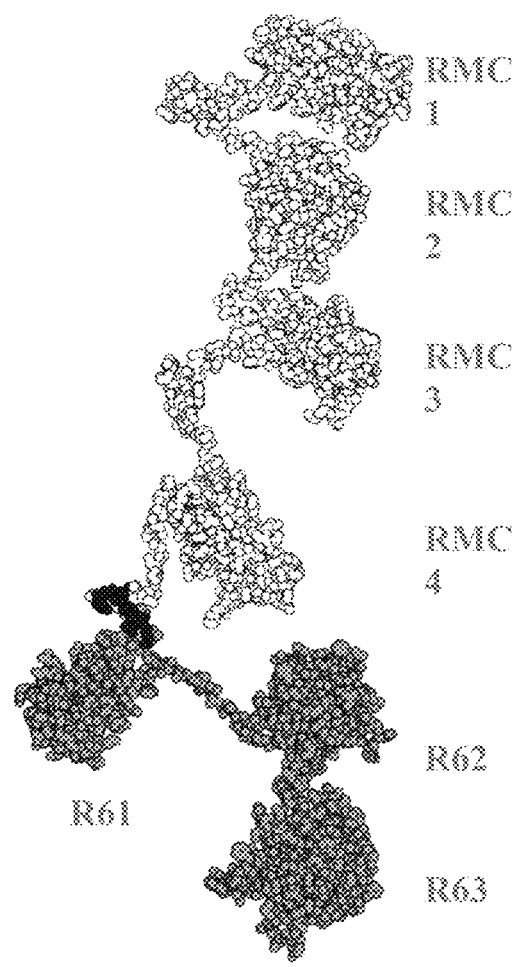

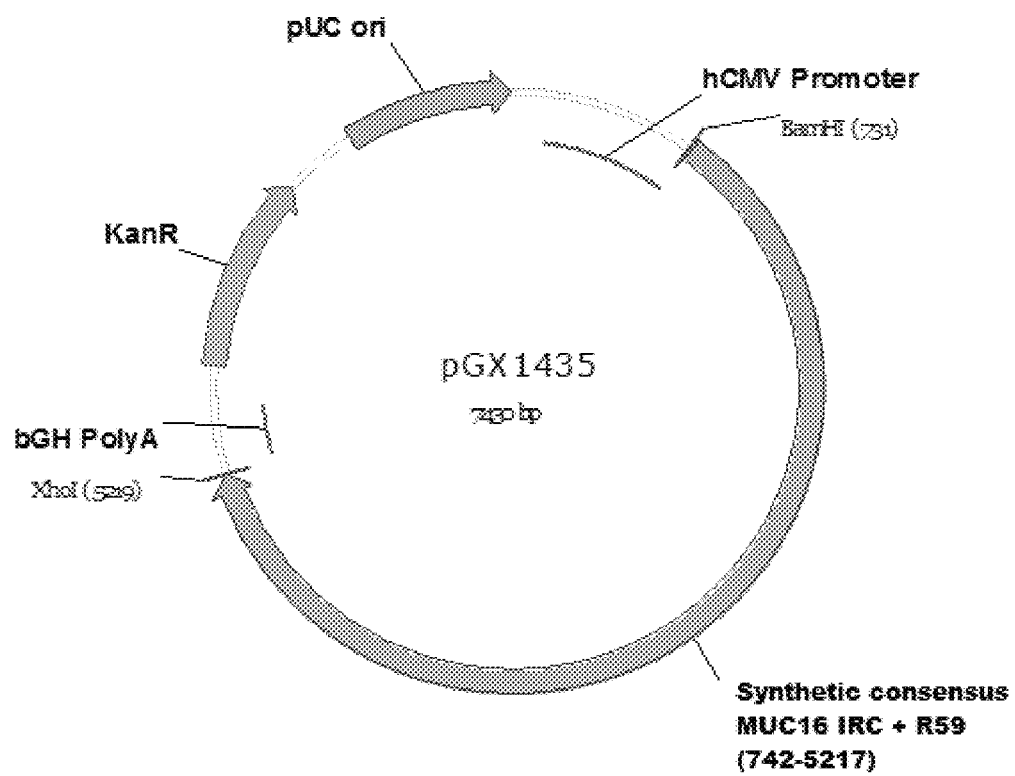
FIG. 11

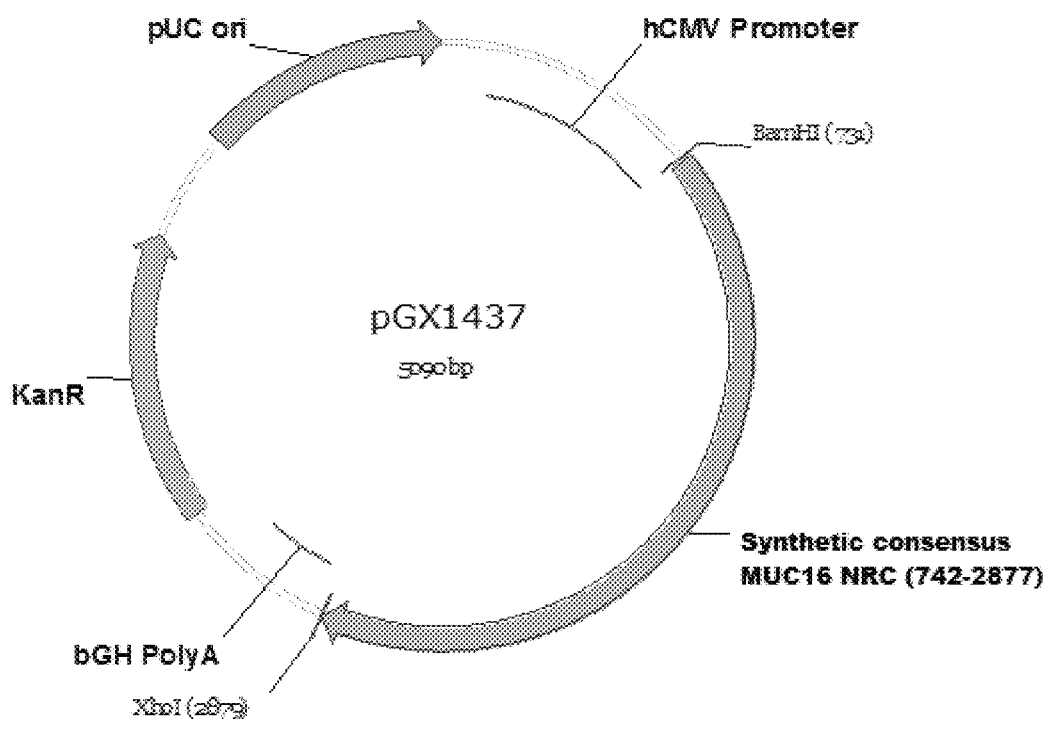
FIG. 13

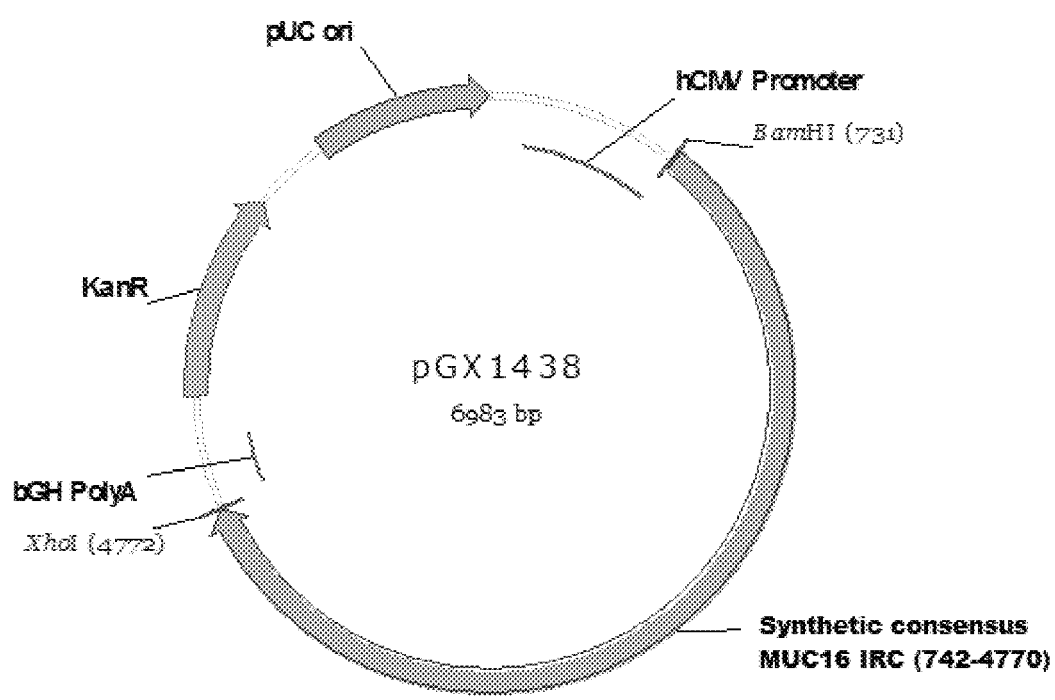
FIG. 14

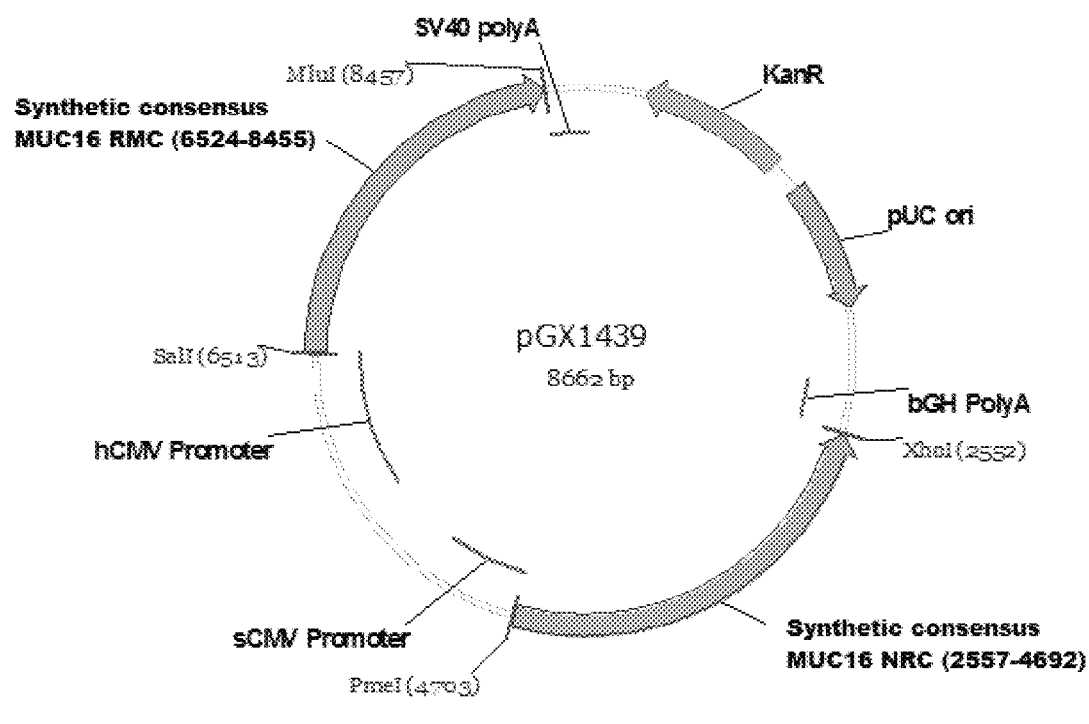
FIG. 15

FIG. 22A
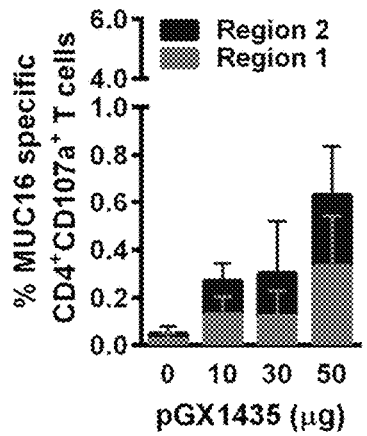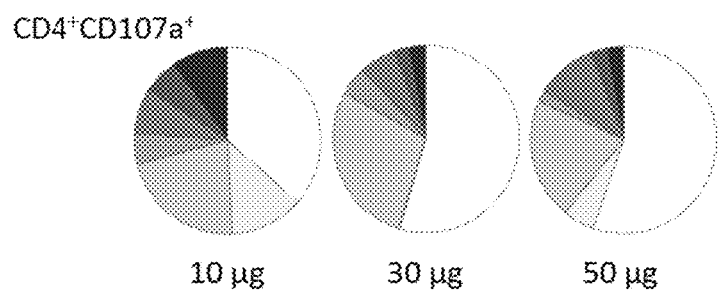
FIG. 22B
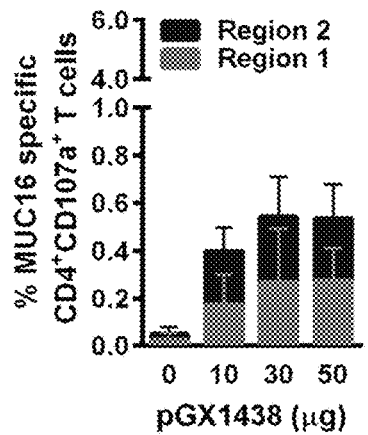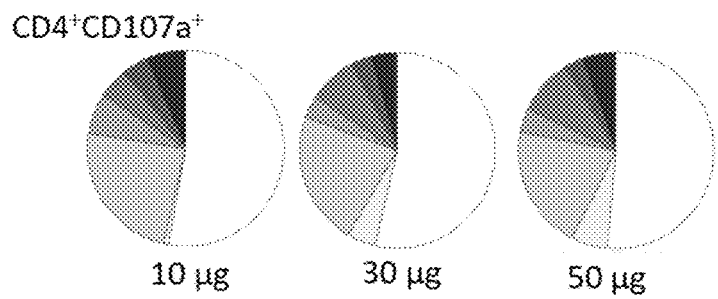
FIG. 22C
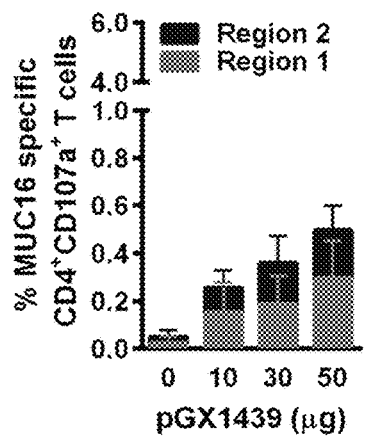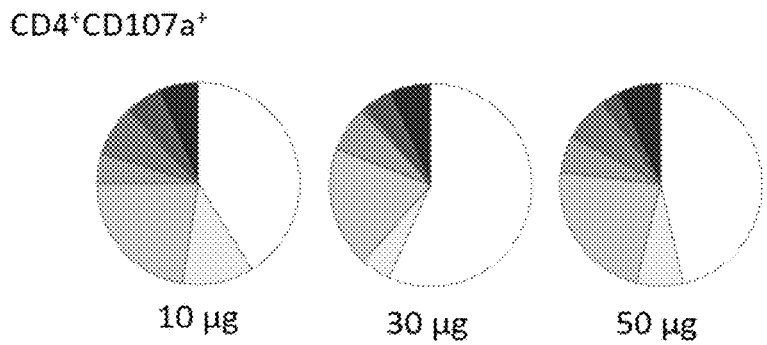

FIG. 25A
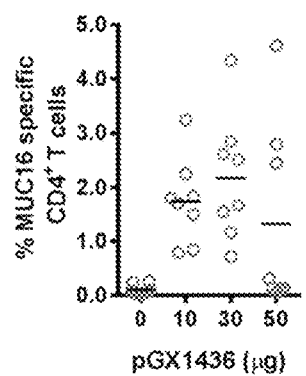
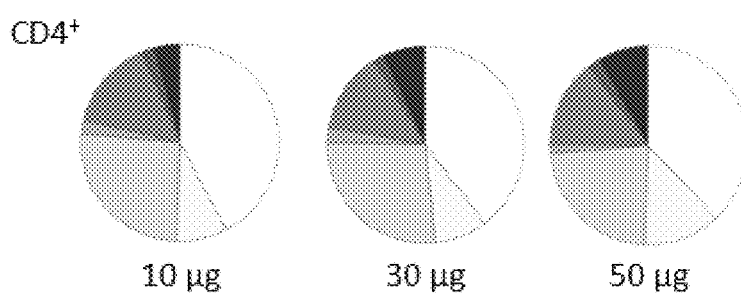
CD4+
FIG. 25B
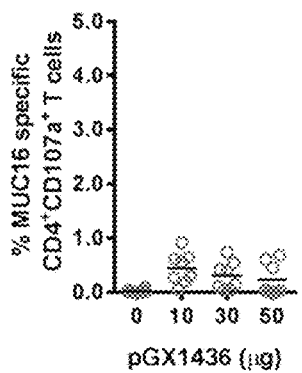
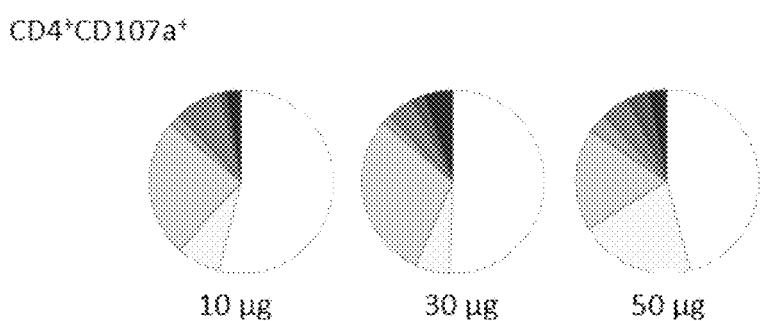
CD4+CD107a+

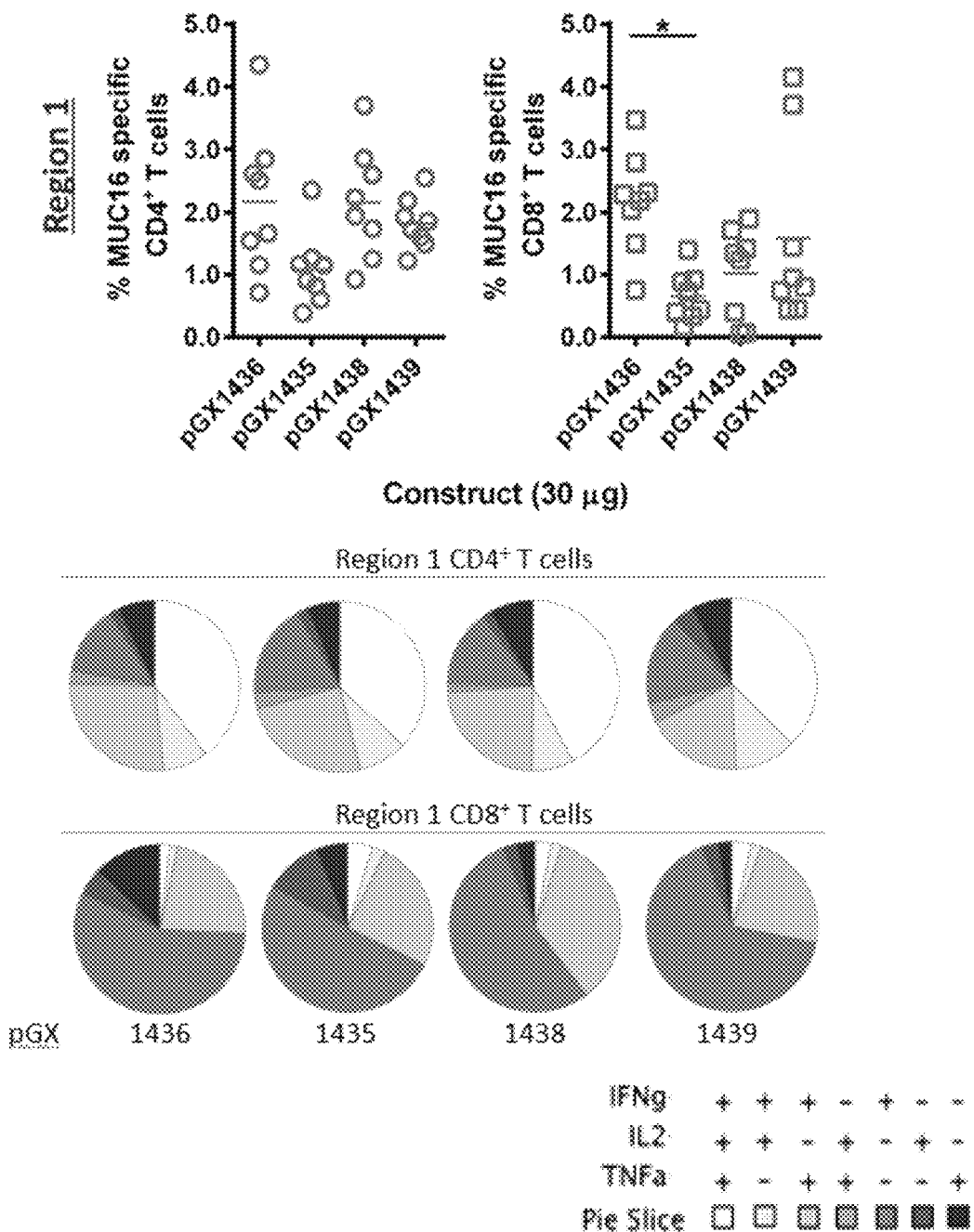

FIG. 29B
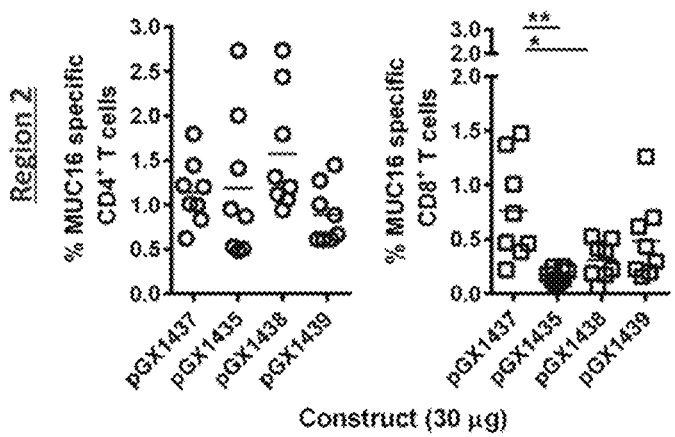
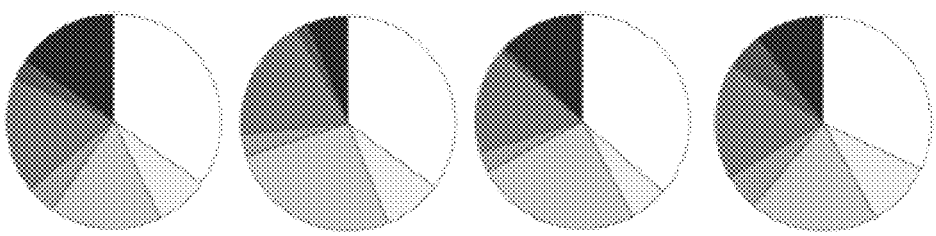
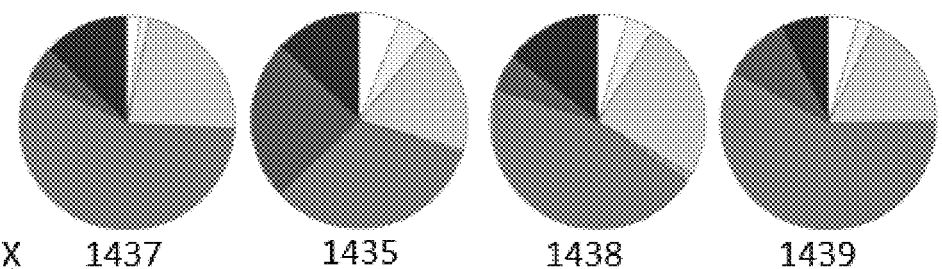

SEQUENCE LISTING

<160> NUMBER OF SEQ ID NOS: 12

<210> SEQ ID NO 1
<211> LENGTH: 4476
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus MUC16 IRC + R59 DNA Coding Sequence"

<400> SEQUENCE: 1

```
atggactgga cctggattct gttcctggtg gcagcagcaa cccgcgtgca ctccacagca    60
gcaggacctc tgctggtgcc attcaccctg aactttacca tcacaaatct gcagtacgag   120
gaggatatgc accacccagg cagcagaaag ttcaacacca cagagagggt gctgcagggc   180
ctgctgggac caatgtttaa gaataccagc gtgggcctgc tgtattccgg atgcaggctg   240
acactgctgc gctccgagaa ggacggagca gcaaccggcg tggatgccat ctgtacacac   300
aggctggacc ccaagagccc tggcctggat cgggagcagc tgtactggga gctgtcccag   360
ctgaccaacg gcatcaagga gctgggcccc tacacactgg accgcaacag cctgtatgtg   420
aatggcttta cccaccggag ctccgtgcca ataccagca cacccggcac ctccacagtg    480
gatctgggca cctccggcac accatctagc ctgccttctc aaccgcagc aggaccactg    540
ctggtgcctt tcacactgaa ctttaccatt accaatctgc agtatgaaga ggacatgagg   600
catcctggca gcagaaagtt caacacgaca gagagagtgc tgcaaggcct gctgaagcca   660
ctgtttaaga atacctctgt ggccccctg tatagtggct gtagactgac actgctgcgc   720
cccgaaaaag atggcgccgc cactggagtc gacgccatct gtacacacag actggacccc   780
aagtctcccg gcctgaacag agaacagctg tattgggaac tgagcaagct gaccaatggc   840
atcacagagc tgggccctta caccctggac agaaactctc tgtatgtgaa tggcttcacc   900
cacaggacat ctgtgcctac cacaagcacc ccaggcacct ccaccgtcga tctgggcacc   960
agcggcacac ttttagcct gccatcccct accaccgccg gaccactgct ggtgccttc   1020
accctgaact ttaccataac caatctgcag tatgaggagg acatgcaccg gcccggcagc   1080
agaaagttca cactacaga gagagtgctg cagggcctgt atcccctat ctttaagaat   1140
tcctctgtgg gccactgta cagcggatgc aggctgacct ctctgcggcc cgaaaaagac   1200
ggagcagcaa caggaatgga tgccgtgtgc ctgtaccacc caaacccaa gaggccaggc   1260
ctggatcgcg agcagctgta ttgggagctg agccagctga cccacaatat cacagagctg   1320
ggcccctact ctctggacag ggatagcctg tatgtgaacg gcttcaccca ccagaattcc   1380
gtgcccacca catctacacc tggcaccagc acagtgtact gggccaccac aggcacccct   1440
agctccttc caggacacac agcacctgga ccactgctga tcccattcac cctgaacttt   1500
accattacaa atctgcacta tgaggagaac atgcagcacc ccggcagccg caagttcaat   1560
accacagagc gggtgctgca aggcctgctg aagccgctgt ttaagaacac cagcgtggga   1620
cctctgtact ctggctgtcg cctgacactg ctgcggcccg agaagcatgg cgcagcaacc   1680
ggcgtggacg ctatttgcac ccacagactg gaccctaagg gcccaggcct ggatagggag   1740
cgcctgtatt gggaactgtc tcagctgacc aattctatca cagagctggg accatacacc   1800
ctggacaggg attctctgta cgtgaacggc ttcaatccac ggtctagcgt gcccaccaca   1860
agcacccctg gcacctccac agtgcacctg gccacctctg gcacaccctc ctctctgcct   1920
ggacacaccg caagccccct gctggtgctg ttcacaatca actttaccat tactaatctg   1980
agatacgagg agaacatgca ccaccctggc tccagaaagt caatactac gaaagggtg   2040
ctgcaaggcc tgctgcgccc agtgtttaag aacacttccg tgggcccct gtatagcggc   2100
tgtaggctga cactgctgcg ccccaagaag gatggcgcag caaccaaggt cgacgctatc   2160
tgtacataca ggcccgaccc taaatcccca ggcctggacc gggagcagct gtattgggag   2220
ctgtctcagc tgacccactc cattaccgaa ctgggaccct acaccctgga cagagattcc   2280
ctgtacgtga atgcttcac acagaggagc tccgtgccta ccacatccat cccaggaacc   2340
cctacagtgg acctgggcac ctccggaacc ccagtgtcta agccaggacc atctgccgca   2400
```

```
agccacctgc tgatcctgtt caccctgaac tttaccataa cgaatctgcg gtacgaggag    2460
aacatgtggc caggctcccg gaagttcaat actaccgaga gagtgctgca aggcctgctg    2520
aggcctctgt ttaagaacac tagcgtgggc ccactgtatt ccggctctcg gctgaccctg    2580
ctgcggcccg aaaaagatgg agaggccaca ggcgtggatg ccatctgcac ccacagacct    2640
gacccaacag gacctggcct ggacagggag cagctgtacc tggagctgtc acagctgact    2700
cactccatta ccgagctggg ccctatact ctggatagag actccctgta cgtcaacggc    2760
ttcacccacc ggtctagcgt gccaaccaca tctacaggcg tggtgagcga ggaacccttc    2820
accctgaact tcaccatcaa caatctgagg tacatggcag acatgggaca gccaggctct    2880
ctgaagttca acatcaccga taatgtgatg aagcacctgc tgagccctct gtttcagcgg    2940
agcagcctgg gagcaaggta caccggatgc cgcgtgatcg ccctgcggtc cgtgaagaac    3000
ggagcagaga cacgggtgga cctgctgtgc acatatctgc agcctctgag cggaccaggc    3060
ctgcccatca gcaggtgtt ccacgagctg tctcagcaga cccacggaat acaaggctg    3120 ggaccctact ccctggacaa ggattctctg tacctgaacg gctataatga gcctggcctg    3180
gacgagcccc ctaccacacc caagcctgcc accacatttc tgccaccccct gagcgaggca    3240 accacagcaa tgggatacca cctgaagacc ctgacactga acttcaccat cagcaatctg    3300
cagtattccc ccgatatggg caagggctct gccaccttta acagcacaga gggcgtgctg    3360
cagcacctgc tgcggcccct gttccagaag agctccatgg gccttttta cctgggctgc    3420 cagctgatct ccctgaggcc tgaaaaagat ggagcagcaa ccggagtgga taccacatgt    3480
acataccacc cagaccccgt gggaccaggc ctggatatcc agcagctgta ctgggaactg    3540
tcccagctga ctcacggcgt gacacagctg ggcttctacg tgctggaccg cgattccctg    3600
tttatcaacg gctacgcccc tcagaatctg tctatccggg gcgagtatca gatcaacttc    3660
cacatcgtga actggaatct gagcaatcct gacccaacct ctagcgagta catcgccctg    3720
ctgcgcgaca tccaggataa ggtgaccaca ctgtataagg ctcccagct gcacgacacc    3780 ttccggtttt gcctggtgac caacctgaca atggattcta tgctggtgac agtgaaggcc    3840
ctgttctcct ctaacctgga ccccagcctg gtggagcagg tgtttctgga taagaccctg    3900
aatgccagct cccactggct gggctccacc taccagctgg tggacatcca cgtgacagag    3960
atggagccaa gcgtgtacca gcccacctct agctcctcta cacagcactt ctacctgaac    4020
tttaccataa ctaatctgcc ctatagccag gatatcgccc agcctggcac cacaaactac    4080
cagcggaaca agagaaatat cgaggacgcc ctgaaccagc tgttcagaaa tagctccatc    4140
aagtcctatt tctctgattg ccaggtgagc acctttaggt ccgtgcctaa ttctcaccac    4200
acaggcgtgg actccctgtg cgccttttct ccactggcaa ggagagtgga tagggtggca    4260
atctacgagg agttcctgag gatgacccgc gccggaacac agctgcaggc ctttaccctg    4320
gacagatcta gcgtgctggt ggatggctat agccctaaca ggaatgagcc actgaccggc    4380
aactccgacc tgcccttctg ggccatcatc ctgatctgtc tggcaggcct gctgggcctg    4440
atcacctgcc tgatctgtgg ctttctggtg tgataa                              4476
```

<210> SEQ ID NO 2
<211> LENGTH: 1490
<212> TYPE: PRT
<213> ORGANISM: Artificial Sequence
<220> FEATURE:
<221> NAME/KEY: source
<223> OTHER INFORMATION: /note="Description of Artificial Sequence:

"Synthetic consensus MUC16 IRC + R59 Protein Sequence"

<400> SEQUENCE: 2

Met Asp Trp Thr Trp Ile Leu Phe Leu Val Ala Ala Thr Arg Val
1               5                   10                  15

His Ser Thr Ala Ala Gly Pro Leu Leu Val Pro Phe Thr Leu Asn Phe
            20                  25                  30

Thr Ile Thr Asn Leu Gln Tyr Glu Glu Asp Met His His Pro Gly Ser
        35                  40                  45

Arg Lys Phe Asn Thr Thr Glu Arg Val Leu Gln Gly Leu Leu Gly Pro
    50                  55                  60

Met Phe Lys Asn Thr Ser Val Gly Leu Leu Tyr Ser Gly Cys Arg Leu
65                  70                  75                  80

Thr Leu Leu Arg Ser Glu Lys Asp Gly Ala Ala Thr Gly Val Asp Ala
                85                  90                  95

Ile Cys Thr His Arg Leu Asp Pro Lys Ser Pro Gly Leu Asp Arg Glu
            100                 105                 110

Gln Leu Tyr Trp Glu Leu Ser Gln Leu Thr Asn Gly Ile Lys Glu Leu
        115                 120                 125

Gly Pro Tyr Thr Leu Asp Arg Asn Ser Leu Tyr Val Asn Gly Phe Thr
    130                 135                 140

His Arg Ser Ser Val Pro Asn Thr Ser Thr Pro Gly Thr Ser Thr Val
145                 150                 155                 160

Asp Leu Gly Thr Ser Gly Thr Pro Ser Ser Leu Pro Ser Pro Thr Ala
                165                 170                 175

Ala Gly Pro Leu Leu Val Pro Phe Thr Leu Asn Phe Thr Ile Thr Asn
            180                 185                 190

Leu Gln Tyr Glu Glu Asp Met Arg His Pro Gly Ser Arg Lys Phe Asn
        195                 200                 205

Thr Thr Glu Arg Val Leu Gln Gly Leu Leu Lys Pro Leu Phe Lys Asn
    210                 215                 220

Thr Ser Val Gly Pro Leu Tyr Ser Gly Cys Arg Leu Thr Leu Leu Arg
225                 230                 235                 240

Pro Glu Lys Asp Gly Ala Ala Thr Gly Val Asp Ala Ile Cys Thr His
                245                 250                 255

Arg Leu Asp Pro Lys Ser Pro Gly Leu Asn Arg Glu Gln Leu Tyr Trp
            260                 265                 270

Glu Leu Ser Lys Leu Thr Asn Gly Ile Thr Glu Leu Gly Pro Tyr Thr
        275                 280                 285

Leu Asp Arg Asn Ser Leu Tyr Val Asn Gly Phe Thr His Arg Thr Ser
    290                 295                 300

Val Pro Thr Thr Ser Thr Pro Gly Thr Ser Thr Val Asp Leu Gly Thr
305                 310                 315                 320

Ser Gly Thr Pro Phe Ser Leu Pro Ser Pro Thr Thr Ala Gly Pro Leu
                325                 330                 335

Leu Val Pro Phe Thr Leu Asn Phe Thr Ile Thr Asn Leu Gln Tyr Glu
            340                 345                 350

Glu Asp Met His Arg Pro Gly Ser Arg Lys Phe Asn Thr Thr Glu Arg
        355                 360                 365

Val Leu Gln Gly Leu Leu Ser Pro Ile Phe Lys Asn Ser Ser Val Gly
    370                 375                 380

Pro Leu Tyr Ser Gly Cys Arg Leu Thr Ser Leu Arg Pro Glu Lys Asp
385                 390                 395                 400

```
Gly Ala Ala Thr Gly Met Asp Ala Val Cys Leu Tyr His Pro Asn Pro
                405                 410                 415
Lys Arg Pro Gly Leu Asp Arg Glu Gln Leu Tyr Trp Glu Leu Ser Gln
            420                 425                 430
Leu Thr His Asn Ile Thr Glu Leu Gly Pro Tyr Ser Leu Asp Arg Asp
        435                 440                 445
Ser Leu Tyr Val Asn Gly Phe Thr His Gln Asn Ser Val Pro Thr Thr
450                 455                 460
Ser Thr Pro Gly Thr Ser Thr Val Tyr Trp Ala Thr Gly Thr Pro
465                 470                 475                 480
Ser Ser Phe Pro Gly His Thr Ala Pro Gly Pro Leu Leu Ile Pro Phe
                485                 490                 495
Thr Leu Asn Phe Thr Ile Thr Asn Leu His Tyr Glu Glu Asn Met Gln
            500                 505                 510
His Pro Gly Ser Arg Lys Phe Asn Thr Thr Glu Arg Val Leu Gln Gly
        515                 520                 525
Leu Leu Lys Pro Leu Phe Lys Asn Thr Ser Val Gly Pro Leu Tyr Ser
    530                 535                 540
Gly Cys Arg Leu Thr Leu Leu Arg Pro Glu Lys His Gly Ala Ala Thr
545                 550                 555                 560
Gly Val Asp Ala Ile Cys Thr His Arg Leu Asp Pro Lys Gly Pro Gly
                565                 570                 575
Leu Asp Arg Glu Arg Leu Tyr Trp Glu Leu Ser Gln Leu Thr Asn Ser
            580                 585                 590
Ile Thr Glu Leu Gly Pro Tyr Thr Leu Asp Arg Asp Ser Leu Tyr Val
        595                 600                 605
Asn Gly Phe Asn Pro Arg Ser Ser Val Pro Thr Thr Ser Thr Pro Gly
    610                 615                 620
Thr Ser Thr Val His Leu Ala Thr Ser Gly Thr Pro Ser Ser Leu Pro
625                 630                 635                 640
Gly His Thr Ala Ser Pro Leu Leu Val Leu Phe Thr Ile Asn Phe Thr
                645                 650                 655
Ile Thr Asn Leu Arg Tyr Glu Glu Asn Met His His Pro Gly Ser Arg
            660                 665                 670
Lys Phe Asn Thr Thr Glu Arg Val Leu Gln Gly Leu Leu Arg Pro Val
    675                 680                 685
Phe Lys Asn Thr Ser Val Gly Pro Leu Tyr Ser Gly Cys Arg Leu Thr
    690                 695                 700
Leu Leu Arg Pro Lys Lys Asp Gly Ala Ala Thr Lys Val Asp Ala Ile
705                 710                 715                 720
Cys Thr Tyr Arg Pro Asp Pro Lys Ser Pro Gly Leu Asp Arg Glu Gln
                725                 730                 735
Leu Tyr Trp Glu Leu Ser Gln Leu Thr His Ser Ile Thr Glu Leu Gly
            740                 745                 750
Pro Tyr Thr Leu Asp Arg Asp Ser Leu Tyr Val Asn Gly Phe Thr Gln
        755                 760                 765
Arg Ser Ser Val Pro Thr Thr Ser Ile Pro Gly Thr Pro Thr Val Asp
    770                 775                 780
Leu Gly Thr Ser Gly Thr Pro Val Ser Lys Pro Gly Pro Ser Ala Ala
785                 790                 795                 800
Ser His Leu Leu Ile Leu Phe Thr Leu Asn Phe Thr Ile Thr Asn Leu
                805                 810                 815
Arg Tyr Glu Glu Asn Met Trp Pro Gly Ser Arg Lys Phe Asn Thr Thr
```

820             825             830
Glu Arg Val Leu Gln Gly Leu Leu Arg Pro Leu Phe Lys Asn Thr Ser
                    835             840             845
Val Gly Pro Leu Tyr Ser Gly Ser Arg Leu Thr Leu Leu Arg Pro Glu
850                 855             860
Lys Asp Gly Glu Ala Thr Gly Val Asp Ala Ile Cys Thr His Arg Pro
865                 870             875                             880
Asp Pro Thr Gly Pro Gly Leu Asp Arg Glu Gln Leu Tyr Leu Glu Leu
                    885             890             895
Ser Gln Leu Thr His Ser Ile Thr Glu Leu Gly Pro Tyr Thr Leu Asp
                    900             905             910
Arg Asp Ser Leu Tyr Val Asn Gly Phe Thr His Arg Ser Ser Val Pro
                    915             920             925
Thr Thr Ser Thr Gly Val Val Ser Glu Glu Pro Phe Thr Leu Asn Phe
                    930             935             940
Thr Ile Asn Asn Leu Arg Tyr Met Ala Asp Met Gly Gln Pro Gly Ser
945                 950             955                             960
Leu Lys Phe Asn Ile Thr Asp Asn Val Met Lys His Leu Leu Ser Pro
                    965             970             975
Leu Phe Gln Arg Ser Ser Leu Gly Ala Arg Tyr Thr Gly Cys Arg Val
                    980             985             990
Ile Ala Leu Arg Ser Val Lys Asn Gly Ala Glu Thr Arg Val Asp Leu
                    995             1000            1005
Leu Cys Thr Tyr Leu Gln Pro Leu Ser Gly Pro Gly Leu Pro Ile
       1010            1015            1020
Lys Gln Val Phe His Glu Leu Ser Gln Gln Thr His Gly Ile Thr
       1025            1030            1035
Arg Leu Gly Pro Tyr Ser Leu Asp Lys Asp Ser Leu Tyr Leu Asn
       1040            1045            1050
Gly Tyr Asn Glu Pro Gly Leu Asp Glu Pro Pro Thr Thr Pro Lys
       1055            1060            1065
Pro Ala Thr Thr Phe Leu Pro Pro Leu Ser Glu Ala Thr Thr Ala
       1070            1075            1080
Met Gly Tyr His Leu Lys Thr Leu Thr Leu Asn Phe Thr Ile Ser
       1085            1090            1095
Asn Leu Gln Tyr Ser Pro Asp Met Gly Lys Gly Ser Ala Thr Phe
       1100            1105            1110
Asn Ser Thr Glu Gly Val Leu Gln His Leu Leu Arg Pro Leu Phe
       1115            1120            1125
Gln Lys Ser Ser Met Gly Pro Phe Tyr Leu Gly Cys Gln Leu Ile
       1130            1135            1140
Ser Leu Arg Pro Glu Lys Asp Gly Ala Ala Thr Gly Val Asp Thr
       1145            1150            1155
Thr Cys Thr Tyr His Pro Asp Pro Val Gly Pro Gly Leu Asp Ile
       1160            1165            1170
Gln Gln Leu Tyr Trp Glu Leu Ser Gln Leu Thr His Gly Val Thr
       1175            1180            1185
Gln Leu Gly Phe Tyr Val Leu Asp Arg Asp Ser Leu Phe Ile Asn
       1190            1195            1200
Gly Tyr Ala Pro Gln Asn Leu Ser Ile Arg Gly Glu Tyr Gln Ile
       1205            1210            1215
Asn Phe His Ile Val Asn Trp Asn Leu Ser Asn Pro Asp Pro Thr
       1220            1225            1230

```
Ser Ser Glu Tyr Ile Ala Leu Leu Arg Asp Ile Gln Asp Lys Val
    1235                1240                1245

Thr Thr Leu Tyr Lys Gly Ser Gln Leu His Asp Thr Phe Arg Phe
    1250                1255                1260

Cys Leu Val Thr Asn Leu Thr Met Asp Ser Met Leu Val Thr Val
    1265                1270                1275

Lys Ala Leu Phe Ser Ser Asn Leu Asp Pro Ser Leu Val Glu Gln
    1280                1285                1290

Val Phe Leu Asp Lys Thr Leu Asn Ala Ser Ser His Trp Leu Gly
    1295                1300                1305

Ser Thr Tyr Gln Leu Val Asp Ile His Val Thr Glu Met Glu Pro
    1310                1315                1320

Ser Val Tyr Gln Pro Thr Ser Ser Ser Ser Thr Gln His Phe Tyr
    1325                1330                1335

Leu Asn Phe Thr Ile Thr Asn Leu Pro Tyr Ser Gln Asp Ile Ala
    1340                1345                1350

Gln Pro Gly Thr Thr Asn Tyr Gln Arg Asn Lys Arg Asn Ile Glu
    1355                1360                1365

Asp Ala Leu Asn Gln Leu Phe Arg Asn Ser Ser Ile Lys Ser Tyr
    1370                1375                1380

Phe Ser Asp Cys Gln Val Ser Thr Phe Arg Ser Val Pro Asn Ser
    1385                1390                1395

His His Thr Gly Val Asp Ser Leu Cys Ala Phe Ser Pro Leu Ala
    1400                1405                1410

Arg Arg Val Asp Arg Val Ala Ile Tyr Glu Glu Phe Leu Arg Met
    1415                1420                1425

Thr Arg Ala Gly Thr Gln Leu Gln Ala Phe Thr Leu Asp Arg Ser
    1430                1435                1440

Ser Val Leu Val Asp Gly Tyr Ser Pro Asn Arg Asn Glu Pro Leu
    1445                1450                1455

Thr Gly Asn Ser Asp Leu Pro Phe Trp Ala Ile Ile Leu Ile Cys
    1460                1465                1470

Leu Ala Gly Leu Leu Gly Leu Ile Thr Cys Leu Ile Cys Gly Phe
    1475                1480                1485

Leu Val
    1490

<210> SEQ ID NO 3
<211> LENGTH: 1932
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic consensus MUC16 RMC DNA Coding Sequence"

<400> SEQUENCE: 3
atggattgga cttggattct gttcctggtc gccgccgcaa ctcgggtgca ttctactgct    60
gctgggccac tgctggtgcc ttttacactg aacttcacca tcacaaatct gcagtacgag   120
gaggacatgc accaccctgg ctctcggaag ttcaacacca cagagagagt gctgcagggc   180
ctgctgggcc caatgtttaa gaataccagc gtgggcctgc tgtattccgg atgccggctg   240
acactgctga tccgagaa ggacggagca gcaaccggag tggatgccat ctgtacacac   300
aggctggacc caaagtcccc aggcctggat agagagcagc tgtactggga gctgtctcag   360
```

```
ctgaccaacg gcatcaagga gctgggcccc tacacactgg accggaacag cctgtatgtg    420
aatggcttta cccacagaag ctccgtgcca ataccagca cacccggcac ctccacagtg     480
gatctgggca cctctggcac accttctagc ctgccaagcc ctaccgcagc aggaccactg    540
ctggtgccct tcacactgaa ctttaccatt accaatctgc agtatgaaga ggacatgagg    600
cacccaggct cccgcaagtt caacactacc gagcgggtgc tgcaaggcct gctgaagcct    660
ctgtttaaga atacctctgt gggcccactg tatagtggct gccggctgac actgctgcgg    720
cccgaaaaag acggagcagc aaccggcgtg gatgctattt gcacccacag gctggacccc    780
aagagcccag gcctgaaccg cgaacagctg tattgggagc tgtccaagct gaccaatggc    840
atcacagagc tgggcccta caccctggac agaaattccc tgtacgtgaa tggcttcacc    900
caccgcacat ctgtgcctac cacaagcacc ccaggcacct ccacagtgga tctgggcacc    960
tccggcacac ccttttccct gccatctcca accacagcag acctctgct ggtgccattc     1020
accctgaact ttaccattac taatctgcag tatgaagaag acatgcacag gcctggctct    1080
cgcaagttca cactactga gagggtgctg cagggcctgt taagcccaat ctttaagaat      1140
tcctctgtgg gccctctgta ttccggatgc aggctgacct ctctgcgccc agaaaaagat    1200
ggagcagcaa caggaatgga tgccgtgtgc ctgtaccacc ctaacccaaa gcggcccggc    1260
ctggacaggg agcagctgta ttgggaactg agccagctga cccacaatat cacagagctg    1320
ggcccttact ctctggaccg cgatagcctg tatgtgaacg gcttcaccca ccagaattcc    1380
gtgcccacca catctacacc tggcaccagc acagtgtact gggccaccac aggcacccc     1440
agctcctttc ctggacacac agcaccagga cctctgctga tccccttcac cctgaacttt    1500
accataacaa atctgcacta tgaggagaac atgcagcacc ctggcagcag gaagttcaat    1560
accacagagc gcgtgctgca aggcctgctg aagccgctgt ttaagaacac cagcgtggga    1620
ccactgtaca gcggctgcag gctgaccctg ctgcgccctg agaagcatgg cgccgccacc    1680
ggcgtggatg ctatctgcac acatagactg accccaagg acctggcct ggatagggag      1740
agactgtact gggaactgtc ccagctgacc aactcaatta cagagctggg cccatacacc    1800
ctggaccggg attctctgta cgtgaacggc ttcaatccaa gatctagcgt ccctaccaca    1860
tctaccccctg gacaagtac cgtgcatctg gctacaagcg gaactccttc aagtctgcct    1920
ggacactgat aa                                                        1932
```

```
<210> SEQ ID NO 4
<211> LENGTH: 642
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus MUC16 RMC Protein Sequence"

<400> SEQUENCE: 4

Met Asp Trp Thr Trp Ile Leu Phe Leu Val Ala Ala Thr Arg Val
1               5                   10                  15

His Ser Thr Ala Ala Gly Pro Leu Leu Val Pro Phe Thr Leu Asn Phe
            20                  25                  30

Thr Ile Thr Asn Leu Gln Tyr Glu Glu Asp Met His His Pro Gly Ser
        35                  40                  45

Arg Lys Phe Asn Thr Thr Glu Arg Val Leu Gln Gly Leu Leu Gly Pro
    50                  55                  60

Met Phe Lys Asn Thr Ser Val Gly Leu Leu Tyr Ser Gly Cys Arg Leu
```

-continued

```
            65                  70                  75                  80
        Thr Leu Leu Arg Ser Glu Lys Asp Gly Ala Ala Thr Gly Val Asp Ala
                        85                  90                  95

Ile Cys Thr His Arg Leu Asp Pro Lys Ser Pro Gly Leu Asp Arg Glu
                        100                 105                 110

Gln Leu Tyr Trp Glu Leu Ser Gln Leu Thr Asn Gly Ile Lys Glu Leu
                        115                 120                 125

Gly Pro Tyr Thr Leu Asp Arg Asn Ser Leu Tyr Val Asn Gly Phe Thr
                        130                 135                 140

His Arg Ser Ser Val Pro Asn Thr Ser Thr Pro Gly Thr Ser Thr Val
        145                 150                 155                 160

Asp Leu Gly Thr Ser Gly Thr Pro Ser Ser Leu Pro Ser Pro Thr Ala
                        165                 170                 175

Ala Gly Pro Leu Leu Val Pro Phe Thr Leu Asn Phe Thr Ile Thr Asn
                        180                 185                 190

Leu Gln Tyr Glu Glu Asp Met Arg His Pro Gly Ser Arg Lys Phe Asn
                        195                 200                 205

Thr Thr Glu Arg Val Leu Gln Gly Leu Leu Lys Pro Leu Phe Lys Asn
                        210                 215                 220

Thr Ser Val Gly Pro Leu Tyr Ser Gly Cys Arg Leu Thr Leu Leu Arg
        225                 230                 235                 240

Pro Glu Lys Asp Gly Ala Ala Thr Gly Val Asp Ala Ile Cys Thr His
                        245                 250                 255

Arg Leu Asp Pro Lys Ser Pro Gly Leu Asn Arg Glu Gln Leu Tyr Trp
                        260                 265                 270

Glu Leu Ser Lys Leu Thr Asn Gly Ile Thr Glu Leu Gly Pro Tyr Thr
                        275                 280                 285

Leu Asp Arg Asn Ser Leu Tyr Val Asn Gly Phe Thr His Arg Thr Ser
                        290                 295                 300

Val Pro Thr Thr Ser Thr Pro Gly Thr Ser Thr Val Asp Leu Gly Thr
        305                 310                 315                 320

Ser Gly Thr Pro Phe Ser Leu Pro Ser Pro Thr Thr Ala Gly Pro Leu
                        325                 330                 335

Leu Val Pro Phe Thr Leu Asn Phe Thr Ile Thr Asn Leu Gln Tyr Glu
                        340                 345                 350

Glu Asp Met His Arg Pro Gly Ser Arg Lys Phe Asn Thr Thr Glu Arg
                        355                 360                 365

Val Leu Gln Gly Leu Leu Ser Pro Ile Phe Lys Asn Ser Ser Val Gly
                        370                 375                 380

Pro Leu Tyr Ser Gly Cys Arg Leu Thr Ser Leu Arg Pro Glu Lys Asp
        385                 390                 395                 400

Gly Ala Ala Thr Gly Met Asp Ala Val Cys Leu Tyr His Pro Asn Pro
                        405                 410                 415

Lys Arg Pro Gly Leu Asp Arg Glu Gln Leu Tyr Trp Glu Leu Ser Gln
                        420                 425                 430

Leu Thr His Asn Ile Thr Glu Leu Gly Pro Tyr Ser Leu Asp Arg Asp
                        435                 440                 445

Ser Leu Tyr Val Asn Gly Phe Thr His Gln Asn Ser Val Pro Thr Thr
                        450                 455                 460

Ser Thr Pro Gly Thr Ser Thr Val Tyr Trp Ala Thr Gly Thr Pro
        465                 470                 475                 480

Ser Ser Phe Pro Gly His Thr Ala Pro Gly Pro Leu Leu Ile Pro Phe
                        485                 490                 495
```

```
Thr Leu Asn Phe Thr Ile Thr Asn Leu His Tyr Glu Glu Asn Met Gln
            500                 505                 510

His Pro Gly Ser Arg Lys Phe Asn Thr Thr Glu Arg Val Leu Gln Gly
            515                 520                 525

Leu Leu Lys Pro Leu Phe Lys Asn Thr Ser Val Gly Pro Leu Tyr Ser
            530                 535                 540

Gly Cys Arg Leu Thr Leu Leu Arg Pro Glu Lys His Gly Ala Ala Thr
545                 550                 555                 560

Gly Val Asp Ala Ile Cys Thr His Arg Leu Asp Pro Lys Gly Pro Gly
                    565                 570                 575

Leu Asp Arg Glu Arg Leu Tyr Trp Glu Leu Ser Gln Leu Thr Asn Ser
            580                 585                 590

Ile Thr Glu Leu Gly Pro Tyr Thr Leu Asp Arg Asp Ser Leu Tyr Val
            595                 600                 605

Asn Gly Phe Asn Pro Arg Ser Ser Val Pro Thr Thr Ser Thr Pro Gly
            610                 615                 620

Thr Ser Thr Val His Leu Ala Thr Ser Gly Thr Pro Ser Ser Leu Pro
625                 630                 635                 640

Gly His

<210> SEQ ID NO 5
<211> LENGTH: 2136
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic consensus MUC16 NRC DNA Coding Sequence"

<400> SEQUENCE: 5
atggactgga cttggattct gttcctggtc gctgccgcca ccgcgtgca tagtgccgca      60 tctcacctgc tgattctgtt caccctgaac ttcaccatca aaatctgcg gtacgaggag     120 aacatgtggc caggcagccg caagttcaat accacagagc gggtgctgca gggcctgctg    180
cggcccctgt ttaagaacac ctccgtgggc ccctgtatt ctggcagcag gctgacctg     240 ctgcgcccag agaaggacgg agaggcaaca ggcgtggatg ccatctgcac ccacaggcct    300
gacccaacag gaccaggcct ggatagggag cagctgtacc tggagctgag ccagctgacc    360
cactccatca cagagctggg accatacacc ctggacaggg attccctgta tgtgaacggc    420
tttacccaca gaagctccgt gcccaccaca tctacaggcg tggtgagcga ggagcccttc    480
accctgaact tcaccatcaa caatctgagg tacatggcag acatgggaca gccaggcagc    540
ctgaagttca acatcaccga taatgtgatg aagcacctgc tgtcccctct gtttcagcgg    600
tctagcctgg agcaaggta caccggctgc agagtgatcg ccctgaggtc cgtgaagaac    660
ggagcagaga cacgggtgga cctgctgtgc acatatctgc agcctctgag cggaccaggc    720
ctgcctatca agcaggtgtt ccacgagctg tctcagcaga cccacggaat cacacgcctg    780
ggaccttact ccctggacaa ggattctctg tacctgaacg ctataatga gccaggcctg    840 gacgagcccc ctaccacacc caagcctgcc accacatttc tgccacccct gagcgaggca    900
accacagcaa tgggatacca cctgaagacc ctgacactga acttcaccat cagcaatctg    960
cagtattccc ccgatatggg caagggctct gccaccttta atagcacaga gggcgtgctg   1020
cagcacctgc tgaggcctct gttccagaag tcctctatgg gccccttcta cctgggatgc   1080
cagctgatct ccctgcgccc tgagaaggac ggagcagcaa ccggagtgga taccacatgt   1140
```

-continued

```
acataccacc cagaccccgt gggaccaggc ctggatatcc agcagctgta ttgggaactg    1200
tcccagctga cccacggcgt gacacagctg ggcttctatg tgctggaccg ggattctctg    1260
tttatcaacg gctacgcccc tcagaatctg agcatcagag gcgagtatca gatcaacttc    1320
cacatcgtga actggaatct gtctaatcct gatccaacca gctccgagta catcgccctg    1380
ctgcgggaca tccaggataa ggtgaccaca ctgtataagg gcagccagct gcacgacacc    1440
ttcagatttt gtctggtgac caacctgaca atggattcca tgctggtgac agtgaaggcc    1500
ctgttctcta gcaacctgga cccttctctg gtggagcagg tgtttctgga taagaccctg    1560
aatgcctcct ctcactggct gggctctacc taccagctgg tggacatcca cgtgacagag    1620
atggagccaa gcgtgtatca gcccaccagc tcctctagca cacagcactt ctacctgaac    1680
tttaccatca caaatctgcc ctatagccag gatatcgccc agcctggcac acaaaactac    1740
cagaggaaca agcgcaatat cgaggacgcc ctgaaccagc tgttcaggaa ttcctctatc    1800 aagtccatt tctctgattg ccaggtgagc acctttcgct ccgtgccaaa ttctcaccac    1860
acaggcgtgg actccctgtg cgccttttct cccctggcac ggagagtgga tagggtggca    1920
atctacgagg agttcctgcg gatgaccaga gccggcacac agctgcaggc ctttaccctg    1980
gacaggagct ccgtgctggt ggatggctat agccctaacc gcaatgagcc actgacaggc    2040
aattccgacc tgcccttctg ggccatcatc ctgatttgcc tggctggact gctggggctg    2100
attacctgtc tgatttgtgg gttcctggtg tgataa                              2136
```

<210> SEQ ID NO 6
<211> LENGTH: 710
<212> TYPE: PRT
<213> ORGANISM: Artificial Sequence
<220> FEATURE:
<221> NAME/KEY: source
<223> OTHER INFORMATION: /note="Description of Artificial Sequence: Synthetic consensus MUC16 NRC Protein Sequence"

<400> SEQUENCE: 6

```
Met Asp Trp Thr Trp Ile Leu Phe Leu Val Ala Ala Thr Arg Val
1               5                   10                  15

His Ser Ala Ala Ser His Leu Leu Ile Leu Phe Thr Leu Asn Phe Thr
                20                  25                  30

Ile Thr Asn Leu Arg Tyr Glu Glu Asn Met Trp Pro Gly Ser Arg Lys
            35                  40                  45

Phe Asn Thr Thr Glu Arg Val Leu Gln Gly Leu Leu Arg Pro Leu Phe
        50                  55                  60

Lys Asn Thr Ser Val Gly Pro Leu Tyr Ser Gly Ser Arg Leu Thr Leu
65                  70                  75                  80

Leu Arg Pro Glu Lys Asp Gly Glu Ala Thr Gly Val Asp Ala Ile Cys
                85                  90                  95

Thr His Arg Pro Asp Pro Thr Gly Pro Gly Leu Asp Arg Glu Gln Leu
            100                 105                 110

Tyr Leu Glu Leu Ser Gln Leu Thr His Ser Ile Thr Glu Leu Gly Pro
        115                 120                 125

Tyr Thr Leu Asp Arg Asp Ser Leu Tyr Val Asn Gly Phe Thr His Arg
    130                 135                 140

Ser Ser Val Pro Thr Thr Ser Thr Gly Val Val Ser Glu Glu Pro Phe
145                 150                 155                 160

Thr Leu Asn Phe Thr Ile Asn Asn Leu Arg Tyr Met Ala Asp Met Gly
                165                 170                 175
```

-continued

Gln Pro Gly Ser Leu Lys Phe Asn Ile Thr Asp Asn Val Met Lys His
            180                 185                 190

Leu Leu Ser Pro Leu Phe Gln Arg Ser Ser Leu Gly Ala Arg Tyr Thr
            195                 200                 205

Gly Cys Arg Val Ile Ala Leu Arg Ser Val Lys Asn Gly Ala Glu Thr
            210                 215                 220

Arg Val Asp Leu Leu Cys Thr Tyr Leu Gln Pro Leu Ser Gly Pro Gly
225                 230                 235                 240

Leu Pro Ile Lys Gln Val Phe His Glu Leu Ser Gln Gln Thr His Gly
            245                 250                 255

Ile Thr Arg Leu Gly Pro Tyr Ser Leu Asp Lys Asp Ser Leu Tyr Leu
            260                 265                 270

Asn Gly Tyr Asn Glu Pro Gly Leu Asp Glu Pro Pro Thr Thr Pro Lys
            275                 280                 285

Pro Ala Thr Thr Phe Leu Pro Pro Leu Ser Glu Ala Thr Thr Ala Met
            290                 295                 300

Gly Tyr His Leu Lys Thr Leu Thr Leu Asn Phe Thr Ile Ser Asn Leu
305                 310                 315                 320

Gln Tyr Ser Pro Asp Met Gly Lys Gly Ser Ala Thr Phe Asn Ser Thr
            325                 330                 335

Glu Gly Val Leu Gln His Leu Leu Arg Pro Leu Phe Gln Lys Ser Ser
            340                 345                 350

Met Gly Pro Phe Tyr Leu Gly Cys Gln Leu Ile Ser Leu Arg Pro Glu
            355                 360                 365

Lys Asp Gly Ala Ala Thr Gly Val Asp Thr Thr Cys Thr Tyr His Pro
370                 375                 380

Asp Pro Val Gly Pro Gly Leu Asp Ile Gln Gln Leu Tyr Trp Glu Leu
385                 390                 395                 400

Ser Gln Leu Thr His Gly Val Thr Gln Leu Gly Phe Tyr Val Leu Asp
            405                 410                 415

Arg Asp Ser Leu Phe Ile Asn Gly Tyr Ala Pro Gln Asn Leu Ser Ile
            420                 425                 430

Arg Gly Glu Tyr Gln Ile Asn Phe His Ile Val Asn Trp Asn Leu Ser
            435                 440                 445

Asn Pro Asp Pro Thr Ser Ser Glu Tyr Ile Ala Leu Leu Arg Asp Ile
450                 455                 460

Gln Asp Lys Val Thr Thr Leu Tyr Lys Gly Ser Gln Leu His Asp Thr
465                 470                 475                 480

Phe Arg Phe Cys Leu Val Thr Asn Leu Thr Met Asp Ser Met Leu Val
            485                 490                 495

Thr Val Lys Ala Leu Phe Ser Ser Asn Leu Asp Pro Ser Leu Val Glu
            500                 505                 510

Gln Val Phe Leu Asp Lys Thr Leu Asn Ala Ser Ser His Trp Leu Gly
            515                 520                 525

Ser Thr Tyr Gln Leu Val Asp Ile His Val Thr Glu Met Glu Pro Ser
            530                 535                 540

Val Tyr Gln Pro Thr Ser Ser Ser Thr Gln His Phe Tyr Leu Asn
545                 550                 555                 560

Phe Thr Ile Thr Asn Leu Pro Tyr Ser Gln Asp Ile Ala Gln Pro Gly
            565                 570                 575

Thr Thr Asn Tyr Gln Arg Asn Lys Arg Asn Ile Glu Asp Ala Leu Asn
            580                 585                 590

-continued

```
Gln Leu Phe Arg Asn Ser Ser Ile Lys Ser Tyr Phe Ser Asp Cys Gln
            595                 600                 605

Val Ser Thr Phe Arg Ser Val Pro Asn Ser His His Thr Gly Val Asp
        610                 615                 620

Ser Leu Cys Ala Phe Ser Pro Leu Ala Arg Arg Val Asp Arg Val Ala
625                 630                 635                 640

Ile Tyr Glu Glu Phe Leu Arg Met Thr Arg Ala Gly Thr Gln Leu Gln
            645                 650                 655

Ala Phe Thr Leu Asp Arg Ser Ser Val Leu Val Asp Gly Tyr Ser Pro
        660                 665                 670

Asn Arg Asn Glu Pro Leu Thr Gly Asn Ser Asp Leu Pro Phe Trp Ala
            675                 680                 685

Ile Ile Leu Ile Cys Leu Ala Gly Leu Leu Gly Leu Ile Thr Cys Leu
            690                 695                 700

Ile Cys Gly Phe Leu Val
705                 710
```

<210> SEQ ID NO 7
<211> LENGTH: 4029
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic consensus MUC16 IRC DNA Coding Sequence"

<400> SEQUENCE: 7

```
atggactgga cctggattct gttcctggtg gcagcagcaa ccagggtgca ctccacagca    60
gcaggacctc tgctggtgcc attcaccctg aactttacca tcacaaatct gcagtacgag   120
gaggatatgc accaccccgg cagccgcaag ttcaacacca cagagcgggt gctgcagggc   180
ctgctgggac tatgtttaa gaataccagc gtgggcctgc tgtattccgg atgcaggctg   240
acactgctgc gctccgagaa ggacggagca gcaaccggcg tggatgccat ctgtacacac   300
aggctggacc caaagtctcc cggcctggat cgcgagcagc tgtactggga gctgagccag   360
ctgaccaacg gcatcaagga gctgggcccc tacacactgg accggaacag cctgtatgtg   420
aatggcttca cccacagaag ctccgtgcca ataccctcca cacccggcac tctctacagtg   480
gatctgggca cctctggcac accctctagc ctgcctagcc aaccgcagc aggaccactg   540
ctggtgcctt tcacactgaa ctttaccatt accaatctgc agtatgaaga ggacatgcgg   600
caccctggca gcagaaagtt caacactacc gagcgcgtgc tgcaaggcct gctgaagcca   660
ctgtttaaga atacctctgt gggccccctg tatagtggct gtagactgac actgctgcgc   720
cctgaaaaag atggcgccgc cactggagtc gacgctattt gcacccacag gctggacccc   780
aagtccccag gcctgaacag agaacagctg tattgggagc tgtctaagct gaccaatggc   840
atcacagagc tgggcccata caccctggac aggaactctc tgtacgtcaa tggcttcacc   900
caccgcacaa gcgtgcctac acatccacc ccaggcacct ctaccgtcga tctgggcacc   960
agcggcacac cattttccct gccatctcct accaccgccg gaccactgct ggtgccttc  1020
accctgaact ttaccataac caatctgcag tatgaggagg acatgcaccg gcccggctct  1080
agaaagttca acactactga acgggtgctg caaggcctgt aagccctat ctttaagaat  1140
tcctctgtgg gcccactgta cagcggatgc aggctgacct ctctgcggcc cgaaaaagac  1200
ggagcagcaa caggaatgga tgccgtgtgc ctgtaccacc caaccccaa gaggcctggc  1260
ctggacagag agcagctgta ttgggaactg tcccagctga cccacaatat cacagagctg  1320
```

-continued

```
ggcccctaca gcctggacag agattccctg tatgtgaacg cttcaccca ccagaattct    1380
gtgcccacca caagcacacc tggcacctcc acagtgtact gggccaccac aggcacccct    1440
agctcctttc caggacacac agcacctgga ccactgctga tcccttcac cctgaacttt    1500
accattacaa atctgcacta tgaggagaac atgcagcacc caggcagcag aaagttcaat    1560
accacagaga gggtgctgca aggcctgctg aagccgctgt ttaagaacac cagcgtggga    1620
cctctgtact ctggctgtcg cctgacactg ctgcggcccg agaagcatgg cgcagcaacc    1680
ggcgtggacg ctatttgcac tcatagactg gaccccaagg gacctggcct ggatagggag    1740
agactgtact gggaactgtc tcagctgacc aattccatta cagagctggg cccttacacc    1800
ctggaccggg acagcctgta cgtcaacggc ttcaatccaa gatctagcgt gcccaccaca    1860
tccacccctg gcacctctac agtgcacctg gccaccagcg aacaccctc ctctctgcct    1920
ggacacaggg gaaggaagcg gagaagcgcc gcatcccacc tgctgatcct gttcaccctg    1980
aactttacca taacgaatct gagatacgag gagaacatgt ggcctggctc ccgcaagttc    2040
aatactaccg aacgggtgct gcagggcctg ctgcggcccc tgtttaagaa cacttccgtg    2100
ggcccctgt attctggcag caggctgacc ctgctgcgcc cagagaagga cggagaggca    2160
acaggcgtgg atgccatctg cacccacagg cccgacccta caggaccagg cctggatagg    2220
gagcagctgt acctggagct gtcccagctg actcactcaa ttaccgaact gggaccttac    2280
accctggaca gggatagtct gtacgtgaat ggcttcaccc atcgcagctc cgtgccaacc    2340
acatctacag gcgtggtgag cgaggaaccc ttcaccctga acttcaccat caacaatctg    2400
aggtacatgg ccgacatggg ccagccaggc tccctgaagt tcaacatcac cgataatgtg    2460
atgaagcacc tgctgtctcc cctgtttcag aggtctagcc tgggagcaag gtacaccgga    2520
tgcagagtga tcgccctgag gtccgtgaag aacggagcag agacacgggt ggacctgctg    2580
tgcacatatc tgcagcctct gagcggacca ggcctgccca tcaagcaggt gttccacgag    2640
ctgtcccagc agacccacgg aatcacaagg ctgggacctt actccctgga caaggattct    2700
ctgtacctga acggctataa tgagccaggc ctggacgagc cccctaccac accaaagccc    2760
gccaccacat ttctgccacc cctgagcgag gcaaccacag caatgggata ccacctgaag    2820
accctgacac tgaacttcac catcagcaat ctgcagtatt ccccgatat gggcaagggc    2880
tctgccacct taacagcac agagggcgtg ctgcagcacc tgctgcggcc tctgttccag    2940
aagtcctcta tgggcccctt ctacctggga tgccagctga tctccctgcg gcccgaaaag    3000
gatggagcag caaccggagt ggataccaca tgtacatacc accctgaccc agtgggacca    3060
ggcctggata tccagcaatt atattgggaa ctgagtcagc tgacccacgg cgtgacacag    3120
ctgggcttct atgtgctgga cagggatagc ctgtttatca acggctacgc cccacagaat    3180
ctgtccatcc gcggcgagta tcagatcaac ttccacatcg tgaactggaa tctgagcaat    3240
cccgacccta ccagctccga gtacatcgcc ctgctgaggg acatccagga taaggtgacc    3300
acactgtata agggctccca gctgcacgac accttccgct tttgcctggt gaccaacctg    3360
acaatggatt ctatgctggt gacagtgaag gccctgttct ctagcaacct ggaccccagc    3420
ctggtggagc aggtgtttct ggataagacc ctgaatgcct cctctcactg gctgggcagc    3480
acctaccagc tggtggacat ccacgtgaca gagatggagc catccgtgta tcagcccacc    3540
agctcctcta gcacacagca cttctacctg aactttacca taactaatct gccctatagc    3600
caggatatcg cccagcctgg cacccacaaac taccagcgga acaagagaaa tatcgaggac    3660
```

-continued

```
gccctgaacc agctgttccg gaattcctct atcaagtctt atttcagcga ttgccaggtg    3720 tccacctta gatctgtgcc aaatagccac cacacaggcg tggactccct gtgcgccttt    3780
tctcccctgg caaggagggt ggatagggtg gcaatctacg aggagttcct gaggatgacc    3840
cgcgccggaa cacagctgca ggcctttacc ctggaccgga gctccgtgct ggtggatggc    3900
tattccccta acagaaatga gccactgaca ggcaactctg acctgccctt ctgggccatc    3960
atcctgatct gtctggcagg cctgctgggc ctgatcacct gcctgatctg tggctttctg    4020
gtgtgataa                                                             4029
```

<210> SEQ ID NO 8
<211> LENGTH: 1341
<212> TYPE: PRT
<213> ORGANISM: Artificial Sequence
<220> FEATURE:
<221> NAME/KEY: source
<223> OTHER INFORMATION: /note="Description of Artificial Sequence: Synthetic consensus MUC16 IRC Protein Sequence"

<400> SEQUENCE: 8

```
Met Asp Trp Thr Trp Ile Leu Phe Leu Val Ala Ala Thr Arg Val
1               5                   10                  15

His Ser Thr Ala Ala Gly Pro Leu Leu Val Pro Phe Thr Leu Asn Phe
                20                  25                  30

Thr Ile Thr Asn Leu Gln Tyr Glu Glu Asp Met His His Pro Gly Ser
            35                  40                  45

Arg Lys Phe Asn Thr Thr Glu Arg Val Leu Gln Gly Leu Leu Gly Pro
        50                  55                  60

Met Phe Lys Asn Thr Ser Val Gly Leu Leu Tyr Ser Gly Cys Arg Leu
65                  70                  75                  80

Thr Leu Leu Arg Ser Glu Lys Asp Gly Ala Ala Thr Gly Val Asp Ala
                85                  90                  95

Ile Cys Thr His Arg Leu Asp Pro Lys Ser Pro Gly Leu Asp Arg Glu
            100                 105                 110

Gln Leu Tyr Trp Glu Leu Ser Gln Leu Thr Asn Gly Ile Lys Glu Leu
        115                 120                 125

Gly Pro Tyr Thr Leu Asp Arg Asn Ser Leu Tyr Val Asn Gly Phe Thr
    130                 135                 140

His Arg Ser Ser Val Pro Asn Thr Ser Thr Pro Gly Thr Ser Thr Val
145                 150                 155                 160

Asp Leu Gly Thr Ser Gly Thr Pro Ser Ser Leu Pro Ser Pro Thr Ala
                165                 170                 175

Ala Gly Pro Leu Leu Val Pro Phe Thr Leu Asn Phe Thr Ile Thr Asn
            180                 185                 190

Leu Gln Tyr Glu Glu Asp Met Arg His Pro Gly Ser Arg Lys Phe Asn
        195                 200                 205

Thr Thr Glu Arg Val Leu Gln Gly Leu Leu Lys Pro Leu Phe Lys Asn
    210                 215                 220

Thr Ser Val Gly Pro Leu Tyr Ser Gly Cys Arg Leu Thr Leu Leu Arg
225                 230                 235                 240

Pro Glu Lys Asp Gly Ala Ala Thr Gly Val Asp Ala Ile Cys Thr His
                245                 250                 255

Arg Leu Asp Pro Lys Ser Pro Gly Leu Asn Arg Glu Gln Leu Tyr Trp
            260                 265                 270

Glu Leu Ser Lys Leu Thr Asn Gly Ile Thr Glu Leu Gly Pro Tyr Thr
        275                 280                 285
```

```
Leu Asp Arg Asn Ser Leu Tyr Val Asn Gly Phe Thr His Arg Thr Ser
            290                 295                 300
Val Pro Thr Thr Ser Thr Pro Gly Thr Ser Thr Val Asp Leu Gly Thr
305                 310                 315                 320
Ser Gly Thr Pro Phe Ser Leu Pro Ser Pro Thr Thr Ala Gly Pro Leu
                    325                 330                 335
Leu Val Pro Phe Thr Leu Asn Phe Thr Ile Thr Asn Leu Gln Tyr Glu
                340                 345                 350
Glu Asp Met His Arg Pro Gly Ser Arg Lys Phe Asn Thr Thr Glu Arg
            355                 360                 365
Val Leu Gln Gly Leu Leu Ser Pro Ile Phe Lys Asn Ser Ser Val Gly
        370                 375                 380
Pro Leu Tyr Ser Gly Cys Arg Leu Thr Ser Leu Arg Pro Glu Lys Asp
385                 390                 395                 400
Gly Ala Ala Thr Gly Met Asp Ala Val Cys Leu Tyr His Pro Asn Pro
                405                 410                 415
Lys Arg Pro Gly Leu Asp Arg Glu Gln Leu Tyr Trp Glu Leu Ser Gln
                420                 425                 430
Leu Thr His Asn Ile Thr Glu Leu Gly Pro Tyr Ser Leu Asp Arg Asp
            435                 440                 445
Ser Leu Tyr Val Asn Gly Phe Thr His Gln Asn Ser Val Pro Thr Thr
        450                 455                 460
Ser Thr Pro Gly Thr Ser Thr Val Tyr Trp Ala Thr Gly Thr Pro Thr
465                 470                 475                 480
Ser Ser Phe Pro Gly His Thr Ala Pro Gly Pro Leu Leu Ile Pro Phe
                485                 490                 495
Thr Leu Asn Phe Thr Ile Thr Asn Leu His Tyr Glu Glu Asn Met Gln
                500                 505                 510
His Pro Gly Ser Arg Lys Phe Asn Thr Thr Glu Arg Val Leu Gln Gly
            515                 520                 525
Leu Leu Lys Pro Leu Phe Lys Asn Thr Ser Val Gly Pro Leu Tyr Ser
        530                 535                 540
Gly Cys Arg Leu Thr Leu Leu Arg Pro Glu Lys His Gly Ala Ala Thr
545                 550                 555                 560
Gly Val Asp Ala Ile Cys Thr His Arg Leu Asp Pro Lys Gly Pro Gly
                565                 570                 575
Leu Asp Arg Glu Arg Leu Tyr Trp Glu Leu Ser Gln Leu Thr Asn Ser
                580                 585                 590
Ile Thr Glu Leu Gly Pro Tyr Thr Leu Asp Arg Asp Ser Leu Tyr Val
            595                 600                 605
Asn Gly Phe Asn Pro Arg Ser Ser Val Pro Thr Thr Ser Thr Pro Gly
        610                 615                 620
Thr Ser Thr Val His Leu Ala Thr Ser Gly Thr Pro Ser Ser Leu Pro
625                 630                 635                 640
Gly His Arg Gly Arg Lys Arg Arg Ser Ala Ala Ser His Leu Leu Ile
                645                 650                 655
Leu Phe Thr Leu Asn Phe Thr Ile Thr Asn Leu Arg Tyr Glu Glu Asn
                660                 665                 670
Met Trp Pro Gly Ser Arg Lys Phe Asn Thr Thr Glu Arg Val Leu Gln
            675                 680                 685
Gly Leu Leu Arg Pro Leu Phe Lys Asn Thr Ser Val Gly Pro Leu Tyr
        690                 695                 700
```

```
Ser Gly Ser Arg Leu Thr Leu Leu Arg Pro Glu Lys Asp Gly Glu Ala
705                 710                 715                 720

Thr Gly Val Asp Ala Ile Cys Thr His Arg Pro Asp Pro Thr Gly Pro
            725                 730                 735

Gly Leu Asp Arg Glu Gln Leu Tyr Leu Glu Leu Ser Gln Leu Thr His
                740                 745                 750

Ser Ile Thr Glu Leu Gly Pro Tyr Thr Leu Asp Arg Asp Ser Leu Tyr
        755                 760                 765

Val Asn Gly Phe Thr His Arg Ser Ser Val Pro Thr Thr Ser Thr Gly
    770                 775                 780

Val Val Ser Glu Glu Pro Phe Thr Leu Asn Phe Thr Ile Asn Asn Leu
785                 790                 795                 800

Arg Tyr Met Ala Asp Met Gly Gln Pro Gly Ser Leu Lys Phe Asn Ile
                805                 810                 815

Thr Asp Asn Val Met Lys His Leu Leu Ser Pro Leu Phe Gln Arg Ser
                820                 825                 830

Ser Leu Gly Ala Arg Tyr Thr Gly Cys Arg Val Ile Ala Leu Arg Ser
        835                 840                 845

Val Lys Asn Gly Ala Glu Thr Arg Val Asp Leu Leu Cys Thr Tyr Leu
    850                 855                 860

Gln Pro Leu Ser Gly Pro Gly Leu Pro Ile Lys Gln Val Phe His Glu
865                 870                 875                 880

Leu Ser Gln Gln Thr His Gly Ile Thr Arg Leu Gly Pro Tyr Ser Leu
                885                 890                 895

Asp Lys Asp Ser Leu Tyr Leu Asn Gly Tyr Asn Glu Pro Gly Leu Asp
            900                 905                 910

Glu Pro Pro Thr Thr Pro Lys Pro Ala Thr Thr Phe Leu Pro Pro Leu
            915                 920                 925

Ser Glu Ala Thr Thr Ala Met Gly Tyr His Leu Lys Thr Leu Thr Leu
    930                 935                 940

Asn Phe Thr Ile Ser Asn Leu Gln Tyr Ser Pro Asp Met Gly Lys Gly
945                 950                 955                 960

Ser Ala Thr Phe Asn Ser Thr Glu Gly Val Leu Gln His Leu Leu Arg
            965                 970                 975

Pro Leu Phe Gln Lys Ser Ser Met Gly Pro Phe Tyr Leu Gly Cys Gln
                980                 985                 990

Leu Ile Ser Leu Arg Pro Glu Lys Asp Gly Ala Ala Thr Gly Val Asp
            995                 1000                1005

Thr Thr Cys Thr Tyr His Pro Asp Pro Val Gly Pro Gly Leu Asp
    1010                1015                1020

Ile Gln Gln Leu Tyr Trp Glu Leu Ser Gln Leu Thr His Gly Val
    1025                1030                1035

Thr Gln Leu Gly Phe Tyr Val Leu Asp Arg Asp Ser Leu Phe Ile
    1040                1045                1050

Asn Gly Tyr Ala Pro Gln Asn Leu Ser Ile Arg Gly Glu Tyr Gln
    1055                1060                1065

Ile Asn Phe His Ile Val Asn Trp Asn Leu Ser Asn Pro Asp Pro
    1070                1075                1080

Thr Ser Ser Glu Tyr Ile Ala Leu Leu Arg Asp Ile Gln Asp Lys
    1085                1090                1095

Val Thr Thr Leu Tyr Lys Gly Ser Gln Leu His Asp Thr Phe Arg
    1100                1105                1110

Phe Cys Leu Val Thr Asn Leu Thr Met Asp Ser Met Leu Val Thr
```

```
            1115                1120               1125

Val Lys Ala Leu Phe Ser Ser Asn Leu Asp Pro Ser Leu Val Glu
            1130                1135               1140

Gln Val Phe Leu Asp Lys Thr Leu Asn Ala Ser Ser His Trp Leu
            1145                1150               1155

Gly Ser Thr Tyr Gln Leu Val Asp Ile His Val Thr Glu Met Glu
            1160                1165               1170

Pro Ser Val Tyr Gln Pro Thr Ser Ser Ser Thr Gln His Phe
            1175                1180               1185

Tyr Leu Asn Phe Thr Ile Thr Asn Leu Pro Tyr Ser Gln Asp Ile
            1190                1195               1200

Ala Gln Pro Gly Thr Thr Asn Tyr Gln Arg Asn Lys Arg Asn Ile
            1205                1210               1215

Glu Asp Ala Leu Asn Gln Leu Phe Arg Asn Ser Ser Ile Lys Ser
            1220                1225               1230

Tyr Phe Ser Asp Cys Gln Val Ser Thr Phe Arg Ser Val Pro Asn
            1235                1240               1245

Ser His His Thr Gly Val Asp Ser Leu Cys Ala Phe Ser Pro Leu
            1250                1255               1260

Ala Arg Arg Val Asp Arg Val Ala Ile Tyr Glu Glu Phe Leu Arg
            1265                1270               1275

Met Thr Arg Ala Gly Thr Gln Leu Gln Ala Phe Thr Leu Asp Arg
            1280                1285               1290

Ser Ser Val Leu Val Asp Gly Tyr Ser Pro Asn Arg Asn Glu Pro
            1295                1300               1305

Leu Thr Gly Asn Ser Asp Leu Pro Phe Trp Ala Ile Ile Leu Ile
            1310                1315               1320

Cys Leu Ala Gly Leu Leu Gly Leu Ile Thr Cys Leu Ile Cys Gly
            1325                1330               1335

Phe Leu Val
    1340

<210> SEQ ID NO 9
<211> LENGTH: 11
<212> TYPE: PRT
<213> ORGANISM: Homo sapiens

<400> SEQUENCE: 9

Asn Phe Ser Pro Leu Ala Arg Arg Val Asp Arg
1               5                   10

<210> SEQ ID NO 10
<211> LENGTH: 284
<212> TYPE: PRT
<213> ORGANISM: Homo sapiens

<400> SEQUENCE: 10

Ile Thr Leu Leu Arg Asp Ile Gln Asp Lys Val Thr Thr Leu Tyr Lys
1               5                   10                  15

Gly Ser Gln Leu His Asp Thr Phe Arg Phe Cys Leu Val Thr Asn Leu
                20                  25                  30

Thr Met Asp Ser Val Leu Val Thr Val Lys Ala Leu Phe Ser Ser Asn
                35                  40                  45

Leu Asp Pro Ser Leu Val Glu Gln Val Phe Leu Asp Lys Thr Leu Asn
                50                  55                  60

Ala Ser Phe His Trp Leu Gly Ser Thr Tyr Gln Leu Val Asp Ile His
```

```
                 65                  70                  75                  80
Val Thr Glu Met Glu Ser Ser Val Tyr Gln Pro Thr Ser Ser Ser Ser
                 85                  90                  95

Thr Gln His Phe Tyr Leu Asn Phe Thr Ile Thr Asn Leu Pro Tyr Ser
                100                 105                 110

Gln Asp Lys Ala Gln Pro Gly Thr Asn Tyr Gln Arg Asn Lys Arg
            115                 120                 125

Asn Ile Glu Asp Ala Leu Asn Gln Leu Phe Arg Asn Ser Ser Ile Lys
        130                 135                 140

Ser Tyr Phe Ser Asp Cys Gln Val Ser Thr Phe Arg Ser Val Pro Asn
145                 150                 155                 160

Arg His His Thr Gly Val Asp Ser Leu Cys Asn Phe Ser Pro Leu Ala
                165                 170                 175

Arg Arg Val Asp Arg Val Ala Ile Tyr Glu Glu Phe Leu Arg Met Thr
                180                 185                 190

Arg Asn Gly Thr Gln Leu Gln Asn Phe Thr Leu Asp Arg Ser Ser Val
                195                 200                 205

Leu Val Asp Gly Tyr Ser Pro Asn Arg Asn Glu Pro Leu Thr Gly Asn
        210                 215                 220

Ser Asp Leu Pro Phe Trp Ala Val Ile Leu Ile Gly Leu Ala Gly Leu
225                 230                 235                 240

Leu Gly Leu Ile Thr Cys Leu Ile Cys Gly Val Leu Val Thr Thr Arg
                245                 250                 255

Arg Arg Lys Lys Glu Gly Glu Tyr Asn Val Gln Gln Gln Cys Pro Gly
                260                 265                 270

Tyr Tyr Gln Ser His Leu Asp Leu Glu Asp Leu Gln
                275                 280

<210> SEQ ID NO 11
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ile Ala Leu Leu Arg Asp Ile Gln Asp Lys Val Thr Thr Leu Tyr Lys
1               5                  10                  15

Gly Ser Gln Leu His Asp Thr Phe Arg Phe Cys Leu Val Thr Asn Leu
                20                  25                  30

Thr Met Asp Ser Met Leu Val Thr Val Lys Ala Leu Phe Ser Ser Asn
            35                  40                  45

Leu Asp Pro Ser Leu Val Glu Gln Val Phe Leu Asp Lys Thr Leu Asn
        50                  55                  60

Ala Ser Ser His Trp Leu Gly Ser Thr Tyr Gln Leu Val Asp Ile His
65                  70                  75                  80

Val Thr Glu Met Glu Pro Ser Val Tyr Gln Pro Thr Ser Ser Ser Ser
                85                  90                  95

Thr Gln His Phe Tyr Leu Asn Phe Thr Ile Thr Asn Leu Pro Tyr Ser
                100                 105                 110

Gln Asp Ile Ala Gln Pro Gly Thr Thr Asn Tyr Gln Arg Asn Lys Arg
            115                 120                 125

Asn Ile Glu Asp Ala Leu Asn Gln Leu Phe Arg Asn Ser Ser Ile Lys
        130                 135                 140
```

```
Ser Tyr Phe Ser Asp Cys Gln Val Ser Thr Phe Arg Ser Val Pro Asn
145                 150                 155                 160

Ser His His Thr Gly Val Asp Ser Leu Cys Ala Phe Ser Pro Leu Ala
            165                 170                 175

Arg Arg Val Asp Arg Val Ala Ile Tyr Glu Glu Phe Leu Arg Met Thr
            180                 185                 190

Arg Ala Gly Thr Gln Leu Gln Ala Phe Thr Leu Asp Arg Ser Ser Val
            195                 200                 205

Leu Val Asp Gly Tyr Ser Pro Asn Arg Asn Glu Pro Leu Thr Gly Asn
            210                 215                 220

Ser Asp Leu Pro Phe Trp Ala Ile Ile Leu Ile Cys Leu Ala Gly Leu
225                 230                 235                 240

Leu Gly Leu Ile Thr Cys Leu Ile Cys Gly Phe Leu Val
            245                 250
```

<210> SEQ ID NO 12
<211> LENGTH: 253
<212> TYPE: PRT
<213> ORGANISM: Homo sapiens

<400> SEQUENCE: 12

```
Ile Thr Leu Leu Arg Asp Ile Gln Asp Lys Val Thr Thr Leu Tyr Lys
1               5                   10                  15

Gly Ser Gln Leu His Asp Thr Phe Arg Phe Cys Leu Val Thr Asn Leu
            20                  25                  30

Thr Met Asp Ser Val Leu Val Thr Val Lys Ala Leu Phe Ser Ser Asn
            35                  40                  45

Leu Asp Pro Ser Leu Val Glu Gln Val Phe Leu Asp Lys Thr Leu Asn
50                  55                  60

Ala Ser Phe His Trp Leu Gly Ser Thr Tyr Gln Leu Val Asp Ile His
65                  70                  75                  80

Val Thr Glu Met Glu Ser Ser Val Tyr Gln Pro Thr Ser Ser Ser Ser
                85                  90                  95

Thr Gln His Phe Tyr Leu Asn Phe Thr Ile Thr Asn Leu Pro Tyr Ser
            100                 105                 110

Gln Asp Lys Ala Gln Pro Gly Thr Thr Asn Tyr Gln Arg Asn Lys Arg
            115                 120                 125

Asn Ile Glu Asp Ala Leu Asn Gln Leu Phe Arg Asn Ser Ser Ile Lys
130                 135                 140

Ser Tyr Phe Ser Asp Cys Gln Val Ser Thr Phe Arg Ser Val Pro Asn
145                 150                 155                 160

Arg His His Thr Gly Val Asp Ser Leu Cys Asn Phe Ser Pro Leu Ala
            165                 170                 175

Arg Arg Val Asp Arg Val Ala Ile Tyr Glu Glu Phe Leu Arg Met Thr
            180                 185                 190

Arg Asn Gly Thr Gln Leu Gln Asn Phe Thr Leu Asp Arg Ser Ser Val
            195                 200                 205

Leu Val Asp Gly Tyr Ser Pro Asn Arg Asn Glu Pro Leu Thr Gly Asn
            210                 215                 220

Ser Asp Leu Pro Phe Trp Ala Val Ile Leu Ile Gly Leu Ala Gly Leu
225                 230                 235                 240

Leu Gly Leu Ile Thr Cys Leu Ile Cys Gly Val Leu Val
            245                 250
```

CANCER VACCINES TARGETING MUC16 AND USES THEREOF

CROSS-REFERENCE TO RELATED APPLICATIONS

This application is a divisional of U.S. patent application Ser. No. 16/219,460 filed Dec. 13, 2018, which claims the benefit of U.S. Provisional Patent Application Nos. 62/598,314 filed Dec. 13, 2017 and 62/599,513 filed Dec. 15, 2017, the disclosures of which are incorporated herein by reference in their entireties.

SEQUENCE LISTING

This application contains a Sequence Listing which has been submitted electronically in ASCII format and is hereby incorporated by reference in its entirety. Said ASCII copy, created Dec. 20, 2021, is named 104409_000660 sequence_listing.txt and is 61,653 bytes in size.

TECHNICAL FIELD

The present invention relates to MUC16 antigens and nucleic acid molecules which encode the same. The present invention also relates to vaccines including the MUC16 antigens and/or nucleic acid molecules. The present invention further relates to methods of using the vaccines for inducing immune responses and preventing and/or treating subjects having MUC16-expressing cancerous cells.

BACKGROUND

Cancer remains a major cause of death in the U.S. and worldwide. The cancer vaccine market is growing rapidly. Effective tumor vaccines may be useful to prevent tumor growth and/or may be useful as being a more effective, less toxic alternative to standard treatments for patients with advanced cancers. An antigen associated with cancer and, therefore, a target for anti-tumor vaccines is MUC16.

MUC16 is a member of the mucin family of high molecular weight glycoproteins. Mucins are expressed by specialized epithelial cells surrounding the luminal surface of various organs of the respiratory, gastrointestinal and reproductive tracts. MUC16 has direct and indirect roles in the maintenance of epithelial integrity and the lubrication and protection of epithelial surfaces.

The tandem repeat domain of MUC16 contains a repeating peptide epitope, CA125, which has become the gold-standard biomarker for multiple clinical scenarios that occur throughout diagnosis and treatment of ovarian cancer, including: 1) screening for early detection, 2) distinguishing between benign and malignant disease in pre- and post-menopausal women presenting with pelvic masses, and 3) monitoring response to therapy. Additionally, functional studies have shown that MUC16 contributes to the transformation and metastasis of ovarian tumors.

Because of its high expression in the majority of ovarian cancers as well as its putative role in potentiating tumorigenesis, MUC16 is an attractive cancer therapeutic vaccine target. However, antigen design is impacted by its large size, complex glycosylation profile, and expression in healthy epithelial tissue.

Vaccines for the treatment and prevention of cancer are of great interest. Existing vaccines targeting tumor cell antigens are often limited by poor antigen expression in vivo. Accordingly, a need remains in the art for the development of safe and effective vaccines that are applicable to tumors expressing MUC16, thereby providing treatment of and promoting survival of subjects afflicted with such cancers.

SUMMARY OF THE INVENTION

Provided herein are nucleic acid molecules comprising one or more nucleic acid sequences selected from the group consisting of: (a) a nucleic acid sequence that encodes amino acids 19-1490 of SEQ ID NO: 2; (b) a nucleic acid sequence that encodes a fragment comprising at least 90% of an entire length of a protein comprising amino acids 19-1490 of SEQ ID NO: 2; (c) a nucleic acid sequence that encodes a protein that is at least 95% identical to amino acids 19-1490 of SEQ ID NO: 2; and (d) a nucleic acid sequence that encodes a fragment comprising at least 90% of an entire length of a protein that is at least 95% identical to amino acids 19-1490 of SEQ ID NO: 2.

Also provided herein are nucleic acid molecules comprising one or more nucleic acid sequences selected from the group consisting of: nucleotides 55-4470 of SEQ ID NO: 1; (b) a fragment comprising at least 90% of an entire length of a nucleic acid molecule comprising nucleotides 55-4470 of SEQ ID NO: 1; (c) a fragment that is at least 95% identical to nucleotides 55-4470 of SEQ ID NO: 1; and (d) a fragment comprising at least 90% of an entire length of a nucleic acid sequence that is at least 95% identical to nucleotides 55-4470 of SEQ ID NO: 1.

Provided herein are nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 95% identical to SEQ ID NO: 2; and (d) a nucleic acid sequence that encodes a fragment comprising at least 90% of an entire length of a protein that is at least 95% identical to SEQ ID NO: 2.

Also provided herein are nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 95% identical to SEQ ID NO: 1; and (d) a fragment comprising at least 90% of an entire length of a nucleic acid sequence that is at least 95% identical to SEQ ID NO: 1. In some embodiments, the nucleic acid molecule comprises the nucleic acid sequence set forth in SEQ ID NO: 1.

Provided herein are nucleic acid molecules comprising one or more nucleic acid sequences selected from the group consisting of: (a) a nucleic acid sequence that encodes amino acids 19-642 of SEQ ID NO: 4; (b) a nucleic acid sequence that encodes a fragment comprising at least 90% of an entire length of a protein comprising amino acids 19-642 of SEQ ID NO: 4; (c) a nucleic acid sequence that encodes a protein that is at least 95% identical to amino acids 19-642 of SEQ ID NO: 4; and (d) a nucleic acid sequence that encodes a fragment comprising at least 90% of an entire length of a protein that is at least 95% identical to amino acids 19-642 of SEQ ID NO: 4.

Also provided herein are nucleic acid molecules comprising one or more nucleic acid sequences selected from the group consisting of: nucleotides 55-1926 of SEQ ID NO: 3; (b) a fragment comprising at least 90% of an entire length of a nucleic acid molecule comprising nucleotides 55-1926 of SEQ ID NO: 3; (c) a fragment that is at least 95% identical to nucleotides 55-1926 of SEQ ID NO: 3; and (d) a fragment comprising at least 90% of an entire length of a nucleic acid sequence that is at least 95% identical to nucleotides 55-1926 of SEQ ID NO: 3.

Provided herein are nucleic acid molecules comprising one or more nucleic acid sequences selected from the group consisting of: (a) a nucleic acid sequence that encodes SEQ ID NO: 4; (b) a nucleic acid sequence that encodes a fragment comprising at least 90% of an entire length of SEQ ID NO: 4; (c) a nucleic acid sequence that encodes a protein that is at least 95% identical to SEQ ID NO: 4; and (d) a nucleic acid sequence that encodes a fragment comprising at least 90% of an entire length of a protein that is at least 95% identical to SEQ ID NO: 4.

Also provided herein are nucleic acid molecules comprising one or more nucleic acid sequences selected from the group consisting of: (a) SEQ ID NO: 3; (b) a fragment comprising at least 90% of an entire length of SEQ ID NO: 3; (c) a fragment that is at least 95% identical to SEQ ID NO: 3; and (d) a fragment comprising at least 90% of an entire length of a nucleic acid sequence that is at least 95% identical to SEQ ID NO: 3. In some embodiments, the nucleic acid molecule comprises the nucleic acid sequence set forth in SEQ ID NO: 3.

Provided herein are nucleic acid molecules comprising one or more nucleic acid sequences selected from the group consisting of: (a) a nucleic acid sequence that encodes amino acids 19-710 of SEQ ID NO: 6; (b) a nucleic acid sequence that encodes a fragment comprising at least 90% of an entire length of a protein comprising amino acids 19-710 of SEQ ID NO: 6; (c) a nucleic acid sequence that encodes a protein that is at least 95% identical to amino acids 19-710 of SEQ ID NO: 6; and (d) a nucleic acid sequence that encodes a fragment comprising at least 90% of an entire length of a protein that is at least 95% identical to amino acids 19-710 of SEQ ID NO: 6.

Also provided herein are nucleic acid molecules comprising one or more nucleic acid sequences selected from the group consisting of: nucleotides 55-2130 of SEQ ID NO: 5; (b) a fragment comprising at least 90% of an entire length of a nucleic acid molecule comprising nucleotides 55-2130 of SEQ ID NO: 5; (c) a fragment that is at least 95% identical to nucleotides 55-2130 of SEQ ID NO: 5; and (d) a fragment comprising at least 90% of an entire length of a nucleic acid sequence that is at least 95% identical to nucleotides 55-2130 of SEQ ID NO: 5.

Provided herein are nucleic acid molecules comprising one or more nucleic acid sequences selected from the group consisting of: (a) a nucleic acid sequence that encodes SEQ ID NO: 6; (b) a nucleic acid sequence that encodes a fragment comprising at least 90% of an entire length of SEQ ID NO: 6; (c) a nucleic acid sequence that encodes a protein that is at least 95% identical to SEQ ID NO: 6; and (d) a nucleic acid sequence that encodes a fragment comprising at least 90% of an entire length of a protein that is at least 95% identical to SEQ ID NO: 6.

Also provided herein are nucleic acid molecules comprising one or more nucleic acid sequences selected from the group consisting of: (a) SEQ ID NO: 5; (b) a fragment comprising at least 90% of an entire length of SEQ ID NO: 5; (c) a fragment that is at least 95% identical to SEQ ID NO: 5; and (d) a fragment comprising at least 90% of an entire length of a nucleic acid sequence that is at least 95% identical to SEQ ID NO: 5. In some embodiments, the nucleic acid molecule comprises the nucleic acid sequence set forth in SEQ ID NO: 5.

Provided herein are nucleic acid molecules comprising one or more nucleic acid sequences selected from the group consisting of: (a) a nucleic acid sequence that encodes amino acids 19-642 and 650-1341 of SEQ ID NO: 8; (b) a nucleic acid sequence that encodes a fragment comprising at least 90% of an entire length of a protein comprising amino acids 19-642 and 650-1341 of SEQ ID NO: 8; (c) a nucleic acid sequence that encodes a protein that is at least 95% identical to amino acids 19-642 and 650-1341 of SEQ ID NO: 8; and (d) a nucleic acid sequence that encodes a fragment comprising at least 90% of an entire length of a protein that is at least 95% identical to amino acids 19-642 and 650-1341 of SEQ ID NO: 8.

Also provided herein are nucleic acid molecules comprising one or more nucleic acid sequences selected from the group consisting of: nucleotides 55-1926 and 1948-4023 of SEQ ID NO: 7; (b) a fragment comprising at least 90% of an entire length of a nucleic acid molecule comprising nucleotides 55-1926 and 1948-4023 of SEQ ID NO: 7; (c) a fragment that is at least 95% identical to nucleotides 55-1926 and 1948-4023 of SEQ ID NO: 7; and (d) a fragment comprising at least 90% of an entire length of a nucleic acid sequence that is at least 95% identical to nucleotides 55-1926 and 1948-4023 of SEQ ID NO: 7.

Provided herein are nucleic acid molecules comprising one or more nucleic acid sequences selected from the group consisting of: (a) a nucleic acid sequence that encodes amino acids 19-1341 of SEQ ID NO: 8; (b) a nucleic acid sequence that encodes a fragment comprising at least 90% of an entire length of a protein comprising amino acids 19-1341 of SEQ ID NO: 8; (c) a nucleic acid sequence that encodes a protein that is at least 95% identical to amino acids 19-1341 of SEQ ID NO: 8; and (d) a nucleic acid sequence that encodes a fragment comprising at least 90% of an entire length of a protein that is at least 95% identical to amino acids 19-1341 of SEQ ID NO: 8.

Also provided herein are nucleic acid molecules comprising one or more nucleic acid sequences selected from the group consisting of: nucleotides 55-4023 of SEQ ID NO: 7; (b) a fragment comprising at least 90% of an entire length of a nucleic acid molecule comprising nucleotides 55-4023 of SEQ ID NO: 7; (c) a fragment that is at least 95% identical to nucleotides 55-4023 of SEQ ID NO: 7; and (d) a fragment comprising at least 90% of an entire length of a nucleic acid sequence that is at least 95% identical to nucleotides 55-4023 of SEQ ID NO: 7.

Provided herein are nucleic acid molecules comprising one or more nucleic acid sequences selected from the group consisting of: (a) a nucleic acid sequence that encodes SEQ ID NO: 8; (b) a nucleic acid sequence that encodes a fragment comprising at least 90% of an entire length of SEQ ID NO: 8; (c) a nucleic acid sequence that encodes a protein that is at least 95% identical to SEQ ID NO: 8; and (d) a nucleic acid sequence that encodes a fragment comprising at least 90% of an entire length of a protein that is at least 95% identical to SEQ ID NO: 8.

Also provided herein are nucleic acid molecules comprising one or more nucleic acid sequences selected from the group consisting of: (a) SEQ ID NO: 7; (b) a fragment comprising at least 90% of an entire length of SEQ ID NO: 7; (c) a fragment that is at least 95% identical to SEQ ID NO: 7; and (d) a fragment comprising at least 90% of an entire length of a nucleic acid sequence that is at least 95% identical to SEQ ID NO: 7. In some embodiments, the nucleic acid molecule comprises the nucleic acid sequence set forth in SEQ ID NO: 7.

One or more of the nucleic acid molecules described herein may be incorporated into a vector, such as a plasmid or viral vector. In some embodiments, the vector comprises nucleic acid molecules comprising one or more nucleic acid sequences selected from the group consisting of: (a) a nucleic acid sequence that encodes amino acids 19-1490 of SEQ ID NO: 2; (b) a nucleic acid sequence that encodes a fragment comprising at least 90% of an entire length of a protein comprising amino acids 19-1490 of SEQ ID NO: 2; (c) a nucleic acid sequence that encodes a protein that is at least 95% identical to amino acids 19-1490 of SEQ ID NO: 2; and (d) a nucleic acid sequence that encodes a fragment comprising at least 90% of an entire length of a protein that is at least 95% identical to amino acids 19-1490 of SEQ ID NO: 2. In certain embodiments, the vector comprises, nucleic acid molecules comprising one or more nucleic acid sequences selected from the group consisting of: nucleotides 55-4470 of SEQ ID NO: 1; (b) a fragment comprising at least 90% of an entire length of a nucleic acid molecule comprising nucleotides 55-4470 of SEQ ID NO: 1; (c) a fragment that is at least 95% identical to nucleotides 55-4470 of SEQ ID NO: 1; and (d) a fragment comprising at least 90% of an entire length of a nucleic acid sequence that is at least 95% identical to nucleotides 55-4470 of SEQ ID NO: 1. In further embodiments, the vector comprises nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 95% identical to SEQ ID NO: 2; and (d) a nucleic acid sequence that encodes a fragment comprising at least 90% of an entire length of a protein that is at least 95% identical to SEQ ID NO: 2. In still further embodiments, the vector comprises nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 95% identical to SEQ ID NO: 1; and (d) a fragment comprising at least 90% of an entire length of a nucleic acid sequence that is at least 95% identical to SEQ ID NO: 1. In some embodiments, the nucleic acid molecule comprises the nucleic acid sequence set forth in SEQ ID NO: 1.

In further embodiments, the vector comprises one or more nucleic acid sequences selected from the group consisting of: (a) a nucleic acid sequence that encodes amino acids 19-642 of SEQ ID NO: 4; (b) a nucleic acid sequence that encodes a fragment comprising at least 90% of an entire length of a protein comprising amino acids 19-642 of SEQ ID NO: 4; (c) a nucleic acid sequence that encodes a protein that is at least 95% identical to amino acids 19-642 of SEQ ID NO: 4; and (d) a nucleic acid sequence that encodes a fragment comprising at least 90% of an entire length of a protein that is at least 95% identical to amino acids 19-642 of SEQ ID NO: 4. In certain embodiments, the vector comprises nucleic acid molecules comprising one or more nucleic acid sequences selected from the group consisting of: nucleotides 55-1926 of SEQ ID NO: 3; (b) a fragment comprising at least 90% of an entire length of a nucleic acid molecule comprising nucleotides 55-1926 of SEQ ID NO: 3; (c) a fragment that is at least 95% identical to nucleotides 55-1926 of SEQ ID NO: 3; and (d) a fragment comprising at least 90% of an entire length of a nucleic acid sequence that is at least 95% identical to nucleotides 55-1926 of SEQ ID NO: 3. In some embodiments, the vector comprises nucleic acid molecules comprising one or more nucleic acid sequences selected from the group consisting of: (a) a nucleic acid sequence that encodes SEQ ID NO: 4; (b) a nucleic acid sequence that encodes a fragment comprising at least 90% of an entire length of SEQ ID NO: 4; (c) a nucleic acid sequence that encodes a protein that is at least 95% identical to SEQ ID NO: 4; and (d) a nucleic acid sequence that encodes a fragment comprising at least 90% of an entire length of a protein that is at least 95% identical to SEQ ID NO: 4. In further embodiments, the vector comprises nucleic acid molecules comprising one or more nucleic acid sequences selected from the group consisting of: (a) SEQ ID NO: 3; (b) a fragment comprising at least 90% of an entire length of SEQ ID NO: 3; (c) a fragment that is at least 95% identical to SEQ ID NO: 3; and (d) a fragment comprising at least 90% of an entire length of a nucleic acid sequence that is at least 95% identical to SEQ ID NO: 3. In some embodiments, the nucleic acid molecule comprises the nucleic acid sequence set forth in SEQ ID NO: 3.

In some embodimetns, the vector comprises nucleic acid molecules comprising one or more nucleic acid sequences selected from the group consisting of: (a) a nucleic acid sequence that encodes amino acids 19-710 of SEQ ID NO: 6; (b) a nucleic acid sequence that encodes a fragment comprising at least 90% of an entire length of a protein comprising amino acids 19-710 of SEQ ID NO: 6; (c) a nucleic acid sequence that encodes a protein that is at least 95% identical to amino acids 19-710 of SEQ ID NO: 6; and (d) a nucleic acid sequence that encodes a fragment comprising at least 90% of an entire length of a protein that is at least 95% identical to amino acids 19-710 of SEQ ID NO: 6. In certain embodiments, the vector comprises nucleic acid molecules comprising one or more nucleic acid sequences selected from the group consisting of: nucleotides 55-2130 of SEQ ID NO: 5; (b) a fragment comprising at least 90% of an entire length of a nucleic acid molecule comprising nucleotides 55-2130 of SEQ ID NO: 5; (c) a fragment that is at least 95% identical to nucleotides 55-2130 of SEQ ID NO: 5; and (d) a fragment comprising at least 90% of an entire length of a nucleic acid sequence that is at least 95% identical to nucleotides 55-2130 of SEQ ID NO: 5. In further embodiments, the vector comprises nucleic acid molecules comprising one or more nucleic acid sequences selected from the group consisting of: (a) a nucleic acid sequence that encodes SEQ ID NO: 6; (b) a nucleic acid sequence that encodes a fragment comprising at least 90% of an entire length of SEQ ID NO: 6; (c) a nucleic acid sequence that encodes a protein that is at least 95% identical to SEQ ID NO: 6; and (d) a nucleic acid sequence that encodes a fragment comprising at least 90% of an entire length of a protein that is at least 95% identical to SEQ ID NO: 6. In still further embodiments, the vector comprises nucleic acid molecules comprising one or more nucleic acid sequences selected from the group consisting of: (a) SEQ ID NO: 5; (b) a fragment comprising at least 90% of an entire length of SEQ ID NO: 5; (c) a fragment that is at least 95% identical to SEQ ID NO: 5; and (d) a fragment comprising at least 90% of an entire length of a nucleic acid sequence that is at least 95% identical to SEQ ID NO: 5. In some embodiments, the nucleic acid molecule comprises the nucleic acid sequence set forth in SEQ ID NO: 5.

In further embodiments, the vector comprises nucleic acid molecules comprising one or more nucleic acid sequences selected from the group consisting of: (a) a nucleic acid sequence that encodes amino acids 19-642 and 650-1341 of SEQ ID NO: 8; (b) a nucleic acid sequence that encodes a fragment comprising at least 90% of an entire length of a protein comprising amino acids 19-642 and 650-1341 of SEQ ID NO: 8; (c) a nucleic acid sequence that encodes a protein that is at least 95% identical to amino acids 19-642 and 650-1341 of SEQ ID NO: 8; and (d) a nucleic acid sequence that encodes a fragment comprising at least 90% of an entire length of a protein that is at least 95% identical to amino acids 19-642 and 650-1341 of SEQ ID NO: 8. In certain embodiments, the vector comprises nucleic acid molecules comprising one or more nucleic acid sequences selected from the group consisting of: nucleotides 55-1926 and 1948-4023 of SEQ ID NO: 7; (b) a fragment comprising at least 90% of an entire length of a nucleic acid molecule comprising nucleotides 55-1926 and 1948-4023 of SEQ ID NO: 7; (c) a fragment that is at least 95% identical to nucleotides 55-1926 and 1948-4023 of SEQ ID NO: 7; and (d) a fragment comprising at least 90% of an entire length of a nucleic acid sequence that is at least 95% identical to nucleotides 55-1926 and 1948-4023 of SEQ ID NO: 7. In further embodiments, the vector comprises nucleic acid molecules comprising one or more nucleic acid sequences selected from the group consisting of: (a) a nucleic acid sequence that encodes amino acids 19-1341 of SEQ ID NO: 8; (b) a nucleic acid sequence that encodes a fragment comprising at least 90% of an entire length of a protein comprising amino acids 19-1341 of SEQ ID NO: 8; (c) a nucleic acid sequence that encodes a protein that is at least 95% identical to amino acids 19-1341 of SEQ ID NO: 8; and (d) a nucleic acid sequence that encodes a fragment comprising at least 90% of an entire length of a protein that is at least 95% identical to amino acids 19-1341 of SEQ ID NO: 8. In certain embodiments, the vector comprises nucleic acid molecules comprising one or more nucleic acid sequences selected from the group consisting of: nucleotides 55-4023 of SEQ ID NO: 7; (b) a fragment comprising at least 90% of an entire length of a nucleic acid molecule comprising nucleotides 55-4023 of SEQ ID NO: 7; (c) a fragment that is at least 95% identical to nucleotides 55-4023 of SEQ ID NO: 7; and (d) a fragment comprising at least 90% of an entire length of a nucleic acid sequence that is at least 95% identical to nucleotides 55-4023 of SEQ ID NO: 7. In some embodiments, the vector comprises nucleic acid molecules comprising one or more nucleic acid sequences selected from the group consisting of: (a) a nucleic acid sequence that encodes SEQ ID NO: 8; (b) a nucleic acid sequence that encodes a fragment comprising at least 90% of an entire length of SEQ ID NO: 8; (c) a nucleic acid sequence that encodes a protein that is at least 95% identical to SEQ ID NO: 8; and (d) a nucleic acid sequence that encodes a fragment comprising at least 90% of an entire length of a protein that is at least 95% identical to SEQ ID NO: 8. IN some embodiments, the vector comprises nucleic acid molecules comprising one or more nucleic acid sequences selected from the group consisting of: (a) SEQ ID NO: 7; (b) a fragment comprising at least 90% of an entire length of SEQ ID NO: 7; (c) a fragment that is at least 95% identical to SEQ ID NO: 7; and (d) a fragment comprising at least 90% of an entire length of a nucleic acid sequence that is at least 95% identical to SEQ ID NO: 7. In some embodiments, the nucleic acid molecule comprises the nucleic acid sequence set forth in SEQ ID NO: 7.

In some embodiments, the nucleic acids described herein are operably linked to a regulatory element. In some embodiments the regulatory element is a promoter and/or a poly-adenylation signal. In further embodiments, the promoter is a human cytomegalovirus immediate-early promoter (hCMV promoter). In still further embodiments, the poly-adenylation signal is a bovine growth hormone poly-adenylation signal (bGH polyA).

Also provided herein are compositions comprising one or more nucleic acid molecules as described herein. In some embodiments, the compositions comprise a pharmaceutically acceptable carrier.

Further provided are MUC16 antigenic proteins comprising the amino acid sequence selected from the group consisting of: (a) amino acids 19-1490 of SEQ ID NO: 2; (b) a fragment comprising at least 90% of an entire length of a protein comprising amino acids 19-1490 of SEQ ID NO: 2; (c) an amino acid sequence that is at least 95% identical to amino acids 19-1490 of SEQ ID NO: 2; and (d) a fragment comprising at least 90% of an entire length of an amino acid sequence that is at least 95% identical to amino acids 19-1490 of SEQ ID NO: 2.

Further provided are MUC16 antigenic proteins comprising the amino acid sequence selected from the group consisting of: (a) SEQ ID NO: 2; (b) a fragment comprising at least 90% of an entire length of SEQ ID NO: 2; (c) an amino acid sequence that is at least 95% identical to SEQ ID NO: 2; and (c) a fragment comprising at least 90% of an entire length of an amino acid sequence that is at least 95% identical to SEQ ID NO: 2. In some embodiments, the protein comprises the amino acid sequence set forth in SEQ ID NO: 2.

Further provided are MUC16 antigenic proteins comprising the amino acid sequence selected from the group consisting of: (a) amino acids 19-642 of SEQ ID NO: 4; (b) a fragment comprising at least 90% of an entire length of a protein comprising amino acids 19-642 of SEQ ID NO: 4; (c) an amino acid sequence that is at least 95% identical to amino acids 19-642 of SEQ ID NO: 4; and (d) a fragment comprising at least 90% of an entire length of an amino acid sequence that is at least 95% identical to amino acids 19-642 of SEQ ID NO: 4.

Further provided are MUC16 antigenic proteins comprising the amino acid sequence selected from the group consisting of: (a) SEQ ID NO: 4; (b) a fragment comprising at least 90% of an entire length of SEQ ID NO: 4; (c) an amino acid sequence that is at least 95% identical to SEQ ID NO: 4; and (c) a fragment comprising at least 90% of an entire length of an amino acid sequence that is at least 95% identical to SEQ ID NO: 4. In some embodiments, the protein comprises the amino acid sequence set forth in SEQ ID NO: 2.

Further provided are MUC16 antigenic proteins comprising the amino acid sequence selected from the group consisting of: (a) amino acids 19-710 of SEQ ID NO: 6; (b) a fragment comprising at least 90% of an entire length of a protein comprising amino acids 19-710 of SEQ ID NO: 6; (c) an amino acid sequence that is at least 95% identical to amino acids 19-710 of SEQ ID NO: 6; and (d) a fragment comprising at least 90% of an entire length of an amino acid sequence that is at least 95% identical to amino acids 19-710 of SEQ ID NO: 6.

Further provided are MUC16 antigenic proteins comprising the amino acid sequence selected from the group consisting of: (a) SEQ ID NO: 6; (b) a fragment comprising at least 90% of an entire length of SEQ ID NO: 6; (c) an amino acid sequence that is at least 95% identical to SEQ ID NO: 6; and (c) a fragment comprising at least 90% of an entire length of an amino acid sequence that is at least 95% identical to SEQ ID NO: 6. In some embodiments, the protein comprises the amino acid sequence set forth in SEQ ID NO: 6.

Further provided are MUC16 antigenic proteins comprising the amino acid sequence selected from the group consisting of: (a) amino acids 19-642 and 650-1341 of SEQ ID NO: 8; (b) a fragment comprising at least 90% of an entire length of a protein comprising amino acids 19-642 and 650-1341 of SEQ ID NO: 8; (c) an amino acid sequence that is at least 95% identical to amino acids 19-642 and 650-1341 of SEQ ID NO: 8; and (d) a fragment comprising at least 90% of an entire length of an amino acid sequence that is at least 95% identical to amino acids 19-642 and 650-1341 of SEQ ID NO: 8.

Further provided are MUC16 antigenic proteins comprising the amino acid sequence selected from the group consisting of: (a) amino acids 19-1341 of SEQ ID NO: 8; (b) a fragment comprising at least 90% of an entire length of a protein comprising amino acids 19-1341 of SEQ ID NO: 8; (c) an amino acid sequence that is at least 95% identical to amino acids 19-1341 of SEQ ID NO: 8; and (d) a fragment comprising at least 90% of an entire length of an amino acid sequence that is at least 95% identical to amino acids 19-1341 of SEQ ID NO: 8.

Further provided are MUC16 antigenic proteins comprising the amino acid sequence selected from the group consisting of: (a) SEQ ID NO: 8; (b) a fragment comprising at least 90% of an entire length of SEQ ID NO: 8; (c) an amino acid sequence that is at least 95% identical to SEQ ID NO: 8; and (c) a fragment comprising at least 90% of an entire length of an amino acid sequence that is at least 95% identical to SEQ ID NO: 8. In some embodiments, the protein comprises the amino acid sequence set forth in SEQ ID NO: 8.

Vaccines comprising a MUC16 antigen, wherein the antigen comprises the amino acid sequence set forth in SEQ ID NO: 2 are also provided. In some embodiments, the antigen is encoded by SEQ ID NO: 1.

Vaccines comprising a MUC16 antigen, wherein the antigen comprises the amino acid sequence set forth in SEQ ID NO: 4 are also provided. In some embodiments, the antigen is encoded by SEQ ID NO: 3.

Vaccines comprising a MUC16 antigen, wherein the antigen comprises the amino acid sequence set forth in SEQ ID NO: 6 are also provided. In some embodiments, the antigen is encoded by SEQ ID NO: 5.

Vaccines comprising a MUC16 antigen, wherein the antigen comprises the amino acid sequence set forth in SEQ ID NO: 8 are also provided. In some embodiments, the antigen is encoded by SEQ ID NO: 7.

Further provided are vaccines comprising a nucleic acid molecule wherein the nucleic acid molecule comprises a nucleic acid sequence having at least about 95% identity over an entire length of the nucleic acid sequence set forth in SEQ ID NO: 1. Further disclosed herein are vaccines comprising a nucleic acid molecule wherein the nucleic acid molecule encodes a MUC16 antigen comprising an amino acid sequence having at least about 95% identity over an entire length of the amino acid sequence set forth in SEQ ID NO: 2.

Further provided are vaccines comprising a nucleic acid molecule wherein the nucleic acid molecule comprises a nucleic acid sequence having at least about 95% identity over an entire length of the nucleic acid sequence set forth in SEQ ID NO: 3. Further disclosed herein are vaccines comprising a nucleic acid molecule wherein the nucleic acid molecule encodes a MUC16 antigen comprising an amino acid sequence having at least about 95% identity over an entire length of the amino acid sequence set forth in SEQ ID NO: 4.

Further provided are vaccines comprising a nucleic acid molecule wherein the nucleic acid molecule comprises a nucleic acid sequence having at least about 95% identity over an entire length of the nucleic acid sequence set forth in SEQ ID NO: 5. Further disclosed herein are vaccines comprising a nucleic acid molecule wherein the nucleic acid molecule encodes a MUC16 antigen comprising an amino acid sequence having at least about 95% identity over an entire length of the amino acid sequence set forth in SEQ ID NO: 6.

Further provided are vaccines comprising a nucleic acid molecule wherein the nucleic acid molecule comprises a nucleic acid sequence having at least about 95% identity over an entire length of the nucleic acid sequence set forth in SEQ ID NO: 7. Further disclosed herein are vaccines comprising a nucleic acid molecule wherein the nucleic acid molecule encodes a MUC16 antigen comprising an amino acid sequence having at least about 95% identity over an entire length of the amino acid sequence set forth in SEQ ID NO: 8.

In some embodiments, the nucleic acid molecule may comprise an expression vector. The vaccines may further comprise a pharmaceutically acceptable excipient. In some embodiments, the vaccines may further comprise an adjuvant. In certain embodiments, the adjuvant is IL-12, IL-15, IL-28, or RANTES.

Also provided herein are vaccines comprising a MUC16 antigen, wherein the antigen comprises an amino acid sequence having set forth in SEQ ID NO: 2. In some embodiments, the antigen is encoded by SEQ ID NO: 1.

Further provided are vaccines comprising a peptide, wherein the peptide comprises an amino acid sequence having at least about 90% identity over an entire length of the amino acid sequence set forth in SEQ ID NO: 2.

Also provided herein are vaccines comprising a MUC16 antigen, wherein the antigen comprises an amino acid sequence having set forth in SEQ ID NO: 4. In some embodiments, the antigen is encoded by SEQ ID NO: 3.

Further provided are vaccines comprising a peptide, wherein the peptide comprises an amino acid sequence having at least about 90% identity over an entire length of the amino acid sequence set forth in SEQ ID NO: 4.

Also provided herein are vaccines comprising a MUC16 antigen, wherein the antigen comprises an amino acid sequence having set forth in SEQ ID NO: 6. In some embodiments, the antigen is encoded by SEQ ID NO: 5.

Further provided are vaccines comprising a peptide, wherein the peptide comprises an amino acid sequence having at least about 90% identity over an entire length of the amino acid sequence set forth in SEQ ID NO: 6.

Also provided herein are vaccines comprising a MUC16 antigen, wherein the antigen comprises an amino acid sequence set forth in SEQ ID NO: 8. In some embodiments, the antigen is encoded by SEQ ID NO: 7.

Further provided are vaccines comprising a peptide, wherein the peptide comprises an amino acid sequence having at least about 90% identity over an entire length of the amino acid sequence set forth in SEQ ID NO: 8

Further provided are methods of treating a subject with a MUC16-expressing cancerous cell comprising administering a therapeutically effective amount of a vaccine described herein. In some embodiments, the administration includes an electroporation step. In other embodiments, the administration occurs at one or more sites on the subject.

Methods of vaccinating a subject against a MUC16-expressing cancerous cell are also provided. In some embodiments, the administration includes an electroporation step. In other embodiments, the administration occurs at one or more sites on the subject.

Also provided herein are nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90% of an entire length of SEQ ID NO: 2; (c) a nucleic acid sequence that encodes a protein that is at least 95% identical to SEQ ID NO: 2; and (d) a nucleic acid sequence that encodes a fragment comprising at least 90% of an entire length of a protein that is at least 95% identical to SEQ ID NO: 2 for use as a medicament.

Also provided herein are nucleic acid molecules comprising one or more nucleic acid sequences selected from the group consisting of: (a) a nucleic acid sequence that encodes SEQ ID NO: 4; (b) a nucleic acid sequence that encodes a fragment comprising at least 90% of an entire length of SEQ ID NO: 4; (c) a nucleic acid sequence that encodes a protein that is at least 95% identical to SEQ ID NO: 4; and (d) a nucleic acid sequence that encodes a fragment comprising at least 90% of an entire length of a protein that is at least 95% identical to SEQ ID NO: 4 for use as a medicament.

Also provided herein are nucleic acid molecules comprising one or more nucleic acid sequences selected from the group consisting of: (a) a nucleic acid sequence that encodes SEQ ID NO: 6; (b) a nucleic acid sequence that encodes a fragment comprising at least 90% of an entire length of SEQ ID NO: 6; (c) a nucleic acid sequence that encodes a protein that is at least 95% identical to SEQ ID NO: 6; and (d) a nucleic acid sequence that encodes a fragment comprising at least 90% of an entire length of a protein that is at least 95% identical to SEQ ID NO: 6 for use as a medicament.

Also provided herein are nucleic acid molecules comprising one or more nucleic acid sequences selected from the group consisting of: (a) a nucleic acid sequence that encodes SEQ ID NO: 8; (b) a nucleic acid sequence that encodes a fragment comprising at least 90% of an entire length of SEQ ID NO: 8; (c) a nucleic acid sequence that encodes a protein that is at least 95% identical to SEQ ID NO: 8; and (d) a nucleic acid sequence that encodes a fragment comprising at least 90% of an entire length of a protein that is at least 95% identical to SEQ ID NO: 8 for use as a medicament.

In some embodiments, the nucleic acid molecules described herein are for use as a medicament in the treatment of cancer. In some embodiments, the nucleic acid molecules described herein are for use in the preparation of a medicament. In some embodiments, the nucleic acid molecules described herein are for use in the preparation of a medicament for the treatment of cancer.

Also provided herein are nucleic acid molecules comprising one or more nucleic acid sequences selected from the group consisting of: (a) SEQ ID NO: 1; (b) a fragment comprising at least 90% of an entire length of SEQ ID NO: 1; (c) a fragment that is at least 95% identical to SEQ ID NO: 1; and (d) a fragment comprising at least 90% of an entire length of a nucleic acid sequence that is at least 95% identical to SEQ ID NO: 1 for use as a medicament.

Also provided herein are nucleic acid molecules comprising one or more nucleic acid sequences selected from the group consisting of: (a) SEQ ID NO: 3; (b) a fragment comprising at least 90% of an entire length of SEQ ID NO: 3; (c) a fragment that is at least 95% identical to SEQ ID NO: 3; and (d) a fragment comprising at least 90% of an entire length of a nucleic acid sequence that is at least 95% identical to SEQ ID NO: 3 for use as a medicament.

Also provided herein are nucleic acid molecules comprising one or more nucleic acid sequences selected from the group consisting of: (a) SEQ ID NO: 5; (b) a fragment comprising at least 90% of an entire length of SEQ ID NO: 5; (c) a fragment that is at least 95% identical to SEQ ID NO: 5; and (d) a fragment comprising at least 90% of an entire length of a nucleic acid sequence that is at least 95% identical to SEQ ID NO: 5 for use as a medicament.

Also provided herein are nucleic acid molecules comprising one or more nucleic acid sequences selected from the group consisting of: (a) SEQ ID NO: 7; (b) a fragment comprising at least 90% of an entire length of SEQ ID NO: 7; (c) a fragment that is at least 95% identical to SEQ ID NO: 7; and (d) a fragment comprising at least 90% of an entire length of a nucleic acid sequence that is at least 95% identical to SEQ ID NO: 7 for use as a medicament.

In some embodiments, the nucleic acid molecules described herein are for use as a medicament in the treatment of cancer. In some embodiments, the nucleic acid molecules described herein are for use in the preparation of a medicament. In some embodiments, the nucleic acid molecules described herein are for use in the preparation of a medicament for the treatment of cancer.

BRIEF DESCRIPTION OF THE DRAWINGS

FIG. 1 illustrates native human MUC16 structure. Regions targeted for MUC16 vaccine constructs are indicated.

FIG. 3 illustrates individual native MUC16 repeat sequences from which each MUC16 repeat micro-consensus (RMC) was derived and their percent sequence identity with one another (GenBank: AAL65133.2).

FIG. 5 illustrates an alignment of the modified consensus MUC16 ectodomain and transmembrane domain (SEQ ID NO: 11) and human native MUC16 ectodomain and transmembrane domain (SEQ ID NO: 12). Consensus changes are shaded in gray.

FIG. 6A shows how a preliminary synthetic MUC16 immunogen was generated by incorporating the central tandem repeat and carboxy-terminal domain design strategies. However, when the RMC4-R61 junction (the last 11 amino acids of RMC4 and first 11 amino acids of native R61), was aligned to all native MUC16 repeat junctions (the last 11 amino acids and beginning 11 amino acids of neighboring native repeats), the highest sequence identity was only 76.2%, suggesting that unwanted epitopes could possibly be introduced at this junction. FIG. 6B shows one strategy for avoiding the RMC4-R61 junction was to add a native R59 in between RMC4 and R61.

FIG. 7 is a schematic representation of the four synthetic consensus MUC16 immunogens encoded by plasmids pGX1435, pGX1436, pGX1437, pGX1438, and pGX1439.

FIGS. 8A-8C depict a size assessment and comparative modeling of human native and synthetic consensus MUC16 IRC central tandem repeat domain. FIG. 8A is a schematic diagram of native MUC16 (based on GenBank AAL65133.2) and synthetic consensus MUC16 IRC. FIG. 8B shows comparative modeling to illustrate the size differences between the native MUC16 (left) and synthetic consensus MUC16 IRC design (right). FIG. 8C is a comparative model of synthetic consensus MUC16 IRC repeat region shown in cpk format. Repeat microconsensus sequences RMC1 through RMC4 are indicated in light gray, the designed furin cleavage site and the native repeat sequences R61 through R63 are dark gray.

FIG. 11 is a diagrammatic representation of plasmid pGX1435 and synthetic consensus MUC16 IRC+R59.

FIG. 13 is a diagrammatic representation of plasmid pGX1437 and synthetic consensus MUC16 NRC.

FIG. 14 is a diagrammatic representation of plasmid pGX1438 and synthetic consensus MUC16 RMC and synthetic consensus MUC16 NRC.

FIG. 15 is a diagrammatic representation of plasmid pGX1439 and synthetic consensus MUC16 IRC.

FIGS. 22A-22C illustrate the cytolytic potential of synthetic consensus MUC16-specific CD4+ T cells and cytokine profile induced by pGX1435 (FIG. 22A), pGX1438 (FIG. 22B), and pGX1439 (FIG. 22C).

FIGS. 25A-25B illustrate cellular immune responses induced by pGX1436 in the CD4+ T cell compartment (FIG. 25A) and the cytolytic immune responses and profile of specific CD4+ T cell responses for partial length construct pGX1436 (FIG. 25B).

FIGS. 29A-29B illustrate a comparison of cellular immune responses induced by pGX1436 (FIG. 29A) and pGX1437 (FIG. 29B) against full length constructs in the CD4+ and CD8+ T cell compartments and cytokine profile of specific CD4+ and CD8+ T cell responses.

DETAILED DESCRIPTION

Figure 2:
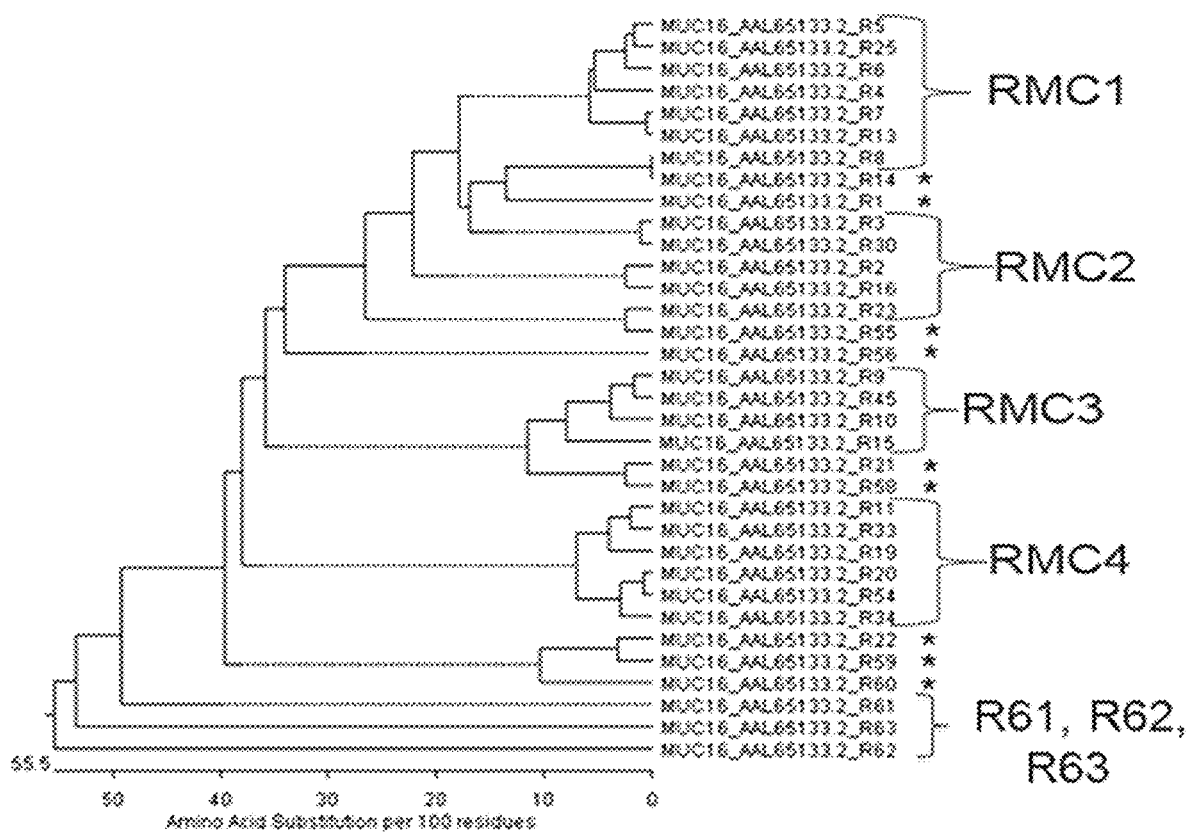
FIG. 2 depicts a phylogenetic analysis of human native MUC16 central tandem repeats.

The present invention relates to vaccines comprising a MUC16 antigen. MUC16 is expressed in many tumors. Accordingly, the vaccines provide treatment for a cancer or tumor expressing MUC16. The vaccine of the invention can provide any combination of particular cancer antigens for the particular prevention or treatment of the cancer of a subject that is in need of treatment.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The aforementioned approaches can be combined so that the final recombinant cancer antigen has a percent similarity to native cancer antigen amino acid sequence as discussed, above.

The mucin-16 ("MUC16") antigen can be a consensus MUC16 antigen derived, in part, from the sequences of MUC16 from different species or from different isoforms within a species, and thus, the consensus MUC16 antigen is non-native.

The MUC16 antigen may also comprise a selection of repeat micro-consensus (RMC) or native repeat (R) sequences derived from native RMC or R sequences. In some embodiments, nucleic acid constructs are provided in which two or more RMC and/or R sequences are linked to each other by proteolytic cleavage sites. A furin proteolytic cleavage site is an example of a proteolytic cleavage site which may link RMC and/or R domains in a fusion protein expressed by a construct.

Further modifications to the MUC16 antigen may include mutations of asparagine residues in the ectodomain and transmembrane domains and the addition of upstream Kozak and/or IgE leader sequences to the N-terminus of the MUC16 antigen.

The recombinant MUC16 can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-$\gamma$) and/or tumor necrosis factor alpha (TNF-$\alpha$). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-$\beta$, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B- cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the MUC16 antigens and/or the nucleic acid molecules encoding the antigens as described herein.

"Antibody" as used herein means an antibody of classes IgG, IgM, IgA, IgD, or IgE, or fragments, or derivatives thereof, including Fab, F(ab')2, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof which exhibits sufficient binding specificity to a desired epitope or a sequence derived therefrom.

"MUC16 antigen" refers to proteins comprising the amino acid sequence selected from the group consisting of: amino acids 19-1490 of SEQ ID NO: 2; amino acids 19-642 of SEQ ID NO: 4; amino acids 19-710 of SEQ ID NO: 6; amino acids 19-642 and 650-1341 of SEQ ID NO: 8; SEQ ID NO: 2; SEQ ID NO: 4; SEQ ID NO: 6; SEQ ID NO: 8; fragments thereof of lengths set forth herein, variants, i.e. proteins with sequences having identity to SEQ ID NO: 2, SEQ ID NO: 4, SEQ ID NO: 6 or SEQ ID NO: 8 as set forth herein, fragments of variants having lengths set forth herein of SEQ ID NO: 2, SEQ ID NO: 4, SEQ ID NO: 6 or SEQ ID NO: 8; fragments thereof of lengths set forth herein, variants, i.e. proteins with sequences having identity to SEQ ID NO: 2, SEQ ID NO: 4, SEQ ID NO: 6 or SEQ ID NO: 8 as set forth herein, fragments of variants having lengths set forth herein, and combinations thereof. Antigens may optionally include signal peptides such as those from other proteins.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be nucleic acid molecule fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of an entire length of one or more of the nucleic acid sequences described herein, excluding any heterologous signal peptide added. In some embodiments, fragments can comprise at least 90%, at least 91%, at least 92%, at least 93%, at least 94%, at least 95%, at least 96%, at least 97%, at least 98%, or at least 99% of an entire length of one or more of the nucleic acid sequences set forth below, excluding any heterologous signal peptide added.

In some embodiments, the fragments may be at least 10%, at least 20%, at least 30%, at least 40%, at least 50%, at least 60%, at least 70%, at least 80%, at least 90%, or at least 95% identical to one or more of nucleic acid sequences described herein, excluding any heterologous signal peptide. In some embodiments, the fragments may be at least 95%, at least 96%, at least 97%, at least 98%, or at least 99% identical to one or more of the nucleic acid sequences set forth below, excluding any heterologous signal peptide added.

In further embodiments, the fragments may additionally optionally comprise sequence encoding a heterologous signal peptide which is not included when calculating percent identity. Fragments may also comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 1700 nucleotides or more, 1750 nucleotides or more, 1800 nucleotides or more, 1850 nucleotides or more, 1900 nucleotides or more, 1950 nucleotides or more, 2000 nucleotides or more, 2050 nucleotides or more, 2100 nucleotides or more, 2150 nucleotides or more, 2200 nucleotides or more, 2250 nucleotides or more, 2300 nucleotides or more, 2350 nucleotides or more, 2400 nucleotides or more, 2450 nucleotides or more, 2500 nucleotides or more, 2550 nucleotides or more, 2600 nucleotides or more, 2650 nucleotides or more, 2700 nucleotides or more, 2750 nucleotides or more, 2800 nucleotides or more, 2850 nucleotides or more, 2900 nucleotides or more, 2950 nucleotides or more, 3000 nucleotides or more, 3050 nucleotides or more, 3100 nucleotides or more, 3150 nucleotides or more, 3200 nucleotides or more, 3250 nucleotides or more, 3300 nucleotides or more, 3350 nucleotides or more, 3400 nucleotides or more, 3450 nucleotides or more, 3500 nucleotides or more, 3550 nucleotides or more, 3600 nucleotides or more, 3650 nucleotides or more, 3700 nucleotides or more, 3750 nucleotides or more, 3800 nucleotides or more, 3850 nucleotides or more, 3900 nucleotides or more, 3950 nucleotides or more, 4000 nucleotides or more, 4050 nucleotides or more, 4100 nucleotides or more, 4150 nucleotides or more, 4200 nucleotides or more, 4250 nucleotides or more, 4300 nucleotides or more, 4350 nucleotides or more, 4400 nucleotides or more, 4450 nucleotides or more, 4500 of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acid sequences described herein. Fragments of consensus proteins can comprise at least 10%, at least 20%, at least 30%, at least 40%, at least 50%, at least 60%, at least 70%, at least 80%, at least 90% or at least 95% of an entire length of a consensus protein, excluding any heterologous signal peptide added. In some embodiments, the fragment may comprise at least 90%, at least 91%, at least 92%, at least 93%, at least 94%, at least 95%, at least 96%, at least 97%, at least 98%, or at least 99% of the length of one or more of the amino sequences set forth below, excluding any heterologous signal peptide added.

In some embodiments, the fragments may be at least 10%, at least 20%, at least 30%, at least 40%, at least 50%, at least 60%, at least 70%, at least 80%, at least 90%, or at least 95% identical to one or more of amino acid sequences described herein, excluding any heterologous signal peptide. In some embodiments, the fragments may be at least 95%, at least 96%, at least 97%, at least 98%, or at least 99% identical to one or more of the amino acid sequences set forth below, excluding any heterologous signal peptide added In further embodiments, the fragments may additionally optionally comprise sequence encoding a heterologous signal peptide which is not included when calculating percent identity. Fragments may further comprise a signal peptide such as an immunoglobulin signal peptide, for example an IgE or IgG signal peptide.

In some embodiments, fragments of consensus proteins can comprise at 550 amino acids or more, 600 amino acids or more, 650 amino acids or more, 700 amino acids or more, 750 amino acids or more, 800 amino acids or more, 850 amino acids or more, 900 amino acids or more, 950 amino acids or more, 1000 amino acids or more, 1050 amino acids or more, 1100 amino acids or more, 1150 amino acids or more, 1200 amino acids or more, 1250 amino acids or more, 1300 amino acids or more, 1350 of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contains the necessary regulatory elements operably linked to a coding sequence that encodes a protein such that, when present in a cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule which is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, CMV IE promoter and human cytomegalovirus immediate-early promoter (hCMV). In certain embodiments, the promoter is a hCMV promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5× SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, a non-human primate such as a chimpanzee, a dog, a cat, a horse, a cow, a mouse, or a rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccine

Provided herein are vaccines comprising a MUC16 antigen or a nucleic acid molecule encoding a MUC16 antigen as described herein. In some embodiments, the vaccines comprise one or more nucleic acid molecules that encode a MUC16 antigen as described herein. In some embodiments, the vaccines comprise one or more nucleic acid molecules that comprise a nucleic acid sequence that encodes amino acids 19-1490 of SEQ ID NO: 2; a nucleic acid sequence that encodes a fragment comprising at least 90% of an entire length of a protein comprising amino acids 19-1490 of SEQ ID NO: 2; a nucleic acid sequence that encodes a protein that is at least 95% identical to amino acids 19-1490 of SEQ ID NO: 2; and/or a nucleic acid sequence that encodes a fragment comprising at least 90% of an entire length of a protein that is at least 95% identical to amino acids 19-1490 of SEQ ID NO: 2. In some embodiments, the vaccines comprise one or more nucleic acid molecules that comprise a nucleic acid sequence that encodes amino acids 19-642 of SEQ ID NO: 4; a nucleic acid sequence that encodes a fragment comprising at least 90% of an entire length of a protein comprising amino acids 19-642 of SEQ ID NO: 4; a nucleic acid sequence that encodes a protein that is at least 95% identical to amino acids 19-642 of SEQ ID NO: 4; and/or a nucleic acid sequence that encodes a fragment comprising at least 90% of an entire length of a protein that is at least 95% identical to amino acids 19-642 of SEQ ID NO: 4. In some embodiments, the vaccines comprise one or more nucleic acid molecules that comprise a nucleic acid sequence that encodes amino acids 19-710 of SEQ ID NO: 6; a nucleic acid sequence that encodes a fragment comprising at least 90% of an entire length of a protein comprising amino acids 19-710 of SEQ ID NO: 6; a nucleic acid sequence that encodes a protein that is at least 95% identical to amino acids 19-710 of SEQ ID NO: 6; and/or a nucleic acid sequence that encodes a fragment comprising at least 90% of an entire length of a protein that is at least 95% identical to amino acids 19-710 of SEQ ID NO: 6. In some embodiments, the vaccines comprise one or more nucleic acid molecules that comprise a nucleic acid sequence that encodes amino acids 19-642 and 650-1341 of SEQ ID NO: 8; a nucleic acid sequence that encodes a fragment comprising at least 90% of an entire length of a protein comprising amino acids 19-642 and 650-1341 of SEQ ID NO: 8; a nucleic acid sequence that encodes a protein that is at least 95% identical to amino acids 19-642 and 650-1341 of SEQ ID NO: 8; and/or a nucleic acid sequence that encodes a fragment comprising at least 90% of an entire length of a protein that is at least 95% identical to amino acids 19-642 and 650-1341 of SEQ ID NO: 8. In some embodiments, the vaccines comprise one or more nucleic acid molecules that comprise a nucleic acid sequence that encodes amino acids 19-1341 of SEQ ID NO: 8; a nucleic acid sequence that encodes a fragment comprising at least 90% of an entire length of a protein comprising amino acids 19-1341 of SEQ ID NO: 8; a nucleic acid sequence that encodes a protein that is at least 95% identical to amino acids 19-1341 of SEQ ID NO: 8; and/or a nucleic acid sequence that encodes a fragment comprising at least 90% of an entire length of a protein that is at least 95% identical to amino acids 19-1341 of SEQ ID NO: 8.

In some embodiments, the vaccines comprise one or more nucleic acid molecules that comprise nucleotides 55-4470 of SEQ ID NO: 1; a fragment comprising at least 90% an entire length of a nucleic acid molecule comprising nucleotides 55-4470 of SEQ ID NO: 1; a fragment that is at least 95% identical to nucleotides 55-4470 of SEQ ID NO: 1; and/or a fragment comprising at least 90% of an entire length of a nucleic acid sequence that is at least 95% identical to nucleotides 55-4470 of SEQ ID NO: 1. In some embodiments, the vaccines comprise one or more nucleic acid molecules that comprise nucleotides 55-1926 of SEQ ID NO: 3; a fragment comprising at least 90% an entire length of a nucleic acid molecule comprising nucleotides 55-1926 of SEQ ID NO: 3; a fragment that is at least 95% identical to nucleotides 55-1926 of SEQ ID NO: 3; and/or a fragment comprising at least 90% of an entire length of a nucleic acid sequence that is at least 95% identical to nucleotides 55-1926 of SEQ ID NO: 3. In some embodiments, the vaccines comprise one or more nucleic acid molecules that comprise nucleotides 55-2130 of SEQ ID NO: 5; a fragment comprising at least 90% an entire length of a nucleic acid molecule comprising nucleotides 55-2130 of SEQ ID NO: 5; a fragment that is at least 95% identical to nucleotides 55-2130 of SEQ ID NO: 5; and/or a fragment comprising at least 90% of an entire length of a nucleic acid sequence that is at least 95% identical to nucleotides 55-2130 of SEQ ID NO: 5. In some embodiments, the vaccines comprise one or more nucleic acid molecules that comprise nucleotides 55-1926 and 1948-4023 SEQ ID NO: 7; a fragment comprising at least 90% an entire length of a nucleic acid molecule comprising nucleotides 55-1926 and 1948-4023 of SEQ ID NO: 7; a fragment that is at least 95% identical to nucleotides 55-1926 and 1948-4023 of SEQ ID NO: 7; and/or a fragment comprising at least 90% of an entire length of a nucleic acid sequence that is at least 95% identical to nucleotides 55-1926 and 1948-4023 of SEQ ID NO: 7. In some embodiments, the vaccines comprise one or more nucleic acid molecules that comprise nucleotides 55-4023 SEQ ID NO: 7; a fragment comprising at least 90% of an entire length of a nucleic acid molecule comprising nucleotides 55-4023 of SEQ ID NO: 7; a fragment that is at least 95% identical to nucleotides 55-4023 of SEQ ID NO: 7; and/or a fragment comprising at least 90% of an entire length of a nucleic acid sequence that is at least 95% identical to nucleotides 55-4023 of SEQ ID NO: 7.

In some embodiments, the vaccines comprise one or more nucleic acid molecules that comprise a nucleic acid sequence that encodes SEQ ID NO: 2; a nucleic acid sequence that encodes a fragment comprising at least 90% of the length of SEQ ID NO. 2; a nucleic acid sequence that encodes a protein that is at least 95% identical to SEQ ID NO: 2; and/or a nucleic acid sequence that encodes a fragment comprising at least 90% of an entire length of a protein that is at least 95% identical to SEQ ID NO: 2. In some embodiments, the vaccines comprise one or more nucleic acid molecules that comprise a nucleic acid sequence that encodes SEQ ID NO: 4; a nucleic acid sequence that encodes a fragment comprising at least 90% of the length of SEQ ID NO. 4; a nucleic acid sequence that encodes a protein that is at least 95% identical to SEQ ID NO: 4; and/or a nucleic acid sequence that encodes a fragment comprising at least 90% of an entire length of a protein that is at least 95% identical to SEQ ID NO: 4. In some embodiments, the vaccines comprise one or more nucleic acid molecules that comprise a nucleic acid sequence that encodes SEQ ID NO: 6; a nucleic acid sequence that encodes a fragment comprising at least 90% of the length of SEQ ID NO. 6; a nucleic acid sequence that encodes a protein that is at least 95% identical to SEQ ID NO: 6; and/or a nucleic acid sequence that encodes a fragment comprising at least 90% of an entire length of a protein that is at least 95% identical to SEQ ID NO: 6. In some embodiments, the vaccines comprise one or more nucleic acid molecules that comprise a nucleic acid sequence that encodes SEQ ID NO: 8; a nucleic acid sequence that encodes a fragment comprising at least 90% of the length of SEQ ID NO. 8; a nucleic acid sequence that encodes a protein that is at least 95% identical to SEQ ID NO: 8; and/or a nucleic acid sequence that encodes a fragment comprising at least 90% of an entire length of a protein that is at least 95% identical to SEQ ID NO: 8.

In some embodiments, the vaccines comprise one or more nucleic acid molecules that comprise SEQ ID NO: 1; a fragment comprising at least 90% of the entire length of SEQ ID NO: 1; a fragment that is at least 95% identical to SEQ ID NO: 1; and/or a fragment comprising at least 90% of the entire length of a nucleic acid sequence that is at least 95% identical to SEQ ID NO: 1. In some embodiments, the vaccines comprise one or more nucleic acid molecules that comprise SEQ ID NO: 3; a fragment comprising at least 90% of the entire length of SEQ ID NO: 3; a fragment that is at least 95% identical to SEQ ID NO: 3; and/or a fragment comprising at least 90% of the entire length of a nucleic acid sequence that is at least 95% identical to SEQ ID NO: 3. In some embodiments, the vaccines comprise one or more nucleic acid molecules that comprise SEQ ID NO: 5; a fragment comprising at least 90% of the entire length of SEQ ID NO: 5; a fragment that is at least 95% identical to SEQ ID NO: 5; and/or a fragment comprising at least 90% of the entire length of a nucleic acid sequence that is at least 95% identical to SEQ ID NO: 5. In some embodiments, the vaccines comprise one or more nucleic acid molecules that comprise SEQ ID NO: 7; a fragment comprising at least 90% of the entire length of SEQ ID NO: 7; a fragment that is at least 95% identical to SEQ ID NO: 7; and/or a fragment comprising at least 90% of the entire length of a nucleic acid sequence that is at least 95% identical to SEQ ID NO: 7.

In some embodiments, the vaccines comprise a MUC16 antigen, wherein the antigen comprises amino acids 19-1490 of SEQ ID NO: 2; a fragment comprising at least 90% of an entire length of a protein comprising amino acids 19-1490 of SEQ ID NO: 2 a protein that is at least 95% identical to amino acids 19-1490 of SEQ ID NO: 2; and/or a fragment comprising at least 90% of an entire length of a protein that is at least 95% identical to amino acids 19-1490 of SEQ ID NO: 2.

In some embodiments, the vaccine comprises a MUC16 antigen, wherein the antigen comprises SEQ ID NO: 2; a fragment comprising at least 90% of the length of SEQ ID NO. 2; an amino acid sequence that is at least 95% identical to SEQ ID NO: 2; and/or a fragment comprising at least 90% of an entire length of a protein that is at least 95% identical to SEQ ID NO: 2.

In some embodiments, the vaccines comprise a MUC16 antigen, wherein the antigen comprises amino acids 19-642 of SEQ ID NO: 4; a fragment comprising at least 90% of an entire length of a protein comprising amino acids 19-642 of SEQ ID NO: 4; a protein that is at least 95% identical to amino acids 19-642 of SEQ ID NO: 4; and/or a fragment comprising at least 90% of an entire length of a protein that is at least 95% identical to amino acids 19-642 of SEQ ID NO: 4.

In some embodiments, the vaccine comprises a MUC16 antigen, wherein the antigen comprises SEQ ID NO: 4; a fragment comprising at least 90% of the length of SEQ ID NO. 4; an amino acid sequence that is at least 95% identical to SEQ ID NO: 4; and/or a fragment comprising at least 90% of an entire length of a protein that is at least 95% identical to SEQ ID NO: 4.

In some embodiments, the vaccines comprise a MUC16 antigen, wherein the antigen comprises amino acids 19-710 of SEQ ID NO: 6; a fragment comprising at least 90% of an entire length of a protein comprising amino acids 19-710 of SEQ ID NO: 6; a protein that is at least 95% identical to amino acids 19-710 of SEQ ID NO: 6; and/a fragment comprising at least 90% of an entire length of a protein that is at least 95% identical to amino acids 19-710 of SEQ ID NO: 6.

In some embodiments, the vaccine comprises a MUC16 antigen, wherein the antigen comprises SEQ ID NO: 6; a fragment comprising at least 90% of the length of SEQ ID NO. 6; an amino acid sequence that is at least 95% identical to SEQ ID NO: 6; and/or a fragment comprising at least 90% of an entire length of a protein that is at least 95% identical to SEQ ID NO: 6.

In some embodiments, the vaccine comprises a MUC16 antigen, wherein the antigen comprises amino acids 19-642 and 650-1341 of SEQ ID NO: 8; a fragment comprising at least 90% of an entire length of a protein comprising amino acids 19-642 and 650-1341 of SEQ ID NO: 8; an amino acid sequence that is at least 95% identical to amino acids 19-642 and 650-1341 of SEQ ID NO: 8; and/or a fragment comprising at least 90% of an entire length of an amino acid sequence that is at least 95% identical to amino acids 19-642 and 650-1341 of SEQ ID NO: 8.

In some embodiments, the vaccine comprises a MUC16 antigen, wherein the antigen comprises amino acids 19-1341 of SEQ ID NO: 8; a fragment comprising at least 90% of an entire length of a protein comprising amino acids 19-1341 of SEQ ID NO: 8; an amino acid sequence that is at least 95% identical to amino acids 19-1341 of SEQ ID NO: 8; and/or a fragment comprising at least 90% of an entire length of an amino acid sequence that is at least 95% identical to amino acids 19-1341 of SEQ ID NO: 8.

In some embodiments, the vaccine comprises a MUC16 antigen, wherein the antigen comprises SEQ ID NO: 8; a fragment comprising at least 90% of the length of SEQ ID NO. 8; an amino acid sequence that is at least 95% identical to SEQ ID NO: 8; and/or a fragment comprising at least 90% of an entire length of a protein that is at least 95% identical to SEQ ID NO: 8.

The vaccines can be capable of generating in a subject an immune response against the antigen. The immune response can be a therapeutic or prophylactic immune response. The vaccines can be used to protect against cancer, for example, a cancer or tumor expressing MUC16. The vaccines can be used to prevent and/or treat a tumor expressing MUC16 in a subject in need thereof. The vaccines can induce cellular and/or antibody responses against MUC16 and against tumors expressing MUC16. In one embodiment, the vaccines can be used to protect against, to prevent and/or treat, or to induce a cellular and/or antibody response against ovarian cancer cells expressing MUC16, specifically epithelial ovarian cancer cells expressing MUC16, more specifically serous ovarian cancer cells expressing MUC16.

The development of a cancer vaccine as described herein comprises identifying a cancer antigen, e.g., MUC16, that is not recognized by the immune system and is an aberrantly expressed self-antigen. The cancer antigen identified is changed from a self-antigen to a foreign antigen in order to be recognized by the immune system. The redesign of the nucleic acid and amino acid sequences of the recombinant cancer antigen from a self to a foreign antigen breaks tolerance of the antigen by the immune system. In order to break tolerance, several redesign measures can be applied to the cancer antigen as described below.

The recombinant cancer antigen of the vaccine is not recognized as self, thereby breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that downregulate MHC presentation, factors that upregulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. In some embodiments, the nucleic acid molecule may comprise an expression vector. The DNA vaccine can further comprise elements or reagents that inhibit it from integrating into the chromosome.

The vaccine can include an RNA encoding the cancer antigen. The RNA vaccine can be introduced into the cell.

The vaccine can be an attenuated live vaccine, a vaccine using recombinant vectors to deliver antigen, subunit vaccines, and glycoprotein vaccines, for example, but not limited to, the vaccines described in U.S. Pat. Nos. 4,510, 245; 4,797,368; 4,722,848; 4,790,987; 4,920,209; 5,017, 487; 5,077,044; 5,110,587; 5,112,749; 5,174,993; 5,223, 424; 5,225,336; 5,240,703; 5,242,829; 5,294,441; 5,294, 548; 5,310,668; 5,387,744; 5,389,368; 5,424,065; 5,451, 499; 5,453,364; 5,462,734; 5,470,734; 5,474,935; 5,482, 713; 5,591,439; 5,643,579; 5,650,309; 5,698,202; 5,955, 088; 6,034,298; 6,042,836; 6,156,319 and 6,589,529, which are each incorporated herein by reference.

In some embodiments, the nucleic acid vaccine may further comprise a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, and/or RANTES may be included on one or more nucleic acid molecules that comprise coding sequence for one or more antigens. Coding sequence for IL-12, IL-15, IL-28, IL-31, IL-33, and/or RANTES may be encoded by the nucleic acid vaccine, such as on the same plasmid, or they may be included on separate nucleic acid molecules such as a separate plasmid.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed below.

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as MEW class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Antigen

As described above, the vaccine can comprise an antigen or a nucleic acid molecule encoding an antigen. The antigen can be MUC16, a fragment thereof, a variant thereof, or a combination thereof. MUC16 is a member of the mucin family of high molecular weight glycoproteins. Mucins are expressed by specialized epithelial cells surrounding the luminal surface of various organs of the respiratory, gastrointestinal and reproductive tracts. Mucins have direct and indirect roles in the maintenance of epithelial integrity and the lubrication and protection of epithelial surfaces.

MUC16 has been associated with tumor or cancer formation. The tandem repeat domain of MUC16 contains a repeating peptide epitope, CA125, which has become the gold-standard biomarker for multiple clinical scenarios that occur throughout diagnosis and treatment of ovarian cancer, including: 1) screening for early detection, 2) distinguishing between benign and malignant disease in pre- and post-menopausal women presenting with pelvic masses, and 3) monitoring response to therapy. Additionally, functional studies have shown that MUC16 contributes to the transformation and metastasis of ovarian tumors.

Accordingly, the vaccine can be used for treating subjects suffering from MUC16-expressing cancer or tumors. In some embodiments, the cancer is ovarian cancer. The MUC16 antigen can differ from the native, "normal" MUC16, and thus provide therapy or prophylaxis against a MUC16 antigen-expressing tumor. Accordingly, MUC16 antigen sequences that differ from the native MUC16 sequence, and nucleic acid molecules encoding such MUC16 antigen sequences (i.e., recombined or mutated MUC16 genes or sequences), are provided herein.

Nucleic acid molecules comprising the above-described heterologous sequences are provided. Nucleic acid molecules consisting of the above-described heterologous sequences are provided. In some embodiments, nucleic acid molecules comprising one or more nucleic acid sequences selected from the group consisting of: (a) nucleotides 55-4470 of SEQ ID NO: 1; (b) a fragment comprising at least 90%, 91%, 92%, 93%, 94%, 95%, 96%, 97%, 98% or 99% an entire length of a nucleic acid molecule comprising nucleotides 55-4470 of SEQ ID NO: 1; (c) a fragment that is at least 95%, 96%, 97%, 98% or 99% identical to nucleotides 55-4470 of SEQ ID NO: 1; and (d) a fragment comprising at least 90%, 91%, 92%, 93%, 94%, 95%, 96%, 97%, 98% or 99% of an entire length of a nucleic acid sequence that is at least 95%, 96%, 97%, 98% or 99% identical to nucleotides 55-4470 of SEQ ID NO: 1. In some embodiments, nucleic acid molecules comprising one or more nucleic acid sequences selected from the group consisting of: (a) SEQ ID NO: 1; (b) a fragment comprising at least 90%, 91%, 92%, 93%, 94%, 95%, 96%, 97%, 98% or 99% of an entire length of SEQ ID NO: 1; (c) a fragment that is at least 95%, 96%, 97%, 98% or 99% identical to SEQ ID NO: 1; and (d) a fragment comprising at least 90% of an entire length of a nucleic acid sequence that is at least 95%, 96%, 97%, 98% or 99% identical to SEQ ID NO: 1. In some embodiments, the nucleic acid molecule comprises the nucleic acid sequence set forth in SEQ ID NO: 1.

In some embodiments, nucleic acid molecules comprising one or more nucleic acid sequences selected from the group consisting of: (a) nucleotides 55-1926 of SEQ ID NO: 3; (b) a fragment comprising at least 90%, 91%, 92%, 93%, 94%, 95%, 96%, 97%, 98% or 99% an entire length of a nucleic acid molecule comprising nucleotides 55-1926 of SEQ ID NO: 3; (c) a fragment that is at least 95%, 96%, 97%, 98% or 99% identical to nucleotides 55-1926 of SEQ ID NO: 3; and (d) a fragment comprising at least 90%, 91%, 92%, 93%, 94%, 95%, 96%, 97%, 98% or 99% of an entire length of a nucleic acid sequence that is at least 95%, 96%, 97%, 98% or 99% identical to nucleotides 55-1926 of SEQ ID NO: 3. In some embodiments, nucleic acid molecules comprising one or more nucleic acid sequences selected from the group consisting of: (a) SEQ ID NO: 3; (b) a fragment comprising at least 90%, 91%, 92%, 93%, 94%, 95%, 96%, 97%, 98% or 99% of an entire length of SEQ ID NO: 3; (c) a fragment that is at least 95%, 96%, 97%, 98% or 99% identical to SEQ ID NO: 3; and (d) a fragment comprising at least 90% of an entire length of a nucleic acid sequence that is at least 95%, 96%, 97%, 98% or 99% identical to SEQ ID NO: 3. In some embodiments, the nucleic acid molecule comprises the nucleic acid sequence set forth in SEQ ID NO: 3.

In some embodiments, nucleic acid molecules comprising one or more nucleic acid sequences selected from the group consisting of: (a) nucleotides 55-2130 of SEQ ID NO: 5; (b) a fragment comprising at least 90%, 91%, 92%, 93%, 94%, 95%, 96%, 97%, 98% or 99% an entire length of a nucleic acid molecule comprising nucleotides 55-2130 of SEQ ID NO: 5; (c) a fragment that is at least 95%, 96%, 97%, 98% or 99% identical to nucleotides 55-2130 of SEQ ID NO: 5; and (d) a fragment comprising at least 90%, 91%, 92%, 93%, 94%, 95%, 96%, 97%, 98% or 99% of an entire length of a nucleic acid sequence that is at least 95%, 96%, 97%, 98% or 99% identical to nucleotides 55-2130 of SEQ ID NO: 5. In some embodiments, nucleic acid molecules comprising one or more nucleic acid sequences selected from the group consisting of: (a) SEQ ID NO: 5; (b) a fragment comprising at least 90%, 91%, 92%, 93%, 94%, 95%, 96%, 97%, 98% or 99% of an entire length of SEQ ID NO: 5; (c) a fragment that is at least 95%, 96%, 97%, 98% or 99% identical to SEQ ID NO: 5; and (d) a fragment comprising at least 90% of an entire length of a nucleic acid sequence that is at least 95%, 96%, 97%, 98% or 99% identical to SEQ ID NO: 5. In some embodiments, the nucleic acid molecule comprises the nucleic acid sequence set forth in SEQ ID NO: 5.

In some embodiments, nucleic acid molecules comprising one or more nucleic acid sequences selected from the group consisting of: (a) nucleotides 55-1926 and 1948-4023 SEQ ID NO: 7; (b) a fragment comprising at least 90%, 91%, 92%, 93%, 94%, 95%, 96%, 97%, 98% or 99% an entire length of a nucleic acid molecule comprising nucleotides 55-1926 and 1948-4023 of SEQ ID NO: 7; (c) a fragment that is at least 95%, 96%, 97%, 98% or 99% identical to nucleotides 55-1926 and 1948-4023 of SEQ ID NO: 7; and (d) a fragment comprising at least 90%, 91%, 92%, 93%, 94%, 95%, 96%, 97%, 98% or 99% of an entire length of a nucleic acid sequence that is at least 95%, 96%, 97%, 98% or 99% identical to nucleotides 55-1926 and 1948-4023 of SEQ ID NO: 7. In some embodiments, nucleic acid molecules comprising one or more nucleic acid sequences selected from the group consisting of: (a) nucleotides 55-4023 SEQ ID NO: 7; (b) a fragment comprising at least 90%, 91%, 92%, 93%, 94%, 95%, 96%, 97%, 98% or 99 an entire length of a nucleic acid molecule comprising nucleotides 55-4023 of SEQ ID NO: 7; (c) a fragment that is at least 95%, 96%, 97%, 98% or 99% identical to nucleotides 55-4023 of SEQ ID NO: 7; and (d) a fragment comprising at least 90%, 91%, 92%, 93%, 94%, 95%, 96%, 97%, 98% or 99% of an entire length of a nucleic acid sequence that is at least 95%, 96%, 97%, 98% or 99% identical to nucleotides 55-4023 of SEQ ID NO: 7. In some embodiments, nucleic acid molecules comprising one or more nucleic acid sequences selected from the group consisting of: (a) SEQ ID NO: 7; (b) a fragment comprising at least 90%, 91%, 92%, 93%, 94%, 95%, 96%, 97%, 98% or 99% of an entire length of SEQ ID NO: 7; (c) a fragment that is at least 95%, 96%, 97%, 98% or 99% identical to SEQ ID NO: 7; and (d) a fragment comprising at least 90% of an entire length of a nucleic acid sequence that is at least 95%, 96%, 97%, 98% or 99% identical to SEQ ID NO: 7. In some embodiments, the nucleic acid molecule comprises the nucleic acid sequence set forth in SEQ ID NO: 7

Provided herein are nucleic acid sequences that encode MUC16 antigens. In some embodiments, nucleic acid molecules comprising one or more nucleic acid sequences selected from the group consisting of: (a) a nucleic acid sequence that encodes amino acids 19-1490 of SEQ ID NO: 2; (b) a nucleic acid sequence that encodes a fragment comprising at least 90%, 91%, 92%, 93%, 94%, 95%, 96%, 97%, 98% or 99% of an entire length of a protein comprising amino acids 19-1490 of SEQ ID NO: 2; (c) a nucleic acid sequence that encodes a protein that is at least 95%, 96%, 97%, 98% or 99% identical to amino acids 19-1490 of SEQ ID NO: 2; and (d) a nucleic acid sequence that encodes a fragment comprising at least 90%, 91%, 92%, 93%, 94%, 95%, 96%, 97%, 98% or 99% of an entire length of a protein that is at least 95%, 96%, 97%, 98% or 99% identical to amino 19-1490 of SEQ ID NO: 2. In some embodiments, nucleic acid molecules comprising one or more nucleic acid sequences selected from the group consisting of: (a) a nucleic acid sequence that encodes SEQ ID NO: 2; (b) a nucleic acid sequence that encodes a fragment comprising at least 90%, 91%, 92%, 93%, 94%, 95%, 96%, 97%, 98% or 99% of an entire length of SEQ ID NO: 2; (c) a nucleic acid sequence that encodes a protein that is at least 95%, 96%, 97%, 98% or 99% identical to SEQ ID NO: 2; and (d) a nucleic acid sequence that encodes a fragment comprising at least 90% of an entire length of a protein that is at least 95%, 96%, 97%, 98% or 99% identical to SEQ ID NO: 2 are provided.

In some embodiments, nucleic acid molecules comprising one or more nucleic acid sequences selected from the group consisting of: (a) a nucleic acid sequence that encodes amino acids 19-642 of SEQ ID NO: 4; (b) a nucleic acid sequence that encodes a fragment comprising at least 90%, 91%, 92%, 93%, 94%, 95%, 96%, 97%, 98% or 99% of an entire length of a protein comprising amino acids 19-642 of SEQ ID NO: 4; (c) a nucleic acid sequence that encodes a protein that is at least 95%, 96%, 97%, 98% or 99% identical to amino acids 19-642 of SEQ ID NO: 4; and (d) a nucleic acid sequence that encodes a fragment comprising at least 90%, 91%, 92%, 93%, 94%, 95%, 96%, 97%, 98% or 99% of an entire length of a protein that is at least 95%, 96%, 97%, 98% or 99% identical to amino 19-642 of SEQ ID NO: 4. In some embodiments, nucleic acid molecules comprising one or more nucleic acid sequences selected from the group consisting of: (a) a nucleic acid sequence that encodes SEQ ID NO: 4; (b) a nucleic acid sequence that encodes a fragment comprising at least 90%, 91%, 92%, 93%, 94%, 95%, 96%, 97%, 98% or 99% of an entire length of SEQ ID NO: 4; (c) a nucleic acid sequence that encodes a protein that is at least 95%, 96%, 97%, 98% or 99% identical to SEQ ID NO: 4; and (d) a nucleic acid sequence that encodes a fragment comprising at least 90% of an entire length of a protein that is at least 95%, 96%, 97%, 98% or 99% identical to SEQ ID NO: 4 are provided.

In some embodiments, nucleic acid molecules comprising one or more nucleic acid sequences selected from the group consisting of: (a) a nucleic acid sequence that encodes amino acids 19-710 of SEQ ID NO: 6; (b) a nucleic acid sequence that encodes a fragment comprising at least 90%, 91%, 92%, 93%, 94%, 95%, 96%, 97%, 98% or 99% of an entire length of a protein comprising amino acids 19-710 of SEQ ID NO: 6; (c) a nucleic acid sequence that encodes a protein that is at least 95%, 96%, 97%, 98% or 99% identical to amino acids 19-710 of SEQ ID NO: 6; and (d) a nucleic acid sequence that encodes a fragment comprising at least 90%, 91%, 92%, 93%, 94%, 95%, 96%, 97%, 98% or 99% of an entire length of a protein that is at least 95%, 96%, 97%, 98% or 99% identical to amino 19-710 of SEQ ID NO: 6. In some embodiments, nucleic acid molecules comprising one or more nucleic acid sequences selected from the group consisting of: (a) a nucleic acid sequence that encodes SEQ ID NO: 6; (b) a nucleic acid sequence that encodes a fragment comprising at least 90%, 91%, 92%, 93%, 94%, 95%, 96%, 97%, 98% or 99% of an entire length of SEQ ID NO: 6; (c) a nucleic acid sequence that encodes a protein that is at least 95%, 96%, 97%, 98% or 99% identical to SEQ ID NO: 6; and (d) a nucleic acid sequence that encodes a fragment comprising at least 90% of an entire length of a protein that is at least 95%, 96%, 97%, 98% or 99% identical to SEQ ID NO: 6 are provided.

In some embodiments, nucleic acid molecules comprising one or more nucleic acid sequences selected from the group consisting of: (a) a nucleic acid sequence that encodes amino acids 19-642 and 650-1341 of SEQ ID NO: 8; (b) a nucleic acid sequence that encodes a fragment comprising at least 90%, 91%, 92%, 93%, 94%, 95%, 96%, 97%, 98% or 99% of an entire length of a protein comprising amino acids 19-642 and 650-1341 of SEQ ID NO: 8; (c) a nucleic acid sequence that encodes a protein that is at least 95%, 96%, 97%, 98% or 99% identical to amino acids 19-642 and 650-1341 of SEQ ID NO: 8; and (d) a nucleic acid sequence that encodes a fragment comprising at least 90%, 91%, 92%, 93%, 94%, 95%, 96%, 97%, 98% or 99% of an entire length of a protein that is at least 95%, 96%, 97%, 98% or 99% identical to amino acids 19-642 and 650-1341 of SEQ ID NO: 8. In some embodiments, nucleic acid molecules comprising one or more nucleic acid sequences selected from the group consisting of: (a) a nucleic acid sequence that encodes amino acids 19-1341 of SEQ ID NO: 8; (b) a nucleic acid sequence that encodes a fragment comprising at least 90%, 91%, 92%, 93%, 94%, 95%, 96%, 97%, 98% or 99% of an entire length of a protein comprising amino acids 19-1341 of SEQ ID NO: 8; (c) a nucleic acid sequence that encodes a protein that is at least 95%, 96%, 97%, 98% or 99% identical to amino acids 19-1341 of SEQ ID NO: 8; and (d) a nucleic acid sequence that encodes a fragment comprising at least 90%, 91%, 92%, 93%, 94%, 95%, 96%, 97%, 98% or 99% of an entire length of a protein that is at least 95%, 96%, 97%, 98% or 99% identical to amino acids 19-1341 of SEQ ID NO: 8. In some embodiments, nucleic acid molecules comprising one or more nucleic acid sequences selected from the group consisting of: (a) a nucleic acid sequence that encodes SEQ ID NO: 8; (b) a nucleic acid sequence that encodes a fragment comprising at least 90%, 91%, 92%, 93%, 94%, 95%, 96%, 97%, 98% or 99% of an entire length of SEQ ID NO: 8; (c) a nucleic acid sequence that encodes a protein that is at least 95%, 96%, 97%, 98% or 99% identical to SEQ ID NO: 8; and (d) a nucleic acid sequence that encodes a fragment comprising at least 90% of an entire length of a protein that is at least 95%, 96%, 97%, 98% or 99% identical to SEQ ID NO: 8 are provided.

Isolated nucleic acid molecules comprising the above-described heterologous sequences may be incorporated into vectors such as plasmids, viral vectors and other forms of nucleic acid molecules as described below.

Protein molecules comprising the above described heterologous amino acid sequences are provided. Protein molecules consisting of the above described heterologous amino acid sequences are provided. Provided herein are proteins and polypeptides having the above-described sequences. The proteins and polypeptide may be referred to as MUC16 antigens and MUC16 immunogens. MUC16 antigens are capable of eliciting an immune response against tumors expressing a MUC16 antigen. In some embodiments, proteins comprising the amino acid sequence selected from the group consisting of: (a) amino acids 19-1490 of SEQ ID NO: 2; (b) a fragment comprising at least 90%, 91%, 92%, 93%, 94%, 95%, 96%, 97%, 98% or 99% of an entire length of a protein comprising amino acids 19-1490 of SEQ ID NO: 2; (c) an amino acid sequence that is at least 95%, 96%, 97%, 98% or 99% identical to amino acids 19-1490 of SEQ ID NO: 2; and (d) a fragment comprising at least 90%, 91%, 92%, 93%, 94%, 95%, 96%, 97%, 98% or 99% of an entire length of an amino acid sequence that is at least 95%, 96%, 97%, 98% or 99% identical to amino acids 19-1490 of SEQ ID NO: 2. In some embodiments, proteins comprising the amino acid sequence selected from the group consisting of: (a) SEQ ID NO: 2; (b) a fragment comprising at least 90% of an entire length of SEQ ID NO: 2; (c) an amino acid sequence that is at least 95%, 96%, 97%, 98% or 99% identical to SEQ ID NO: 2; and (c) a fragment comprising at least 90% of an entire length of an amino acid sequence that is at least 95%, 96%, 97%, 98% or 99% identical to SEQ ID NO: 2 are provided. In some embodiments, the protein comprises the amino acid sequence set forth in SEQ ID NO: 2.

In some embodiments, proteins comprising the amino acid sequence selected from the group consisting of: (a) amino acids 19-642 of SEQ ID NO: 4; (b) a fragment comprising at least 90%, 91%, 92%, 93%, 94%, 95%, 96%, 97%, 98% or 99% of an entire length of a protein comprising amino acids 19-642 of SEQ ID NO: 4; (c) an amino acid sequence that is at least 95%, 96%, 97%, 98% or 99% identical to amino acids 19-642 of SEQ ID NO: 4; and (d) a fragment comprising at least 90%, 91%, 92%, 93%, 94%, 95%, 96%, 97%, 98% or 99% of an entire length of an amino acid sequence that is at least 95%, 96%, 97%, 98% or 99% identical to amino acids 19-642 of SEQ ID NO: 4. In some embodiments, proteins comprising the amino acid sequence selected from the group consisting of: (a) SEQ ID NO: 4; (b) a fragment comprising at least 90% of an entire length of SEQ ID NO: 4; (c) an amino acid sequence that is at least 95%, 96%, 97%, 98% or 99% identical to SEQ ID NO: 4; and (c) a fragment comprising at least 90% of an entire length of an amino acid sequence that is at least 95%, 96%, 97%, 98% or 99% identical to SEQ ID NO: 4 are provided. In some embodiments, the protein comprises the amino acid sequence set forth in SEQ ID NO: 4.

In some embodiments, proteins comprising the amino acid sequence selected from the group consisting of: (a) amino acids 19-710 of SEQ ID NO: 6; (b) a fragment comprising at least 90%, 91%, 92%, 93%, 94%, 95%, 96%, 97%, 98% or 99% of an entire length of a protein comprising amino acids 19-710 of SEQ ID NO: 6; (c) an amino acid sequence that is at least 95%, 96%, 97%, 98% or 99% identical to amino acids 19-710 of SEQ ID NO: 6; and (d) a fragment comprising at least 90%, 91%, 92%, 93%, 94%, 95%, 96%, 97%, 98% or 99% of an entire length of an amino acid sequence that is at least 95%, 96%, 97%, 98% or 99% identical to amino acids 19-710 of SEQ ID NO: 6. In some embodiments, proteins comprising the amino acid sequence selected from the group consisting of: (a) SEQ ID NO: 6; (b) a fragment comprising at least 90% of an entire length of SEQ ID NO: 6; (c) an amino acid sequence that is at least 95%, 96%, 97%, 98% or 99% identical to SEQ ID NO: 6; and (c) a fragment comprising at least 90% of an entire length of an amino acid sequence that is at least 95%, 96%, 97%, 98% or 99% identical to SEQ ID NO: 6 are provided. In some embodiments, the protein comprises the amino acid sequence set forth in SEQ ID NO: 6.

In some embodiments, proteins comprising the amino acid sequence selected from the group consisting of: (a) amino acids 19-642 and 650-1341 of SEQ ID NO: 8; (b) a fragment comprising at least 90%, 91%, 92%, 93%, 94%, 95%, 96%, 97%, 98% or 99% of an entire length of a protein comprising amino acids 19-642 and 650-1341 of SEQ ID NO: 8; (c) an amino acid sequence that is at least 95%, 96%, 97%, 98% or 99% identical to amino acids 19-642 and 650-1341 of SEQ ID NO: 8; and (d) a fragment comprising at least 90%, 91%, 92%, 93%, 94%, 95%, 96%, 97%, 98% or 99% of an entire length of an amino acid sequence that is at least 95%, 96%, 97%, 98% or 99% identical to amino acids 19-642 and 650-1341 of SEQ ID NO: 8. In some embodiments, proteins comprising the amino acid sequence selected from the group consisting of: (a) amino acids 19-1341 of SEQ ID NO: 8; (b) a fragment comprising at least 90%, 91%, 92%, 93%, 94%, 95%, 96%, 97%, 98% or 99% of an entire length of a protein comprising amino acids 19-1341 of SEQ ID NO: 8; (c) an amino acid sequence that is at least 95%, 96%, 97%, 98% or 99% identical to amino acids 19-1341 of SEQ ID NO: 8; and (d) a fragment comprising at least 90%, 91%, 92%, 93%, 94%, 95%, 96%, 97%, 98% or 99% of an entire length of an amino acid sequence that is at least 95%, 96%, 97%, 98% or 99% identical to amino acids 19-1341 of SEQ ID NO: 8. In some embodiments, proteins comprising the amino acid sequence selected from the group consisting of: (a) SEQ ID NO: 8; (b) a fragment comprising at least 90% of an entire length of SEQ ID NO: 8; (c) an amino acid sequence that is at least 95%, 96%, 97%, 98% or 99% identical to SEQ ID NO: 8; and (c) a fragment comprising at least 90% of an entire length of an amino acid sequence that is at least 95%, 96%, 97%, 98% or 99% identical to SEQ ID NO: 8 are provided. In some embodiments, the protein comprises the amino acid sequence set forth in SEQ ID NO: 8.

In one aspect, it is desired that the consensus antigen provides for improved transcription and translation, including having one or more of the following: low GC content leader sequence to increase transcription; mRNA stability and codon optimization; and, to the extent possible, elimination of cis-acting sequence motifs (i.e., internal TATA-boxes).

The MUC16 antigen can be a consensus antigen (or immunogen) sequence derived from two or more species. In some embodiments, the consensus antigen may comprise a MUC16 ectodomain and transmembrane domain. The MUC16 consensus antigen can comprise one or more mutations in the ectodomain and/or transmembrane domain. The one or more mutations can include a substitution of one or more of the amino acids that are involved in N-glycosylation. The one or more mutations may comprise a substitution of asparagine to alanine. Accordingly, in some embodiments, the one or more mutations can replace 1, 2 or 3 amino acids in the MUC16 ectodomain and/or transmembrane domain.

In some embodiments, the MUC16 antigen can further comprise any combination of one or more repeat micro-consensus (RMC) sequences derived from native RMC sequences, for example, RMC1, RMC2, RMC3, and/or RMC4. In some embodiments, the MUC16 antigen can comprise any combination of one or more native repeat (R) sequences, for example, R59, R61, R62 and/or R63. In some embodiments, the MUC16 antigen comprises RMC1, RMC2, RMC3, RMC4, R61, R62 and R63 sequences. In some embodiments, the MUC16 antigen comprises RMC1, RMC2, RMC3, RMC4, R59, R61, R62 and R63 sequences. In some embodiments, the MUC16 antigen comprises RMC1, RMC2, RMC3 and RMC4 sequences. In some embodiments, the MUC16 antigen comprises R61, R62 and R63 sequences.

The MUC16 antigen can comprise modifications for improved expression. Modification can include codon optimization, RNA optimization, addition of a kozak sequence (e.g., GCC ACC) for increased translation initiation and/or the addition of an immunoglobulin leader sequence to increase the immunogenicity of the MUC16 antigen. The MUC16 antigen can comprise a signal peptide such as an immunoglobulin signal peptide, for example, but not limited to, an immunoglobulin E (IgE) or immunoglobulin G (IgG) signal peptide.

The MUC16 antigen can comprise modifications for epitope optimization. In some embodiments, a cleavage site such may be inserted between RMC sequences, between R sequences, or at the interface of RMC or R sequences. The cleavage site may be a furin cleavage site. In certain embodiments, a furin cleavage site may be inserted between RMC4 and R61.

Vaccine in Combination with Immune Checkpoint Inhibitor

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as WIC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune checkpoint inhibitor can be an antibody, a variant thereof, a fragment thereof, or a combination thereof.

a. Immune Checkpoint Molecule

The immune checkpoint molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

(1) PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and onn T cells and B cells upon TCR and B cell receptor signaling. PD-L1 is expressed by many tumor cell lines, including myelomas, mastocytomas, and melanomas.

b. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

(1) PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

(2) PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Vector

The vaccine can comprise one or more vectors that include a heterologous nucleic acid encoding the MUC16 antigen. The one or more vectors can be capable of expressing the antigen in a quantity effective to elicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome or yeast artificial chromosome. The vector can be either a self-replicating extra chromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

The vectors may comprise nucleic acid sequences operably linked to a regulatory element selected from a promoter and a poly-adenylation signal. In some embodiments, the promoter is a human cytomegalovirus immediate-early promoter (hCMV promoter). In some embodiments, the poly-adenylation signal is a bovine growth hormone poly-adenylation signal (bGH polyA).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence as well as sequences for cloning and subcloning the vector and fragments thereof. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

The vector can be a plasmid. The plasmid may be useful for transfecting cells with nucleic acid encoding the antigen, which the transformed host cells is cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants consensus proteins.

In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate-early promoter (hCMV promoter), Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, human β-globin polyadenylation signal or a bovine growth hormone poly-adenylation signal (bGH polyA). The SV40 polyadenylation signal may be a polyadenylation signal from a pCEP4 plasmid (Invitrogen, San Diego, CA).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be p V AXI, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an immunoglobulin (Ig) leader sequence. The leader sequence may be 5" of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E.coli*). The plasmid may also be pYES2 (Invitrogen, San Diego, Calif), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells. The plasmid may also be pGX001 (Inovio), which is modified from pVAX1 (Thermo Fisher Scientific, Waltham, MA).

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing the vector that comprises the nucleic acid molecule encoding MUC16 antigen discussed herein. The vector, after the final subcloning step into the mammalian expression plasmid, can be used to inoculate a cell culture in a large scale fermentation tank, using known methods in the art.

The vector for use with the electroporation devices, which are described below in more detail, can be formulated or manufactured using a combination of known devices and techniques, but preferably they are manufactured using an optimized plasmid manufacturing technique that is described in US Publication No. 2009/004716, which was filed on May 23, 2008. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced publication and patent, US Publication No. 2009/004716 and U.S. Pat. No. 7,238,522, respectively, are hereby incorporated in their entirety.

Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or are delivered as proteins in combination with the plasmid above in the vaccine. The one or more adjuvants may be selected from the group consisting of: CCL20, α-interferon (IFN-α), (β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, IL-31, IL-33, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFIβ, GM-CSF, epidermal growth factor (EGF), IL-1, IL-2, IL-4, IL-5, IL-6, IL-10, IL-12, IL-18, or a combination thereof.

In some embodiments the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No 61/569600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USIO/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DRS and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the antigen-encoding vector at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of nucleic acid. In some preferred embodiments, vaccine can contain about 10 nanograms to about 800 micrograms of nucleic acid. In some preferred embodiments, the vaccine can contain about 0.1 to about 500 micrograms of nucleic acid. In some preferred embodiments, the vaccine can contain about 1 to about 350 micrograms of nucleic acid. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the nucleic acid molecule of the vaccine. In some embodiments, pharmaceutical compositions according to the present invention comprise about 25 ng to about 5 mg of the nucleic acid molecule of the vaccine. In some embodiments, the pharmaceutical compositions contain about 50 ng to about 1 mg of the nucleic acid molecule of the vaccine. In some embodiments, the pharmaceutical compositions contain about 0.1 to about 500 micrograms of the nucleic acid molecule of the vaccine. In some embodiments, the pharmaceutical compositions contain about 1 to about 350 micrograms of the nucleic acid molecule of the vaccine. In some embodiments, the pharmaceutical compositions contain about 5 to about 250 micrograms of the nucleic acid molecule of the vaccine. In some embodiments, the pharmaceutical compositions contain about 10 to about 200 micrograms of the nucleic acid molecule of the vaccine. In some embodiments, the pharmaceutical compositions contain about 15 to about 150 micrograms of the nucleic acid molecule of the vaccine. In some embodiments, the pharmaceutical compositions contain about 20 to about 100 micrograms of the nucleic acid molecule of the vaccine. In some embodiments, the pharmaceutical compositions contain about 25 to about 75 micrograms of the nucleic acid molecule of the vaccine. In some embodiments, the pharmaceutical compositions contain about 30 to about 50 micrograms of the nucleic acid molecule of the vaccine. In some embodiments, the pharmaceutical compositions contain about 35 to about 40 micrograms of the nucleic acid molecule of the vaccine. In some embodiments, the pharmaceutical compositions contain about 100 to about 200 micrograms of the nucleic acid molecule of the vaccine. In some embodiments, the pharmaceutical compositions comprise about 10 micrograms to about 100 micrograms of the nucleic acid molecule of the vaccine. In some embodiments, the pharmaceutical compositions comprise about 20 micrograms to about 80 micrograms of the nucleic acid molecule of the vaccine. In some embodiments, the pharmaceutical compositions comprise about 25 micrograms to about 60 micrograms of the nucleic acid molecule of the vaccine. In some embodiments, the pharmaceutical compositions comprise about 30 ng to about 50 micrograms of the nucleic acid molecule of the vaccine. In some embodiments, the pharmaceutical compositions comprise about 35 ng to about 45 micrograms of the nucleic acid molecule of the vaccine. In some preferred embodiments, the pharmaceutical compositions contain about 0.1 to about 500 micrograms of the nucleic acid molecule of the vaccine. In some preferred embodiments, the pharmaceutical compositions contain about 1 to about 350 micrograms of the nucleic acid molecule of the vaccine. In some preferred embodiments, the pharmaceutical compositions contain about 25 to about 250 micrograms of the nucleic acid molecule of the vaccine. In some preferred embodiments, the pharmaceutical compositions contain about 100 to about 200 micrograms of the nucleic acid molecule of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of the nucleic acid molecule of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of the nucleic acid molecule of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng of the nucleic acid molecule of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of the nucleic acid molecule of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of the nucleic acid molecule of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition can further comprise a pharmaceutically acceptable excipient as provided above. For example, the pharmaceutically acceptable excipient can comprise the functional molecules, vehicles, adjuvants, carriers, diluents, or transfection facilitating agents, as provided above.

Methods of Vaccination

Provided herein are methods for treating and/or preventing MUC16-expressing cancer, such as but not limited to ovarian cancer, using the pharmaceutical formulations described above. Also described herein are methods of using the pharmaceutical formulations described above in the treatment and/or prevention of MUC16-expressing cancer, such as but not limited to ovarian cancer, in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the cell and delivered to the surface of the cell, whereupon the immune system recognizes and induces a cellular, humoral, or cellular and humoral response. The administration of the vaccine can be used to induce or elicit an immune response in subjects against MUC16 by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the the nucleic acid molecule of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Method of Generating an Immune Response with the Vaccine

The vaccine can be used to generate an immune response in a mammal or non-mammal subject, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the MUC16 antigens as described above, which embodiments comprise administering the vaccine. Some embodiments provide methods of therapeutically vaccinating a subject that has been suffering from the ovarian cancer or tumor expressing MUC16, which embodiments comprise administering the vaccine. Diagnosis of the ovarian cancer or tumor expressing the one or more MUC16 antigens as disclosed herein prior to administration of the vaccine can be done routinely.

Method of Cancer Treatment with the Vaccine

The vaccine can be used to generate or elicit an immune response in a mammal that is reactive or directed to MUC16-expressing cancer, such as but not limited to ovarian cancer, more particularly epithelial ovarian cancer, most particularly serous ovarian cancer. The elicited immune response can prevent ovarian cancer or tumor growth.

The elicited immune response can prevent and/or reduce metastasis of cancerous or tumor cells in a subject with ovarian cancer. Accordingly, the vaccine can be used in a method that treats and/or prevents cancer or tumors in the mammal or subject with cancer that is administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-γ and TFN-α or preferably all of the aforementioned. The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, PA) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

Methods of Preparing the Vaccine

Provided herein are methods for preparing the DNA plasmids discussed herein. The DNA plasmids, after the final subcloning step into the mammalian expression plasmid, can be used to inoculate a cell culture in a large scale fermentation tank, using known methods in the art.

The DNA plasmids for use with the electroporation devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, US Ser. No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: MUC16 Central Tandem Repeat Domain Design Strategy

Figure 1:
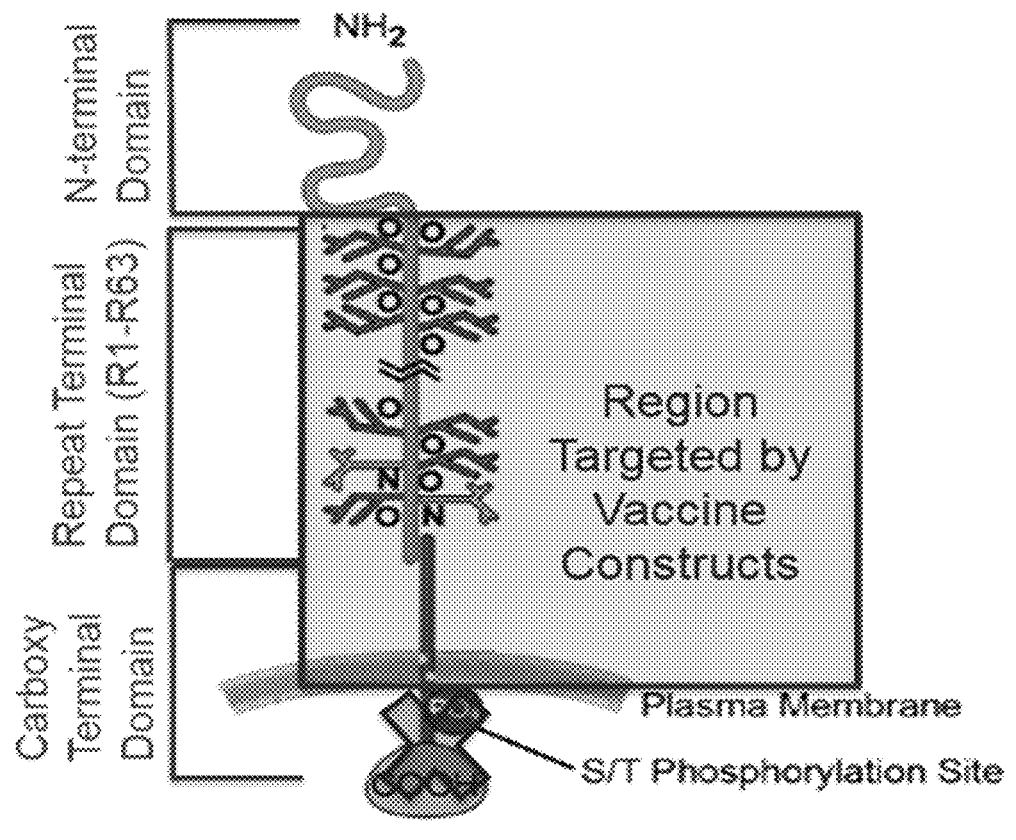

Native human MUC16 is a large, heavily glycosylated protein that is 22,152 amino acids in length. It is composed of 3 domains: the N-terminal domain, the central tandem repeat domain, and the carboxy terminal domain. Since the native human MUC16 N-terminal domain is very large (12,068 amino acids), and lacks repetitive sequence, only the central tandem repeat and carboxy terminal domains were targeted (FIG. 1). Different design strategies were applied to the tandem repeat and carboxy terminal domains.

Figure 3:
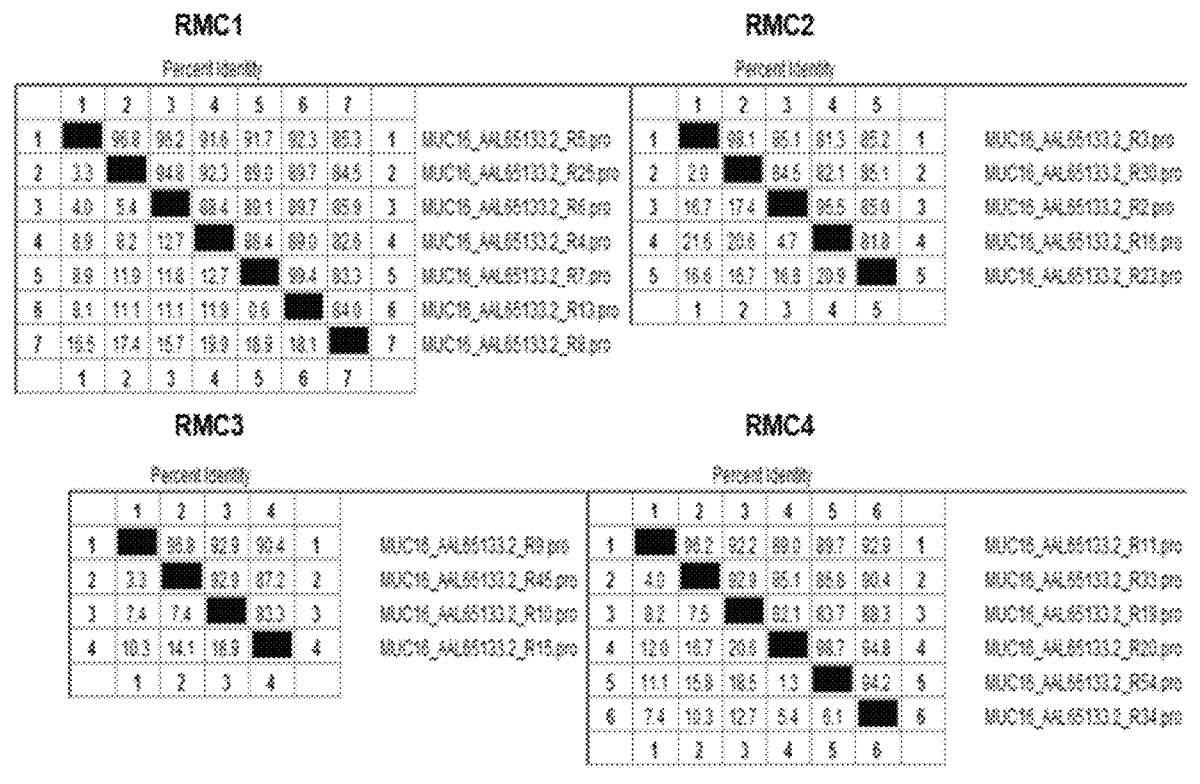

The native human MUC16 central tandem repeat domain, which is 9,799 amino acids in length, is a series of 63 homologous repeats that are each 156 amino acids, except for the last repeat, which is only 127 amino acids. Due to its length and lack of homology among various species, repeat micro-consensus (RMC) sequences were derived from multiple human native repeat sequences in order to potentially elicit cross-reactive T cells against the majority of human native repeats. Briefly, after excluding low quality native human repeat sequences, the remaining 34 native human repeat sequences were used to perform phylogenetic analysis (FIG. 2 and FIG. 3). The result indicated that these sequences could be clustered into four groups of repeats that share >80% identity with one another. Based on previous T-cell-based vaccine development experience, each micro-consensus sequence should be derived from sequences that share >80% sequence identity with each other in order to elicit cross-reactive T cell responses against the native repeats used to generate this micro-consensus. As a result, four RMC sequences were generated.

Among those repeats that were not grouped into any of these four groups, only three other native repeats (R61-63) shared <80% sequence identity with all four generated repeat micro-consensus (RMC) sequences (Table 1). Table 1 shows the percent sequence identity of all ungrouped native MUC16 individual repeat sequences (R14, R1, R55, R56, R21, R58, R22, R59, R60, R61, R63, and R62) with RMC1-4. Bold font indicates that the remaining ungrouped native repeat sequences share ≥80% percent identity with at least one RMC, except for R61, R62, and R63 (GenBank: AAL65133.2).

TABLE 1

|       | 14  | 1   | 55  | 56  | 21  | 58  | 22  | 59  | 60  | 61  | 63  | 62  |
|-------|-----|-----|-----|-----|-----|-----|-----|-----|-----|-----|-----|-----|
| MC #1 | 7.2 | 9.4 | 5.2 | 0.6 | 1.8 | 0.6 | 3.1 | 3.9 | 8.7 | 4.7 | 8.4 | 5.5 |
| MC #2 | 5.3 | 0.6 | 7.7 | 3.9 | 3.8 | 0.6 | 3.1 | 3.9 | 0.0 | 6   | 0   | 5.5 |
| MC #3 | 7.6 | 0.3 | 5.5 | 5.5 | 6.6 | 6.8 | 9.9 | 9.4 | 5.5 | 0.8 | 4.8 | 7   |
| MC #4 | 7.6 | 4.8 | 3.2 | 9.4 | 2.5 | 0.0 | 3.1 | 2.6 | 8.7 | 7.9 | 1.6 | 7.7 |

In order to potentially increase the breadth of vaccine-induced T-cell responses, these three repeats were included in the MUC16 central tandem repeat domain design as individual elements. The rest of the native repeats (R1, R14, R55, R56, R21, R58, R22, R59, and R60) share ≥80% sequence identity with at least one RMC, and should be covered by at least one of the four RMC sequences.

In summary, a synthetic consensus design approach was not used to target the central tandem repeat domain. Instead, 4 RMC sequences, derived from multiple human native repeat sequences, were generated in order to potentially elicit cross-reactive T cells against the majority of human native repeats. Each RMC was derived from repeat sequences that share >80% sequence identity with each other. Native repeats R61, R62, and R63, which all share <80% sequence identity with all 4 RMC sequences, were also included in the MUC16 central tandem repeat domain design, as individual elements, in order to potentially increase the breadth of vaccine-induced T-cell responses.

Example 2: MUC16 Carboxy Terminal Domain Design Strategy

Figure 4:
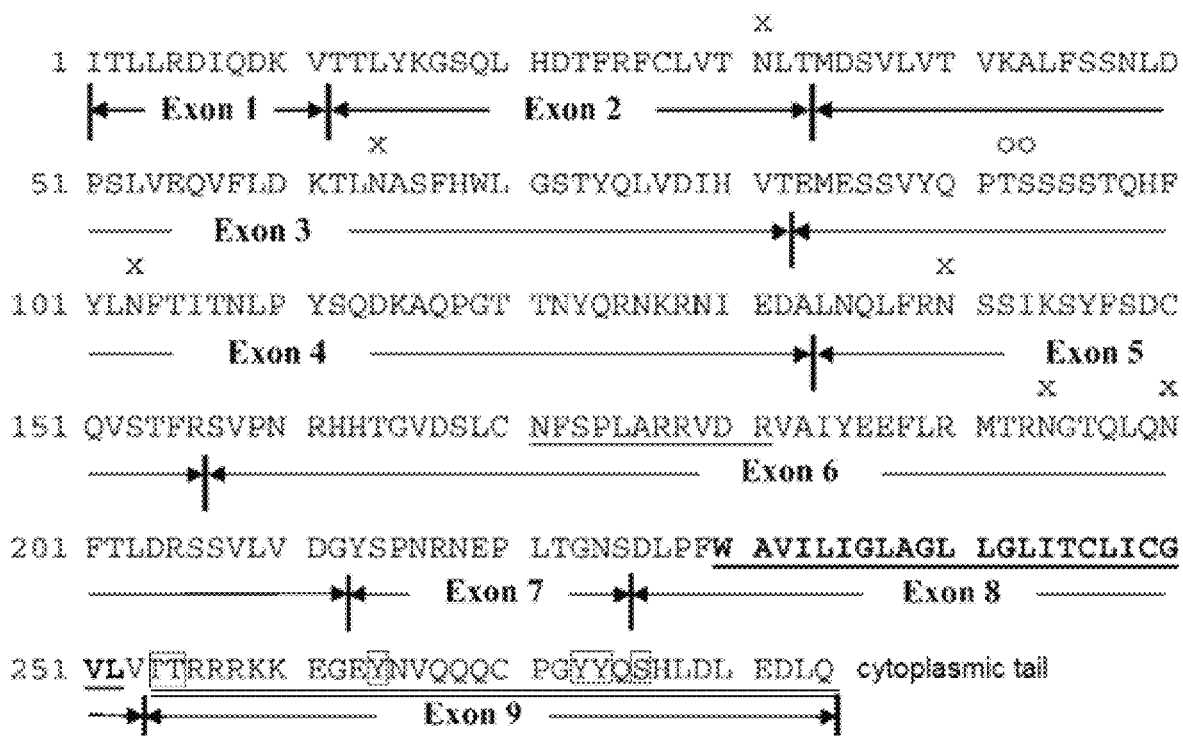
FIG. 4 shows the amino acid sequence of the MUC16 carboxy terminal domain (SEQ ID NO: 10). The underlined region (NFSPLARRVDR (SEQ ID NO: 9)) is a potential cleavage site, the bold underlined region is the transmembrane domain, and the cytoplasmic tail is indicated by double underlining. Unspecified sequence upstream of the transmembrane domain is the extracellular ectodomain. Boxes denote potential S/T/Y phosphorylation sites. N- and O-glycosylation sites are indicated with an X and O, respectively.

The carboxy terminal domain of native human MUC16 is 284 amino acids in length and consists of an extracellular ectodomain, a transmembrane domain, and a short cytoplasmic tail. Unlike the central tandem repeat domain, the carboxy terminal domain is well conserved among many species. However, the cytoplasmic tail of MUC16 contains multiple potential S/T/Y phosphorylation sites, suggesting the involvement of MUC16 in signal transduction pathway (s) (FIG. 4). In FIG. 4, boxes denote potential S/T/Y phosphorylation sites. N- and O-glycosylation sites are indicated with an X and 0, respectively. O'Brien, T. J. et al. *Tumour biology: Journal of the International Society for Oncodevelopmental Biology and Medicine* 22, 348-366 (2001). To prevent unwanted triggering of downstream signaling, the cytoplasmic tail (amino acids 254-284 of the native carboxy-terminal domain) was not included in any of the MUC16 immunogens.

Generation of Consensus MUC16 Ectodomain and Transmembrane Domain

A human consensus MUC16 carboxy terminal domain lacking the cytoplasmic tail was constructed using 21 MUC16 ectodomain and transmembrane domain sequences from GenBank (www.ncbi.nlm.nih.gov/genbank/). The GenBank accession numbers of these sequences are: AAL65133.2, XP_004059993.1, XP_014197952.1, XP_003914869.1, XP_007993338.1, XP_011739103.1, XP_011932759.1, XP_011810358.1, XP_015296314.1, XP_010387164.1, XP_008985417.1, XP_010347904.1, XP_012291241.1, XP_011287799.1, XP_003354138.3, XP_014410271.1, XP_015096370.1, XP_011373099.1, XP_011226599.1, XP_008703704.1, and XP_0124966751

The consensus sequence was generated using the DNAS-TAR® Lasergene software package (version 13.0.0.357). The MUC16 ectodomain and transmembrane domain sequences were imported into MegAlign and aligned using the ClustalW multiple sequence alignment program. The resulting MUC16 ectodomain and transmembrane domain sequence was determined to share 96.0%-96.4% identity with human native MUC16 ectodomain and transmembrane domain.

Rationale for Introduction of Mutations in Carboxy Terminal Domain to Abolish Biological Function of MUC16

After the consensus MUC16 ectodomain and transmembrane domain was generated, three asparagine (N) to alanine (A) mutations (N→A) were introduced to abolish biological function of the resulting consensus MUC16 ectodomain and transmembrane domain protein. These three mutations were introduced because the carboxy-terminal ectodomain of MUC16 has been implicated in promoting tumorigenesis, tumor invasion, and metastasis. Rao, T. D. et al. *PloS one* 10 (2015). Rao et al. showed that introducing these three N→A mutations in the ectodomain of MUC16 to abolish N-glycosylation dramatically reduced ERK1/2 and AKT phosphorylation and in vivo tumor growth in athymic nude mice engrafted with transfected 3T3 fibroblast cells. Abolition of the biological function following the introduction of the 3 N→A mutations in synthetic consensus MUC16 constructs were not assessed in vitro or in vivo.

MUC16 Carboxy Terminal Domain Design Summary

A consensus MUC16 ectodomain and transmembrane domain was generated and three mutations (N→A) were introduced to abolish N-glycosylation (FIG. 5). The modified consensus MUC16 ectodomain and transmembrane domain shares 95.3% identity with human native MUC16 ectodomain and transmembrane domain. Table 2 shows the percent sequence homology of the generated MUC16 ectodomain and transmembrane domain with human native MUC16 ectodomain and transmembrane domain.

TABLE 2

| Divergence | Percent Identity | | | |
|---|---|---|---|---|
| | | 1 | 2 | |
| | 1 | | 95.3 | 1 |
| | 2 | 4.9 | | 2 |
| | | 1 | 2 | |

1 = Consensus MUC16 ectodomain and transmembrane domain
2 = Human native MUC16 ectodomain and transmembrane domain

Figure 6A:
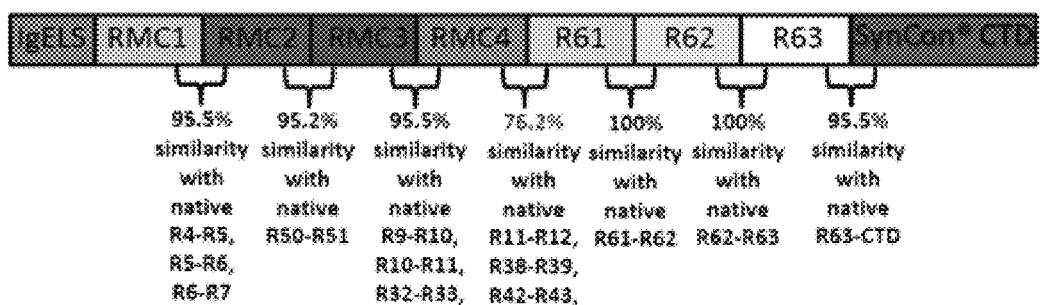
FIGS. 6A-6B illustrate the strategy for assembling RMCs, native repeats and synthetic consensus MUC16 ectodomain and transmembrane domain to reduce the likelihood of off-target epitopes.
Figure 6B:
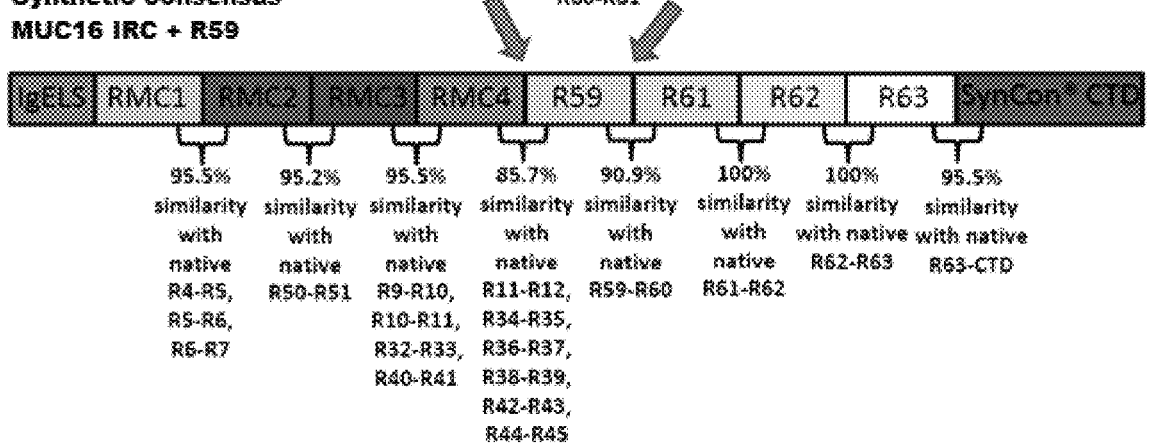

Example 3: Strategy for Assembling RMCs, Native Repeats, and Synthetic Consensus MUC16 Ectodomain and Transmembrane Domain (CTD) to Reduce Likelihood of Introducing Off-Target Epitopes The elements to be included in the MUC16 design included four RMCs, three native repeats and a synthetic consensus MUC16 ectodomain and transmembrane domain (CTD). The initial design strategy was to generate a MUC16 immunogen (preliminary synthetic MUC16 immunogen) by incorporating the elements as shown in FIGS. 6A-6B. However, since RMC1-RMC2, RMC2-RMC3, RMC3-RMC4, RMC4-R61, and R63-synthetic consensus MUC16 ectodomain and transmembrane domain junctions in this immunogen do not occur in the native MUC16 sequence, it is possible that non-relevant, off-target epitopes could potentially be introduced if these junctions do not share high sequence identity with at least one native MUC16 repeat junction. In order to determine the sequence identity of the synthetic immunogen junctions with all of MUC16's native repeat junctions, the last 11 amino acids and beginning 11 amino acids of all neighboring native repeats were aligned to the last 11 amino acids and beginning 11 amino acids of all neighboring synthetic immunogen junctions (RMC1-RMC2, RMC2-RMC3, RMC3-RMC4, RMC4-R61, and R63-synthetic consensus CTD). The analysis result indicated that all synthetic immunogen junctions shared >95.2% sequence identity with at least one native repeat junction except for the RMC4-R61 synthetic immunogen junction, which only shared up to 76.2% sequence identity with all native repeat junctions (FIG. 6A).

In order to reduce the likelihood of off-target epitopes being introduced in the RMC4-R61 junction sequence, the native MUC16 repeat 59 (R59) was inserted between RMC4 and R61 (synthetic consensus IRC+R59 immunogen) (FIG. 6B). Sequence analysis showed that the RMC4-R59 and R59-R61 junctions shared higher identities with native repeat junctions (85.7% and 90.9%, respectively) compared to a RMC4-R61 junction. Moreover, MHC class I epitope prediction, using the Immune Epitope Database Resource Analysis Resource (//tools.iedb.org/mhci/), predicted no strong binders of the HLA-A*02:01 haplotype at the RMC4-R59 and R59-R61 junctions.

Figure 7:
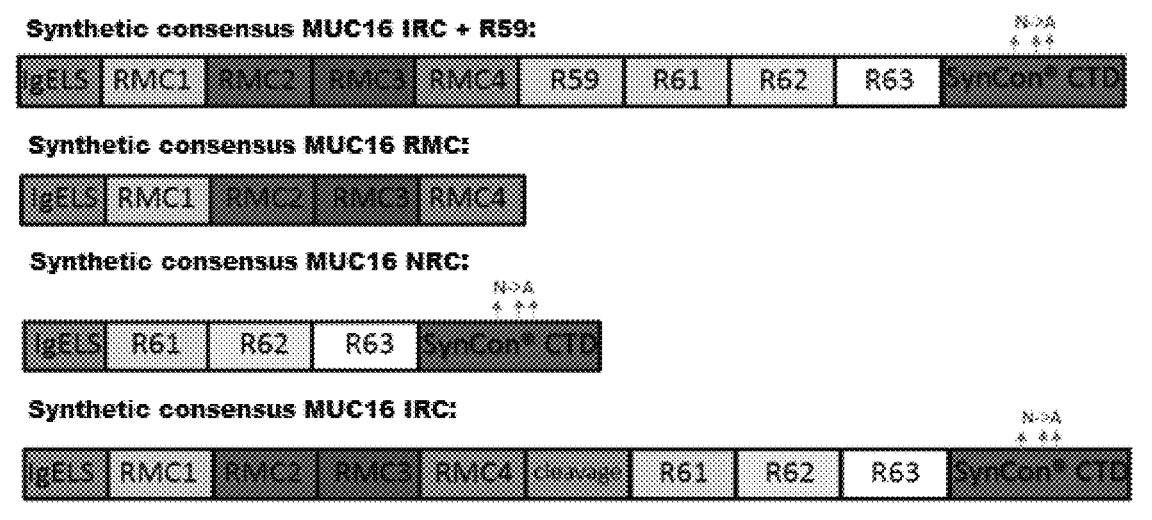

Additional strategies to avoid introducing a RMC4-R61 junction were also utilized, including: using two plasmids (one to express a RMC1-RMC4 immunogen and the other to express a R61, R62, R63, and synthetic consensus MUC16 CTD immunogen), adding a furin cleavage site between RMC4 and native R61 of the preliminary synthetic immungen, and using a dual-promoter expression vector with one promoter (hCMV) driving expression of the RMC1-RMC4 immunogen and the other promoter (sCMV) driving expression of the R61, R62, R63, and synthetic consensus MUC16 CTD immunogen. As a result, five different synthetic consensus MUC16 DNA plasmids were generated as shown in Table 3. Schematic representations of the synthetic consensus MUC16 immunogens are shown in FIG. 7.

TABLE 3

| Plasmid ID | Backbone | Name of Immunogen(s) | Definitions |
|---|---|---|---|
| pGX1435 | pGX0001 | Synthetic consensus MUC16 IRC + R59 | IRC + R59: Integrated Repeats and Synthetic Consensus Carboxy Terminal Domain + Native Repeat 59 |
| pGX1436 | pGX0001 | Synthetic consensus MUC16 RMC | RMC: Repeat Micro-Consensus |
| pGX1437 | pGX0001 | Synthetic consensus MUC16 NRC | NRC: Native Repeats and Synthetic Consensus Carboxy Terminal Domain |
| pGX1438 | pGX0001 | Synthetic consensus MUC16 IRC | IRC: Integrated Repeats & Synthetic Consensus Carboxy Terminal Domain |
| pGX1439 | pGX0003 (dual-promoter) | Synthetic consensus MUC16 RMC & synthetic consensus MUC16 NRC | See above |

To have a higher level of expression, upstream Kozak and IgE leader sequences were added to the N-terminus of all four synthetic consensus MUC16 immunogens. Yang, J. S. et al., *The Journal of infectious diseases* 184, 809-816 (2001). Furthermore, the codon usage of the DNA sequences encoding these immunogens were adapted to the codon bias of Homo sapiens genes. Andre, S. et al. *Journal of virology* 72, 1497-1503 (1998); Deml, L. et al. *Journal of virology* 75, 10991-11001 (2001).

In addition, RNA optimization was also performed: regions of very high (>80%) or very low (<30%) GC content as well as cis-acting sequence motifs such as internal TATA boxes, chi-sites, and ribosomal entry sites were avoided. Schneider, R., et al., *Journal of virology* 71, 4892-4903 (1997); Muthumani, K. et al. *Virology* 314, 134-146 (2003). The synthesized synthetic consensus MUC16 immunogens were digested with either BamHI and XhoI (pGX1435-pGX1438) or either PmeI and XhoI or SalI and MluI (pGX1439), and cloned into either Inovio's expression vector pGX0001 (pGX1435-38) or Inovio's dual-promoter expression vector pGX0003 (pGX1439). For all synthetic consensus MUC16 plasmids, full length sequencing was done and then analyzed and confirmed by two analysts to be correct.

Figure 8A:
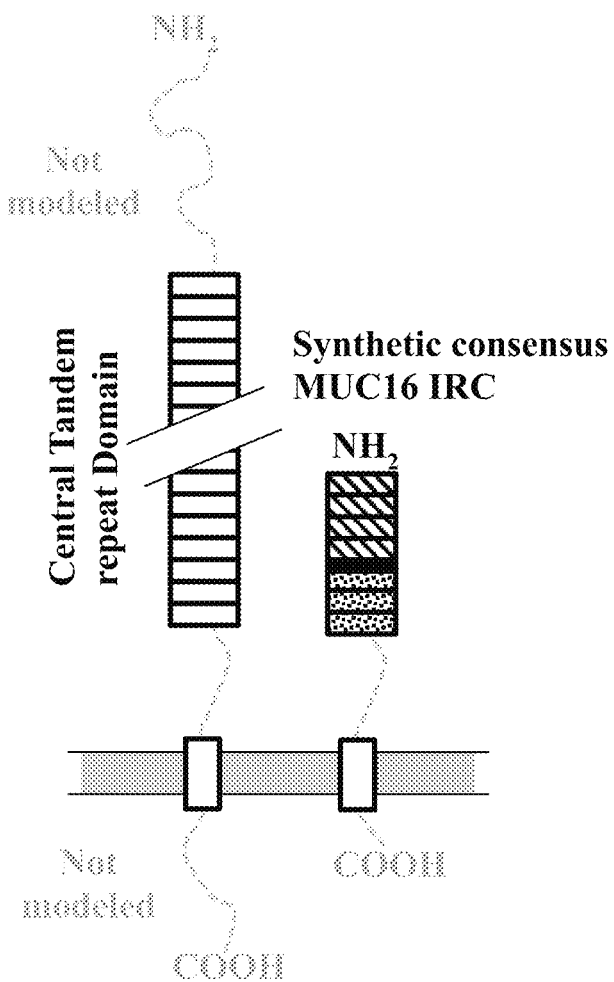

A representative comparative model of the central tandem repeat region of synthetic consensus MUC16 immunogens, based on the synthetic consensus MUC16 IRC sequence, is shown in FIGS. 8A-8C. FIG. 8A is a schematic diagram of native MUC16 (based on GenBank AAL65133.2) and synthetic consensus MUC16 IRC. Clear differences in size exist between the two molecules, and the native sequence contains additional domains not present in the synthetic consensus version. Both native MUC16 and synthetic consensus MUC16 IRC contain a series of Sea Urchin Sperm Protein, Enterokinase, and Agrin (SEA)-like repeats and a transmembrane domain. In synthetic consensus MUC16 IRC, the repeat sequences are based on the microconsensus sequence protocol described in the Central Tandem Repeat Design Strategy section. As shown in FIG. 8B, comparative modeling illustrates the size differences between the native MUC16 and synthetic consensus MUC16 IRC design. SEA-like repeat modules were modeled for both native MUC16 and synthetic consensus MUC16 IRC. Due to the size of the native sequence, modeling was performed at low resolution only and provided to convey relative size information. FIG. 8C shows a comparative model of synthetic consensus MUC16 IRC repeat region shown in cpk format. The large N-terminal region of MUC16, as well as the C-terminal region, do not contain sequences with reliable parental templates, which is why they could not be modeled.

The nucleotide sequence (SEQ ID NO: 1) and amino acid sequence (SEQ ID NO: 2) for synthetic consensus MUC16 IRC+R59 appear in Table 21 and Table 22, respectively. The nucleotide sequence (SEQ ID NO: 3) and amino acid sequence (SEQ ID NO: 4) for synthetic consensus MUC16 RMC appear in Table 23 and Table 24, respectively. The nucleotide sequence (SEQ ID NO: 5) and amino acid sequence (SEQ ID NO: 6) for synthetic consensus MUC16 NRC appear in Table 25 and Table 26, respectively. The nucleotide sequence (SEQ ID NO: 7) and amino acid sequence (SEQ ID NO: 8) for synthetic consensus MUC16 IRC appear in Table 27 and Table 28, respectively. An annotation of the elements of SEQ ID NO: 2, SEQ ID NO: 4, SEQ ID NO: 6 and SEQ ID NO: 8 and the corresponding amino acid positions is provided in Table 4.

TABLE 4

| Description | Amino acid position |
|---|---|
| SEQ ID NO: 2 Annotation (synthetic consensus MUC16 IRC + R59) | |
| IgE leader sequence | 1-18 |
| Repeat Micro-consensus 1 | 19-174 |
| Repeat Micro-consensus 2 | 175-330 |
| Repeat Micro-consensus 3 | 331-486 |
| Repeat Micro-consensus 4 | 487-642 |
| Native Repeat 59 | 643-798 |
| Native Repeat 61 | 799-954 |
| Native Repeat 62 | 955-1110 |
| Native Repeat 63 | 1111-1237 |
| Synthetic consesnsus MUC16 Carboxy Terminal Domain | 1238-1490 |
| Mutations to abolish N-glycosylation | N1408A |
| | N1431A |
| | N1437A |
| SEQ ID NO: 4 Annotation (synthetic consensus MUC16 RMC) | |
| IgE leader sequence | 1-18 |
| Repeat Micro-consensus 1 | 19-174 |
| Repeat Micro-consensus 2 | 175-330 |
| Repeat Micro-consensus 3 | 331-486 |
| Repeat Micro-consensus 4 | 487-642 |
| SEQ ID NO: 6 Annotation (synthetic consensus MUC16 NRC) | |
| IgE leader sequence | 1-18 |
| Native Repeat 61 | 19-174 |
| Native Repeat 62 | 175-330 |
| Native Repeat 63 | 331-457 |
| Synthetic consensus MUC16 Carboxy Terminal Domain | 458-710 |
| Mutations to abolish N-glycosylation | N628A |
| | N651A |
| | N657A |
| SEQ ID NO: 8 Annotation (synthetic consensus MUC16 IRC) | |
| IgE leader sequence | 1-18 |
| Repeat Micro-consensus 1 | 19-174 |
| Repeat Micro-consensus 2 | 175-330 |
| Repeat Micro-consensus 3 | 331-486 |
| Repeat Micro-consensus 4 | 487-642 |
| Furin cleavage site | 643-649 |
| Native Repeat 61 | 650-805 |
| Native Repeat 62 | 806-961 |
| Native Repeat 63 | 962-1088 |
| Synthetic consensus MUC16 Carboxy Terminal Domain | 1089-1341 |
| Mutations to abolish N-glycosylation | N1259A |
| | N1282A |
| | N1288A |

The differences between synthetic consensus MUC16 immunogens and native sequences are summarized in Table 5. Because the size of the central tandem repeat domain varies among species (human: 63 repeats, rhesus: 4 repeats; mouse: 15 repeats), and the size of the individual repeats varies greatly among species, it is challenging to accurately align full length synthetic MUC16 immunogen sequences with species-specific native sequences. Therefore, for the central tandem repeat domain, only the Sea Urchin Sperm Protein, Enterokinase, and Agrin (SEA) domain regions of the synthetic constructs were compared to native human, mouse, and rhesus SEA domain sequences since this region is the most conserved region of the repeat sequence.

TABLE 5

| Characteristics | Synthetic Consensus MUC16 IRC + R59 | Synthetic Consensus MUC16 RMC | Synthetic Consensus MUC16 NRC | Synthetic Consensus MUC16 IRC | Synthetic Consensus MUC16 - SEA Domains of RMC1-4 | Synthetic Consensus MUC16 - SEA Domains of R61-R63 | Synthetic Consensus MUC16 - Carboxy-Terminal Domain |
|---|---|---|---|---|---|---|---|
| Identity to native human MUC16 | | | | | 51.5%-100% | 100% | 95.3% |
| Identity to native rhesus MUC16 | | | | | 20.0% to 89.7% | 17.4% to 93.9% | 95.7% |
| Identity to native mouse MUC16 | | | | | 21.6% to 71.1% | 15.1% to 71.3% | 75.1% |
| Number of amino acid mutations (vs native human) | | | | | | 0 | 12 |

TABLE 5-continued

| Characteristics | Synthetic Consensus MUC16 IRC + R59 | Synthetic Consensus MUC16 RMC | Synthetic Consensus MUC16 NRC | Synthetic Consensus MUC16 IRC | Synthetic Consensus MUC16 - SEA Domains of RMC1-4 | Synthetic Consensus MUC16 - SEA Domains of R61-R63 | Synthetic Consensus MUC16 - Carboxy-Terminal Domain |
|---|---|---|---|---|---|---|---|
| Number of inserted mutations (not consensus derived) | 3 | 0 | 3 | 3 | 0 | 0 | 3 |
| Molecular weight | 1492 aa (164 Kda) | 644 aa (71 Kda) | 712 aa (78 Kda) | 1343 aa (148 Kda) | | | |
| Length of coding sequence (bp) | 4476 | 1932 | 2136 | 4029 | | | |

Example 4: Plasmid Construction and Structure pGX0001

Figure 9:
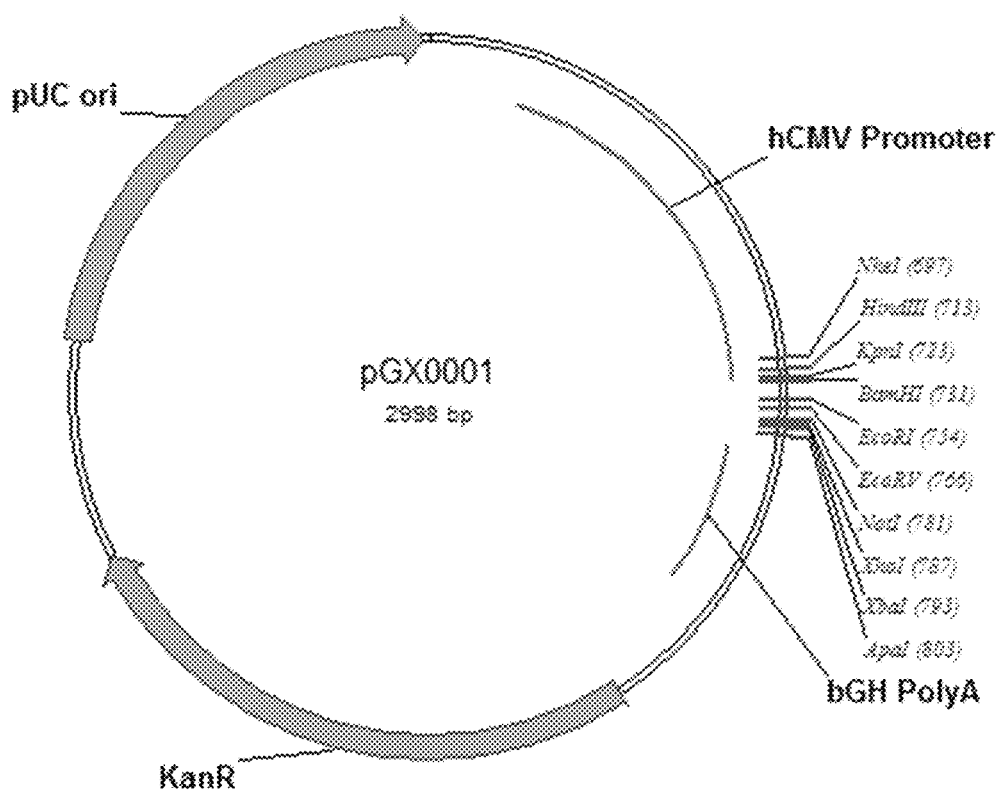
FIG. 9 is a diagrammatic representation of the modified pVAX1 backbone (pGX0001).

The vector backbone pGX0001 is a 2998 bp modified pVAX1 expression vector under the control of the human cytomegalovirus immediate-early promoter (hCMV promoter). The original pVAX1 was obtained from Thermo Fisher Scientific. The pGX0001 backbone includes the kanamycin resistance gene (KanR) and plasmid origin of replication (pUC ori) for production purpose. Those elements are not functional in eukaryotic cells. The map and description of the modified expression vector pVAX1 (pGX0001) are shown in FIG. 9 and Table 6, respectively.

TABLE 6

| Elements: | Base Pairs: |
|---|---|
| CMV Promoter: | 137-724 |
| T7 promoter/priming site | 664-683 |
| Multiple cloning site | 696-811 |
| Bovine GH polyadenylation signal | 829-1053 |
| Kanamycin resistance gene | 1226-2020 |
| pUC origin | 2319-2992 |

Modifications were introduced into pVAX1 to create pGX0001. These modifications are listed in Table 7, and no issues were detected regarding plasmid amplification and antigen transcription and translation. No further changes in the sequence of pGX0001 were observed in any of the plasmid products in the platform using pGX0001 as the backbone. Base pairs 2, 3 and 4 are changed from ACT to CTG in backbone, upstream of CMV promoter.

TABLE 7

| Modification | Base Pair | Description |
|---|---|---|
| C > G | 241 | in CMV promoter |
| C > T | 1158 | backbone, downstream of the bovine growth hormone polyadenylation signal (bGH polyA) |
| A > — | 2092 | backbone, downstream of the Kanamycin resistance gene |
| C > T | 2493 | in pUC origin of replication (pUC ori) |
| G > C | 2969 | in very end of pUC On upstream of RNASeH site | pGX0003

Figure 10:
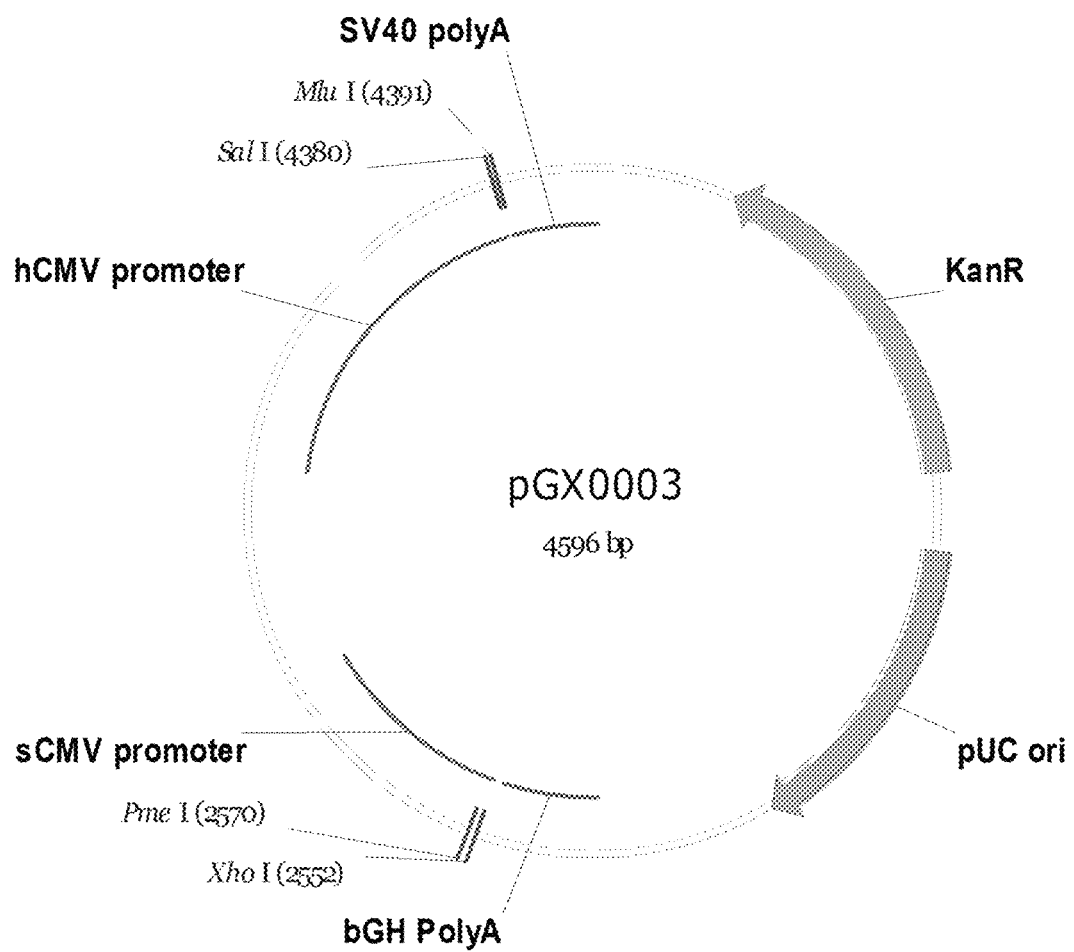
FIG. 10 is a diagrammatic representation of the pGX0003 backbone.

The vector backbone pGX0003 is a 4596 base pair eukaryotic expression plasmid with two multiple cloning sites for inserts under the control of two promoters: the hCMV promoter with an SV40 polyA signal and the sCMV promoter with a bGH polyA signal. This backbone also includes KanR and pUC ori. The map and description of pGX0003 are shown in FIG. 10 and Table 8, respectively.

TABLE 8

| Elements: | Base Pairs: |
|---|---|
| hCMV Promoter: | 3548-4373 |
| Simian Virus 40 polyadenylation signal | 4391-4596 |
| Scmv Promoter | 2558-3060 |
| Bovine GH polyadenylation signal | 2290-2528 |
| Kanamycin resistance gene | 298-1059 |
| pUC origin | 1227-1900 | pGX1435 pGX1435 was made by cloning the synthetic consensus MUC16 (synthetic consensus MUC16 IRC+R59) DNA sequence into pGX0001 at BamHI and XhoI sites. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. A schematic diagram of pGX1435 and synthetic consensus MUC16 IRC+R59 is presented in FIG. 11, and the elements of the plasmid and corresponding base pairs are presented in Table 9.

TABLE 9

Figure 12:
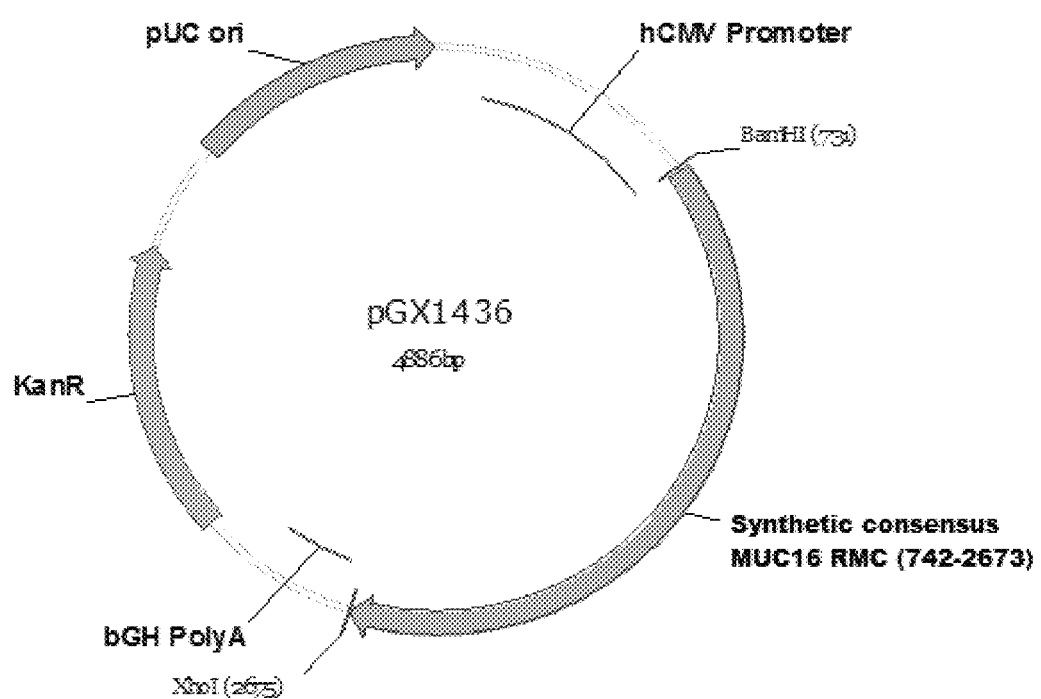
FIG. 12 is a diagrammatic representation of plasmid pGX1436 and synthetic consensus MUC16 RMC.

| Elements: | Base Pairs: |
|---|---|
| hCMV Promoter: | 137-724 |
| Synthetic consensus MUC16 IRC + R59 Coding Sequence: | 742-5217 |
| bGH PolyA: | 5261-5485 |
| Kanamycin Resistance (KanR): | 5658-6452 |
| pUC Ori: | 6751-7424 | pGX1436 pGX1436 was made by cloning the synthetic micro-consensus MUC16 (synthetic consensus MUC16 RMC) DNA sequence into pGX0001 at BamHI and XhoI sites. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. A schematic diagram of pGX1436 and synthetic consensus MUC16 RMC is presented in FIG. 12, and the elements of the plasmid and corresponding base pairs are presented in Table 10.

TABLE 10

| Elements: | Base Pairs: |
| --- | --- |
| hCMV Promoter: | 137-724 |
| Synthetic consensus MUC16 RMC Coding Sequence: | 742-2673 |
| bGH PolyA: | 2717-2941 |
| Kanamycin Resistance (KanR): | 3114-3908 |
| pUC Ori: | 4207-4880 | pGX1437 pGX1437 was made by cloning the synthetic consensus MUC16 (synthetic consensus MUC16 NRC) DNA sequence into pGX0001 at BamHI and XhoI sites. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. A schematic diagram of pGX1437 and synthetic consensus MUC16 NRC is presented in FIG. 13, and the elements of the plasmid and corresponding base pairs are presented in Table 11.

TABLE 11

| Elements: | Base Pairs: |
| --- | --- |
| hCMV Promoter: | 137-724 |
| Synthetic consensus MUC16 NRC Coding Sequence: | 742-2877 |
| bGH PolyA: | 2921-3145 |
| Kanamycin Resistance (KanR): | 3318-4112 |
| pUC Ori: | 4411-5084 | pGX1438 pGX1438 was made by cloning the synthetic consensus MUC16 (synthetic consensus MUC16 IRC) DNA sequence into pGX0001 at BamHI and XhoI sites. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. A schematic diagram of pGX1438 and synthetic consensus MUC16 IRC is presented in FIG. 14, and the elements of the plasmid and corresponding base pairs are presented in Table 12.

TABLE 12

| Elements: | Base Pairs: |
| --- | --- |
| hCMV Promoter: | 137-724 |
| synthetic consensus MUC16 IRC Coding Sequence: | 742-4770 |
| bGH PolyA: | 4814-5038 |
| Kanamycin Resistance (KanR): | 5211-6005 |
| pUC Ori: | 6304-6977 | pGX1439 pGX1439 was made by cloning the synthetic consensus MUC16 RMC DNA sequence into pGX0003 at the SalI and MluI sites and the synthetic consensus MUC16 NRC DNA sequence at the PmeI and XhoI sites.

pGX1439 is a dual-promoter DNA plasmid in which synthetic consensus MUC16 RMC-related mRNA production is driven by a human CMV promoter (hCMV Promoter) and is terminated by the simian virus 40 poly-adenylation signal (SV40 polyA) and in which synthetic consensus MUC16 NRC related-mRNA production is driven by a simian CMV promoter (sCMV Promoter) and is terminated by the bovine growth hormone poly-adenylation signal (bGH polyA). The pGX0003 backbone includes the kanamycin resistance gene (KanR) and plasmid origin of replication (pUC ori) for production purpose. Those elements are not functional in eukaryotic cells.

A schematic diagram of pGX1439 and synthetic consensus MUC16 RMC and synthetic consensus MUC16 NRC is presented in FIG. 15, and the elements of the plasmid and corresponding base pairs are presented in Table 13.

TABLE 13

| Elements: | Base Pairs: |
| --- | --- |
| hCMV Promoter: | 5682-6506 |
| Synthetic consensus MUC16 RMC Coding Sequence: | 6524-8455 |
| SV40 PolyA | 8457-8662 |
| Kanamycin Resistance (KanR): | 298-1059 |
| pUC Ori: | 1227-1900 |
| sCMV Promoter | 4703-5193 |
| Synthetic consensus MUC16 NRC coding sequence: | 2557-4692 |
| bGH Poly A | 2290-2528 |

Example 5: In Vitro Antigen Expression

Expression of the antigen protein by pGX1435, pGX1436, pGX1437, pGX1438, and pGX1439 was confirmed by Western blotting. Human rhabdomyosarcoma (RD) cells (ATCC, CCL-136) maintained in DMEM medium with 10% FBS (ThermoFisher) were transfected with pGX1435, pGX1436, pGX1437, pGX1438, pGX1439, or pGX0001 (6 µg/10 cm$^2$ dish) using Turbofectin 8 (Origene). Forty-eight hours after transfection, the cells were lysed using RIPA cell lysis buffer (ThermoFisher) and cell lysate was collected. Following a BCA assay (ThermoFisher) to determine total protein concentration, 15 µg of cell lysate was electrophoresed on a 4-12% SDS-PAGE gel (ThermoFisher) and detection was performed using a an anti-MUC16 antibody (Abcam, clone EPSISR23-96, ab168360) then visualized with horseradish peroxidase (HRP)-conjugated anti-rabbit IgG (Santa Cruz Biotech #sc-2004) using an ECL western blot analysis system (GE Amersham). As a loading control, blots were re-probed for actin expression using an anti-β-actin monoclonal antibody (Santa Cruz Biotech, clone, C4).

Figure 16:
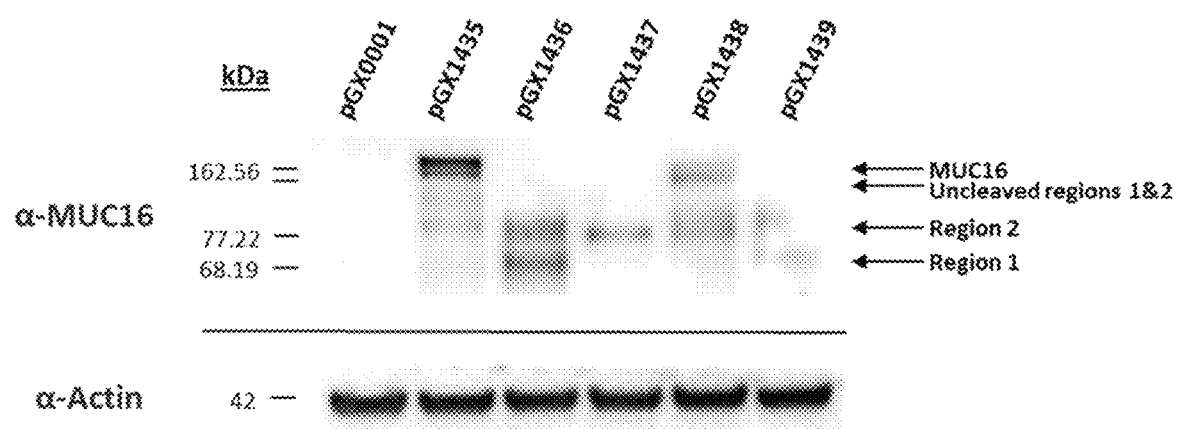
FIG. 16 illustrates expression of synthetic consensus MUC16 constructs by immunoblotting.

A protein band of the expected molecular weight for synthetic consensus MUC16 (~162.5 kD) was detected as well as protein bands for Region 1 (~68.2 kDa) and Region 2 (~77.2 kDa) (FIG. 16). No protein bands were detected in the pGX0001 lane indicating the protein bands were specific for synthetic consensus Muc16. Anti-β-actin bands were detected of similar intensities indicating equal amounts of protein were loaded in each lane. pGX1435 and pGX1438 were found to express its respective antigen protein and pGX1436, pGX1437 and pGX1439 were found to express their respective antigen protein regions.

Example 6: Immunogenicity of the Synthetic
Consensus Mesothelin Vaccine Constructs Animals and Immunizations Female, 8-week-old CB6F1 mice were purchased from Jackson Laboratories. All animals were housed in a temperature-controlled, light-cycled facility at BTS Research (San Diego, CA). Animal care was carried out according to the guidelines of the National Institutes of Health and the Animal Care and Use Proposal (ACUP) (BTS ACUP #15-091). Mice were divided into sixteen groups as detailed in Table 14.

TABLE 14

| Group | n | Construct | Construct Dose (μg) | Injection volume (μl) |
|---|---|---|---|---|
| 1 | 8 | pGX0001 | 30 | 30 |
| 2 | 8 | pGX1435 | 10 | 30 |
| 3 | 8 | pGX1435 | 30 | 30 |
| 4 | 8 | pGX1435 | 50 | 30 |
| 5 | 8 | pGX1436 | 10 | 30 |
| 6 | 8 | pGX1436 | 30 | 30 |
| 7 | 8 | pGX1436 | 50 | 30 |
| 8 | 8 | pGX1437 | 10 | 30 |
| 9 | 8 | pGX1437 | 30 | 30 |
| 10 | 8 | pGX1437 | 50 | 30 |
| 11 | 8 | pGX1438 | 10 | 30 |
| 12 | 8 | pGX1438 | 30 | 30 |
| 13 | 8 | pGX1438 | 50 | 30 |
| 14 | 8 | pGX1439 | 10 | 30 |
| 15 | 8 | pGX1439 | 30 | 30 |
| 16 | 8 | pGX1439 | 50 | 30 |

The mice in the immunized groups were vaccinated with the doses indicated of pGX0001 or pGX1435, pGX1436, pGX1437, pGX1438, pGX1439 according to SOP R20-003147 CELLECTRA® 3P Mouse Treatment. Briefly, plasmids were formulated in sterile water for injection (VetOne) such that the indicated dose was delivered by intramuscular injection into the tibialis anterior muscle in a 30 μL injection volume. Each intramuscular injection was immediately followed by electroporation (EP) using the CELLECTRA® 2000 Adaptive Constant Current Electroporation Device with a 3P array (Inovio Pharmaceuticals). The device was configured to deliver two 0.1 Amp pulses of 52 ms pulse width, spaced apart by a 1 second delay. Due to the large number of mice and groups, half of the mice in each group received 3 immunizations, 3 weeks apart. These mice were sacrificed one week after the last immunization and spleens harvested for cellular immune readouts. The other half of the mice in each group received 3 immunizations, 3 weeks apart. Mice were sacrificed one week after the last immunization and spleens harvested for cellular immune readouts. No other tissue was collected.

Splenic Lymphocyte Isolation

Splenocytes were aseptically isolated and placed in 5 mL of R10 media (Rosewell Park Memorial Institute medium 1640 supplemented with 10% fetal bovine serum and 1% antibiotic-antimycotic). Splenocytes were isolated by mechanical disruption of the spleen using a Stomacher machine (Seward Laboratory Systems Inc.), and the resulting product was filtered using a 40-μm cell strainer (BD Falcon). The resulting product was centrifuged and the pellet was treated for 5 min with ACK lysis buffer (Lonza) for lysis of RBCs. The splenocytes were then centrifuged, washed in PBS, and then resuspended in R10 media and immediately used for further analysis.

IFNγ ELISpot

Figure 17:
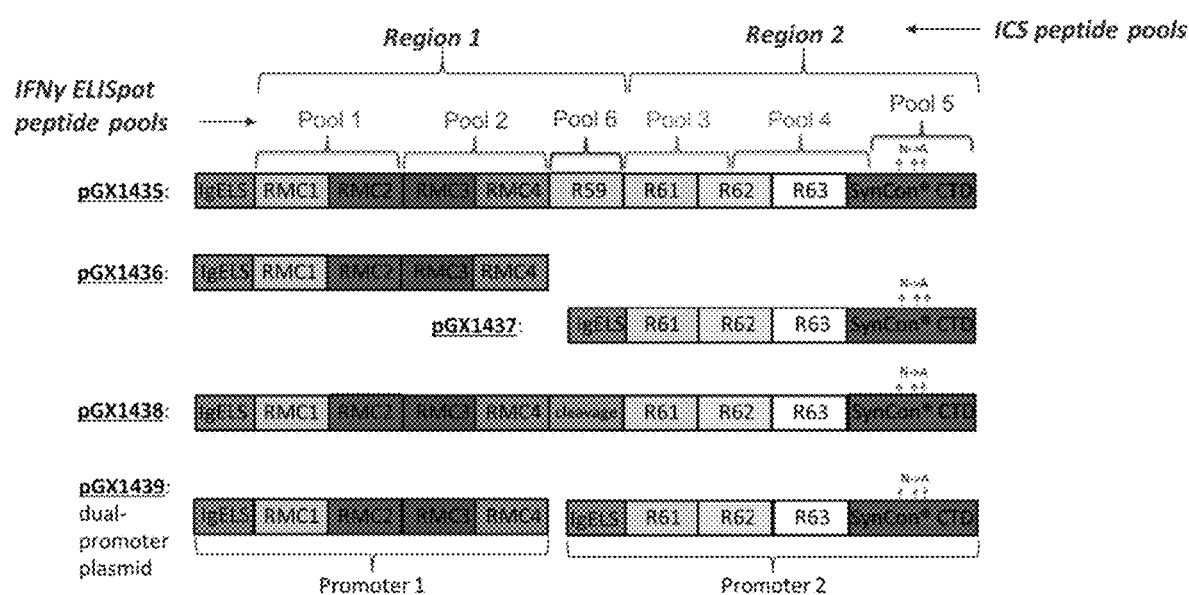
FIG. 17 is a diagrammatic representation of the peptide pools contained in the peptides corresponding to the synthetic consensus MUC16 antigen proteins used in embodiments of the disclosure.

Mouse IFNγ ELISpot assay was performed using a kit from MabTech (MabTech, #3321-4APW-10) to evaluate antigen-specific cellular responses. Ninety-six well plates pre-coated with anti-mouse IFNγ antibody (mAb AN18) were washed in PBS and blocked for 2 hours at room temperature with R10 media, and then plated (in triplicates) at an input cell number of $2 \times 10^5$ cells per well. A set of peptides was synthesized (GenScript), each containing 15 amino acid residues overlapping by 11 amino acids representing the entire synthetic consensus MUC16 protein sequence for each construct. These sets of peptides were resuspended in DMSO (Sigma) and pooled at a concentration of ~2 μg/ml peptide into six peptide pools. The peptide pools contained the peptides corresponding to the synthetic consensus MUC16 antigen protein as indicated in the schematic provided in FIG. 17. Concanavalin A (Sigma) at 5 μg/ml was used as a positive control and complete culture medium was used as a negative control. Plates were incubated for 18 hours at 37° C., in a 5% CO2 atmosphere incubator. Then, a biotinylated anti-mouse IFNγ detection antibody (MabTech, mAb R4-6A2) was added, and plates were incubated for 2 hours at room temperature. The plates were washed, and Streptavidin-ALP antibody (MabTech) was added and plates incubated for 1 hour at room temperature. Spot detection was completed using the BCIP/NBT substrate according to the kit manufacturer's instructions (MabTech). The spots on the plates were counted using an automated ELISPOT reader (Cellular Technology). The average number of Spot Forming Units (SFU) was adjusted to $1 \times 10^6$ splenocytes for data display.

Antigen specific responses by IFNγ ELISpot are reported as the number of IFNγ spot forming unit (SFU) per $1 \times 10^6$ splenocytes greater than the SFU in the media only control.

Immunogenicity of the synthetic consensus MUC16 construct was evaluated at three dose amounts (10 μg, 30 μg, and 50 μg) by IFNγ ELISpot and flow cytometry (n=8/group). Mice were immunized with the empty plasmid backbone (pGX0001) as a negative control (n=4/group). Vaccination with synthetic consensus MUC16 full length constructs (pGX1435, pGX1438, and pGX1439) induced exceptionally robust cellular immune responses compared to negative control vaccinated mice.

Figure 18A:
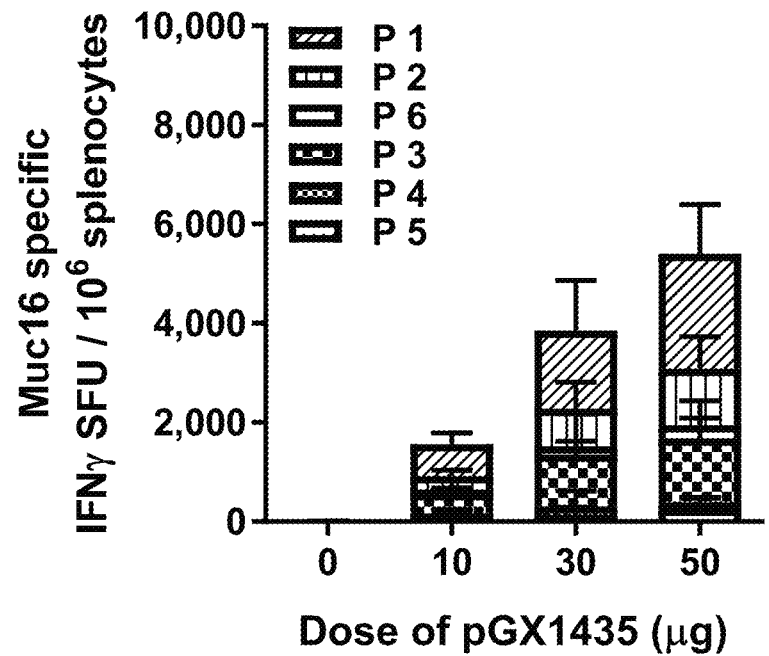
FIGS. 18A-18D illustrate IFNγ responses by ELISpot from immunization of female CB6F1 3 times, 3 weeks apart with the indicated dose amounts of synthetic consensus MUC16 (pGX1435 (FIG. 18A), pGX1438 (FIG. 18B), and pGX1439 (FIG. 18C), n=8/group), or pGX0001 (empty vector, n=8). Detectable responses to the unique R59 (peptide pool 6) epitope induced by pGX1435 are also indicated (FIG. 18D).

The magnitude of IFNγ production to synthetic consensus MUC16 induced by pGX1435, as determined by ELISpot, was dose-dependent (FIG. 18A). Specifically, synthetic consensus MUC16 pGX1435 IFNγ SFU were 1564±661, 3858±2767, and 5407±1959 at the 10 μg, 30 μg, and 50 μg dose amounts, respectively. Synthetic consensus MUC16 IFNγ responses induced by pGX1435 were significantly greater than naïve at the 10 μg (p=0.002), 30 μg (p=0.028), and 50 μg (p=0.001) doses of pGX1435. Detectable responses to the unique R59 (peptide pool 6) epitope induced by pGX1435 are also indicated in FIG. 18D.

Figure 18B:
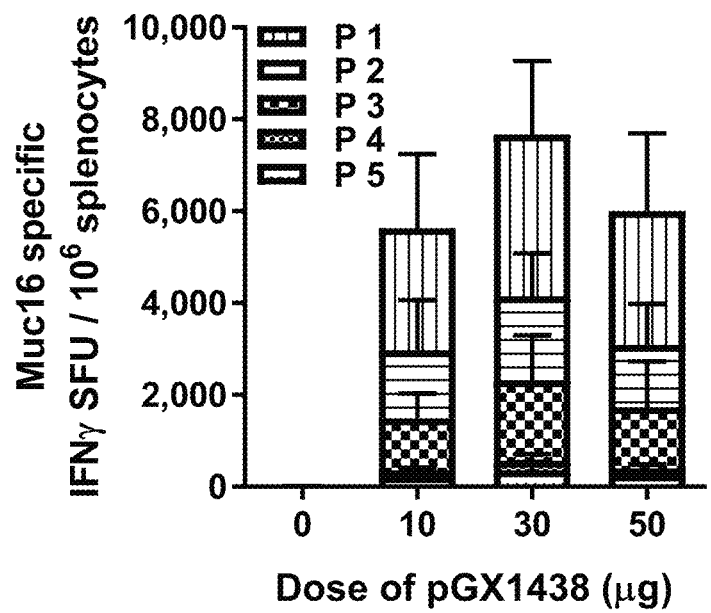

The magnitude of synthetic consensus MUC16 specific IFNγ production induced by the pGX1438 construct, as determined by ELISpot, was dose-independent with the lower doses inducing a more robust response (FIG. 18B). Specifically, synthetic consensus MUC16 pGX1438 IFNγ SFU were 5628±3144, 7668±3371, and 6005±3472 at the 10 μg, 30 μg, and 50 μg dose amounts, respectively. Synthetic consensus MUC16 IFNγ responses induced by pGX1438 were significantly greater than naïve at the 10 μg (p=0.008), 30 μg (p=0.002), and 50 μg (p=0.009) dose amounts of pGX1435.

Figure 18C:
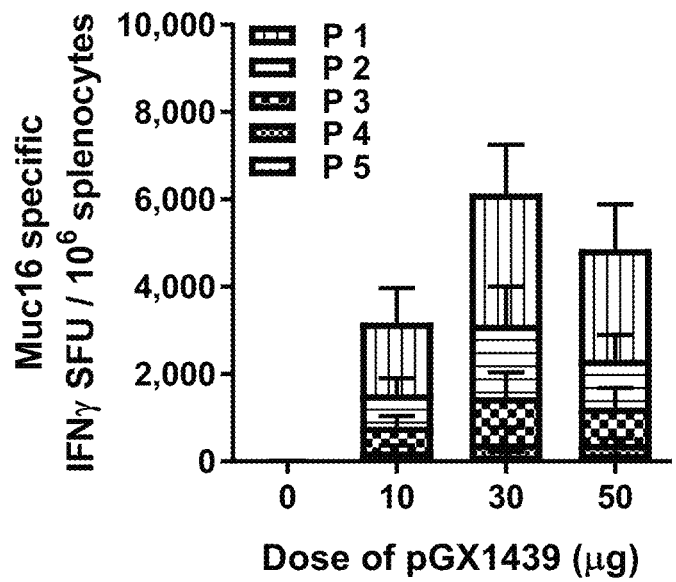
Figure 18D:
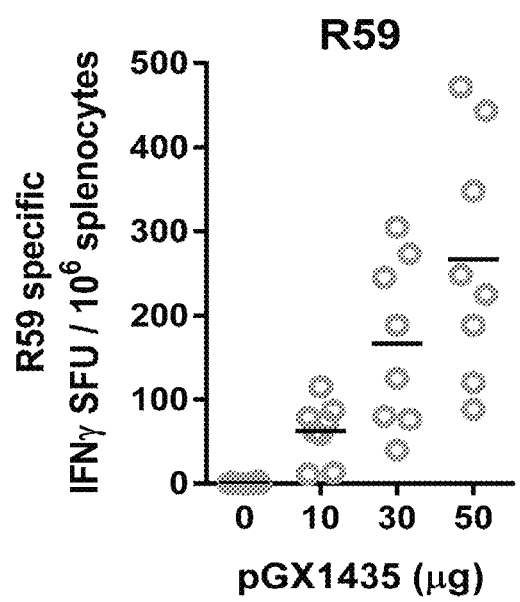

The magnitude of synthetic consensus MUC16 specific IFNγ production induced by the pGX1439 construct, as determined by ELISpot, was also dose-independent with the lower dose amounts inducing a more robust response (FIG. 18C). Specifically, the pGX1439 synthetic consensus MUC16 IFNγ SFU were 3180±1377, 6138±2696, and 4862±2069 at the 10 30 and 50 µg dose amounts, respectively. Synthetic consensus MUC16 pGX1439 IFNγ responses were significantly greater than naïve at the 10 µg (p=0.002), 30 µg (p=0.002), and 50 µg (p=0.002) dose amounts of pGX1435.

IFNγ responses for the full length constructs are summarized in Table 15.

TABLE 15

| Product Code | Group | Dose amount | Mean SFU ± Std. Dev. | p-value |
|---|---|---|---|---|
| Synthetic Consensus Muc16 Fusion (pGX1435) IFNγ ELISpot | | | | |
| pGX0001 | Naive | 30 µg | 7 ± 8 | n/a |
| pGX1435 | Immunized | 10 µg | 1564 ± 661 | 0.002 |
| | | 30 µg | 3858 ± 2767 | 0.028 |
| | | 50 µg | 5407 ± 1959 | 0.001 |
| Synthetic Consensus Muc16 Furin Cleavage (pGX1438) IFNγ ELISpot | | | | |
| pGX0001 | Naive | 30 µg | 7 ± 8 | n/a |
| pGX1438 | Immunized | 10 µg | 5628 ± 3144 | 0.008 |
| | | 30 µg | 7668 ± 3371 | 0.002 |
| | | 50 µg | 6005 ± 3472 | 0.009 |
| Synthetic Consensus Muc16 Dual Promoter (pGX1439) IFNγ ELISpot | | | | |
| pGX0001 | Naive | 30 µg | 7 ± 8 | n/a |
| pGX1439 | Immunized | 10 µg | 3180 ± 1377 | 0.002 |
| | | 30 µg | 6138 ± 2696 | 0.002 |
| | | 50 µg | 4862 ± 2069 | 0.002 |

Statistical significance assumed at p ≤ 0.05. p-values reported are relative to naïve (pGX0001 immunized mice).

Vaccination with synthetic consensus MUC16 partial length constructs (pGX1436 and pGX1437) also induced exceptionally robust cellular immune responses compared to negative control vaccinated mice.

Figure 19A:
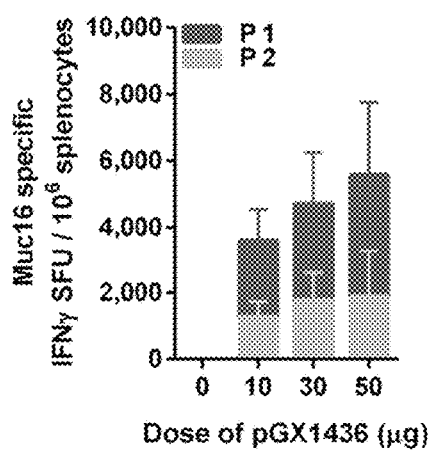
FIGS. 19A-19D illustrate results from immunization of female CB6F1 3 times, 3 weeks apart with the indicated dose amounts of synthetic consensus MUC16 (pGX1436 (FIG. 19A) and pGX1437 (FIG. 19C), n=8/group), or pGX0001 (empty vector, n=8). Synthetic consensus MUC16 specific IFNγ responses by ELISpot at indicated dose amounts of pGX1436 and pGX1437 as well as comparison of immune responses to full length constructs (FIG. 19B and FIG. 19D).
Figure 19B:
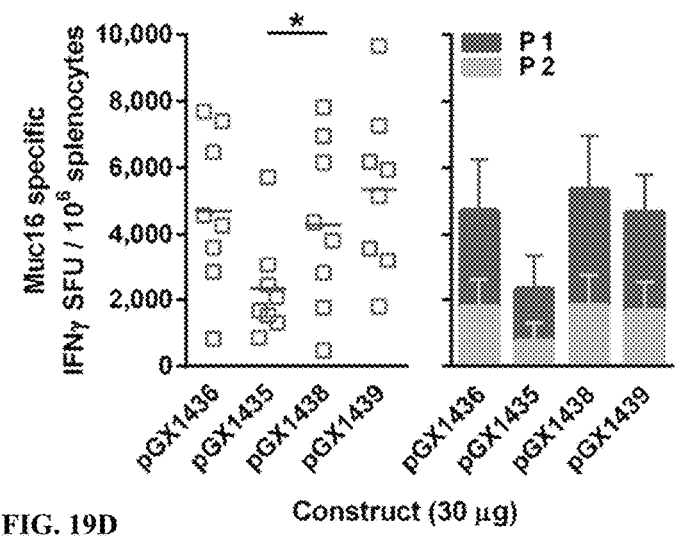

The magnitude of synthetic consensus MUC16 specific IFNγ production against region 1 induced by the pGX1436 construct, as determined by ELISpot, was dose-dependent (FIG. 19A). Specifically, synthetic consensus MUC16 specific IFNγ SFU induced by pGX1436 were 3609±1377, 4711±2365, and 5565±3496 at the 10 µg, 30 µg, and 50 µg dose amounts, respectively. Synthetic consensus MUC16 IFNγ responses elicited by pGX1436 were significantly greater than naïve at the 10 µg (p=0.001), 30 µg (p=0.004), and 50 µg (p=0.014) dose amounts of pGX1436. When comparing IFNγ responses to Region 1 induced by all MUC16 constructs, pGX1435-induced responses are significantly lower than pGX1438 (FIG. 19B).

Figure 19C:
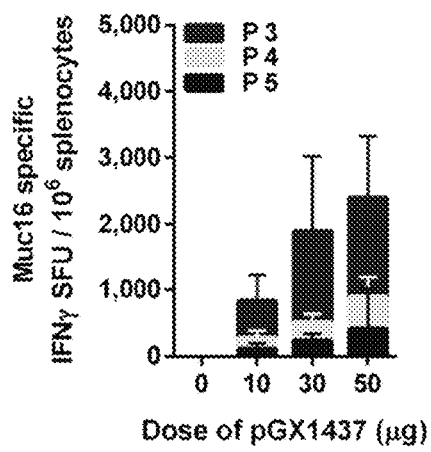
Figure 19D:
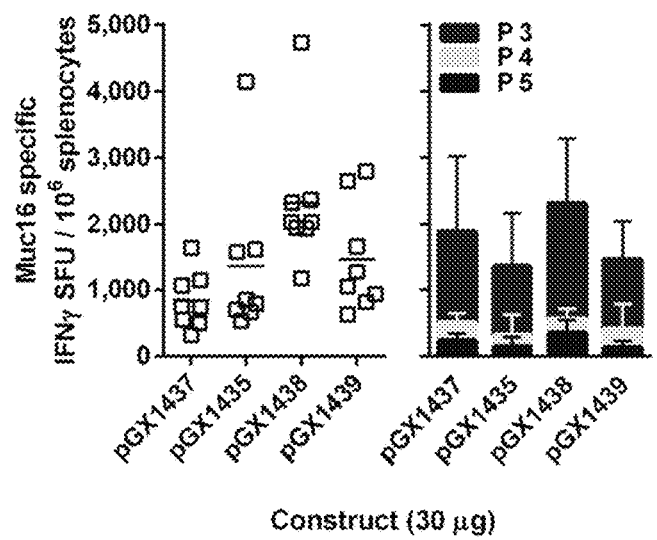

The magnitude of synthetic consensus MUC16-specific IFNγ production against region 2 induced by the pGX1437 construct, as determined by ELISpot, was also dose-dependent (FIG. 19C). Specifically, synthetic consensus MUC16 pGX1437 IFNγ SFU were 835±428, 1893±1291, and 2399±1245 at the 10 µg, 30 µg, and 50 µg dose amounts, respectively. Synthetic consensus MUC16 pGX1437 IFNγ responses were significantly greater than naïve at the 10 µg (p=0.005), 30 µg (p=0.022), and 50 µg (p=0.005) dose amounts of pGX1437. There was a trend towards more robust IFNγ production against Region 2 with pGX1438 (FIG. 19D).

IFNγ responses for the partial length constructs are summarized in Table 16.

TABLE 16

| Product Code | Group | Dose amount | Mean SFU ± Std. Dev. | p-value |
|---|---|---|---|---|
| Synthetic Consensus Muc16 "Region 1" (pGX1436) IFNγ ELISpot | | | | |
| pGX0001 | Naive | 30 µg | 3 ± 5 | n/a |
| pGX1436 | Immunized | 10 µg | 3609 ± 1377 | 0.001 |
| | | 30 µg | 4711 ± 2365 | 0.004 |
| | | 50 µg | 5565 ± 3496 | 0.014 |
| Synthetic Consensus Muc16 "Region 2" (pGX1437) IFNγ ELISpot | | | | |
| pGX0001 | Naive | 30 µg | 3 ± 5 | n/a |
| pGX1437 | Immunized | 10 µg | 835 ± 428 | 0.005 |
| | | 30 µg | 1893 ± 1291 | 0.022 |
| | | 50 µg | 2399 ± 1245 | 0.005 |

Statistical significance assumed at p ≤ 0.05. p-values reported are relative to naïve (pGX0001 immunized mice).

Flow Cytometry

Cellular immune responses induced by synthetic consensus MUC16 were further characterized by flow cytometry. $2 \times 10^6$ splenocytes from vaccinated and naïve mice were immediately stimulated following isolation with the synthetic consensus MUC16 peptides for 6 hours in the presence of Brefeldin A (BD Biosciences), Monensin (BD Biosciences), and FITC anti-mouse CD107a antibody (BD Biosciences). After stimulation with peptides, splenocytes were spun down and resuspended in 20 µL per well of mouse BD Fc Block (BD Biosciences) solution. The Fc Block is used at an initial dilution of 1:40 in PBS and incubated at 4° C. for 5 minutes.

After incubation, the remaining extracellular antibodies (in PBS) are added at 30 µL per well and allowed to incubate at 4° C. for 30 minutes. Upon addition of the extracellular stain, the final volume in each well is 50 µL, consisting of Fc Block at a final dilution of 1:100 and the extracellular antibodies at their appropriate working dilutions. Cells were then stained with viability dye (Vivid, Thermo-Fisher) and the following extracellular antibodies: PerCP-Cy5.5 anti-mouse CD4 (BD Biosciences, clone RM4-5), and APC anti-mouse CD8a (BD Biosciences, clone 63-6,7). Intracellular cytokines were subsequently stained with the following antibodies: BV605 anti-mouse IFNγ, APC-R700 anti-mouse IL-2, and PE anti-mouse TNF-α (BD Biosciences). Cells were fixed and permeabilized (BD Biosciences, #554714) for 20 minutes at 4° C. Intracellular staining was subsequently completed with the following antibodies: APC-Cy7 anti-mouse CD3e (BD Biosciences, clone 145-2C11), BV605 anti-mouse IFNγ (BD Biosciences, clone XMG1.2), APC-R700 anti-mouse IL-2 (BD Biosciences, clone JEs6-5H4), and PE anti-mouse TNF-α (BD Biosciences, clone MP6-XT22).

Figure 20:
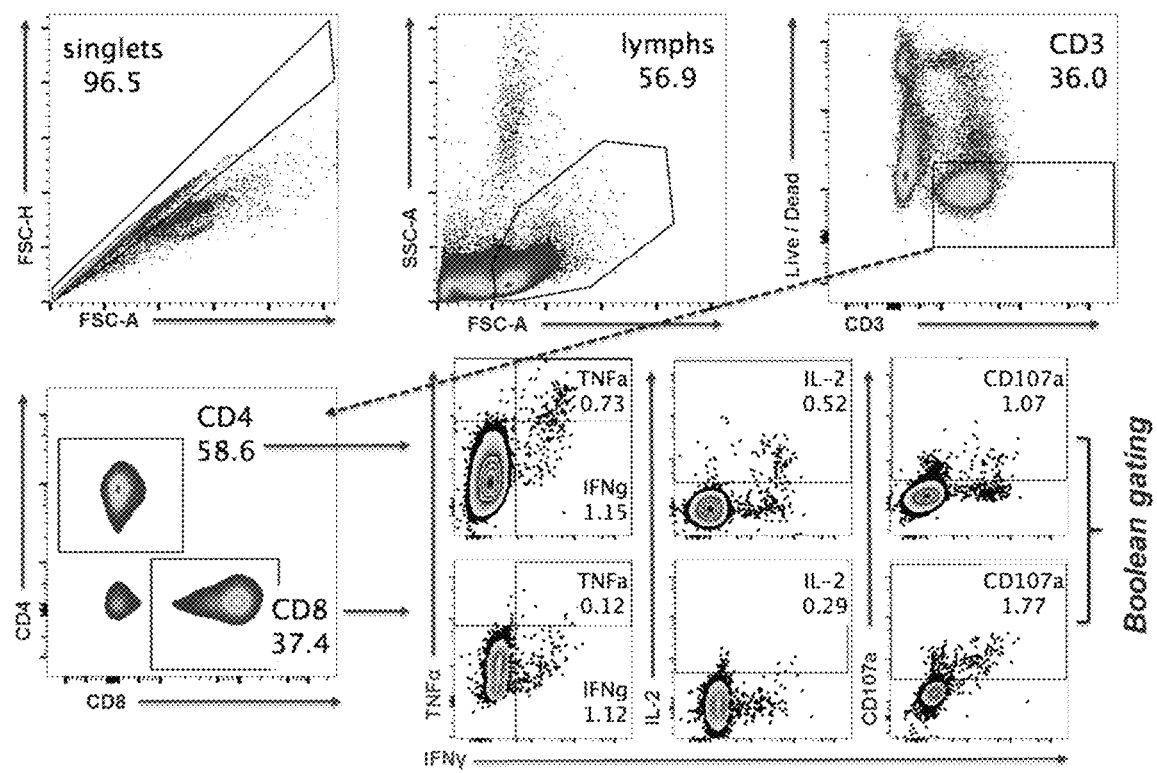
FIG. 20 illustrates the flow cytometry gating strategy used in embodiments of the disclosure.

ICS data was collected on 10-color FACS CANTO (BD Biosciences) and analysis completed using FlowJo software. The flow cytometry gating strategy is shown in FIG. 20. For a cell to be called antigen specific by flow cytometry, the frequency of the reported parameter must exceed that of the media-only control. For a cell to be identified as producing antigen specific CD107a, the cell must also be identified as positive for antigen specific production of IFNγ, and/or IL-2 and/or TNFa as identified by Boolean gating.

Figure 21A:
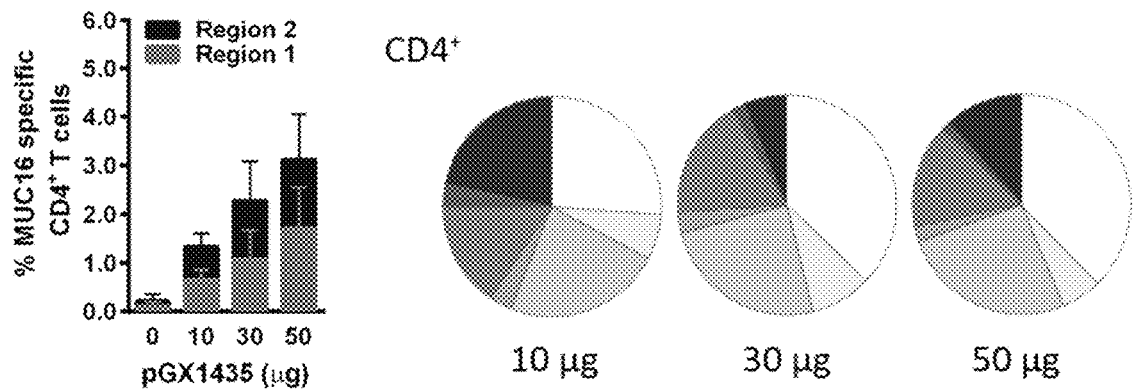
FIGS. 21A-21C illustrate the relative frequency of CD4+ T cells induced by synthetic consensus MUC16 full length constructs pGX1435 (FIG. 21A), pGX1438 (FIG. 21B), and pGX1439 (FIG. 21C).
Figure 21B:
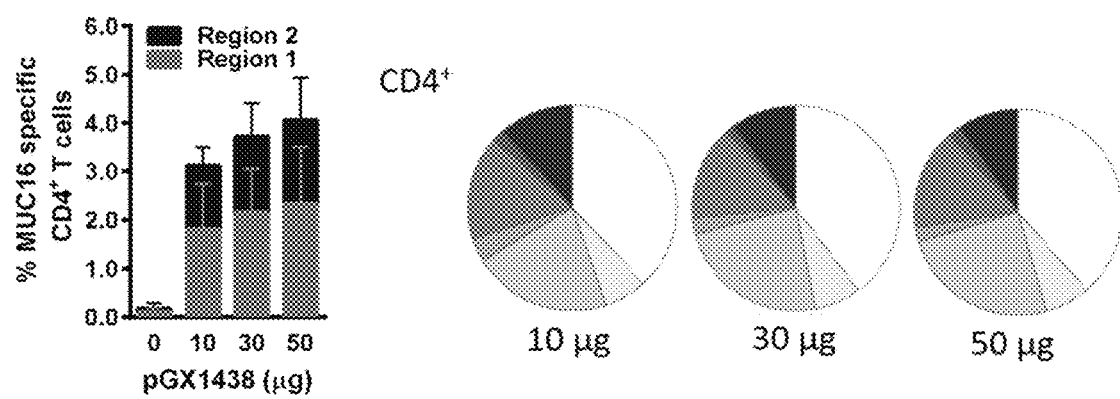
Figure 21C:
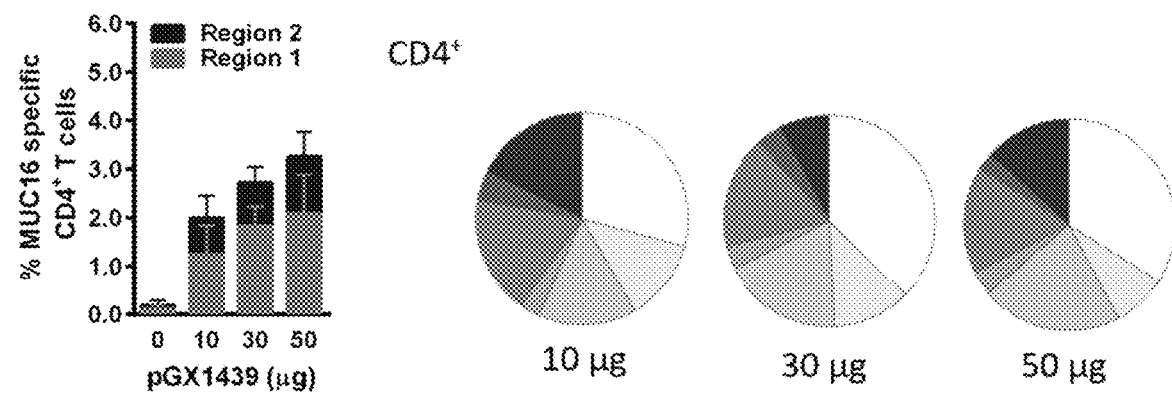

Synthetic consensus MUC16 full length constructs elicited strong responses in the CD4$^+$ T cell compartment, with pGX1438 being the most robust (FIGS. 21A-21C). Synthetic consensus MUC16 induced frequencies of antigen specific CD4$^+$ T cell responses that were significantly more robust than naïve (0.29%±0.23%) in the 10 µg, 30 µg, and 50 µg dose level groups for pGX1435, pGX1438, and pGX1439 (FIGS. 21A-21C).

The magnitude of synthetic consensus MUC16 pGX1435 construct specific CD4$^+$ T cells was dose-dependent (FIG. 21A). Specifically, synthetic consensus MUC16 pGX1435 CD4$^+$ T cells were 1.34%±0.45%, 2.27%±1.38%, and 3.12%±1.45% at the 10 µg, 30 µg, and 50 µg dose amounts, respectively. Synthetic consensus MUC16 pGX1435 CD4$^+$ T cells were significantly greater than naïve at the 10 µg (p<0.001), 30 µg (p=0.020), and 50 µg (p=0.004) dose amounts of pGX1435. Synthetic consensus MUC16 pGX1435 specific CD4$^+$ T cell responses consisted mainly of IFNγ$^+$IL-2$^+$TNFα$^+$, IFNγ$^+$IL-2$^-$TNFα$^+$ or IFNγ$^+$IL-2$^-$TNFα$^-$ producing CD4$^+$ T cells.

The magnitude of synthetic consensus MUC16 pGX1438 construct specific CD4+ T cells was also dose-dependent (FIG. 21B). Specifically, synthetic consensus MUC16 pGX1438 CD4$^+$ T cells were 3.12%±1.19%, 3.73%±1.48%, and 4.06%±1.87% at the 10 µg, 30 µg, and 50 µg dose amounts, respectively. Synthetic consensus MUC16 pGX1438 CD4$^+$ T cells were significantly greater than naïve at the 10 µg (p=0.001), 30 µg (p=0.001), and 50 µg (p=0.003) dose amounts of pGX1438. Synthetic consensus MUC16 pGX1438 specific CD4$^+$ T cell responses consisted mainly of IFNγ+IL-2+TNFα+, IFNγ+IL-2-TNFα+ or IFNγ$^+$IL$^-$2-TNFα$^-$ producing CD4$^+$ T cells.

The magnitude of synthetic consensus MUC16 pGX1439 construct specific CD4$^+$ T cells was dose-dependent (FIG. 21C). Specifically, synthetic consensus MUC16 pGX1439 CD4$^+$ T cells were 1.99%±0.99%, 2.71%±0.51%, and 3.25%±1.29% at the 10 and 50 µg dose amounts, respectively. Synthetic consensus MUC16 pGX1439 CD4+ T cells were significantly greater than naïve at the 10 µg (p=0.007), 30 µg (p<0.001), and 50 µg (p=0.001) dose amounts of pGX1439. Synthetic consensus MUC16 pGX1439 specific CD4$^+$ T cell responses consisted mainly of IFNγ+IL-2+ TNFα+, IFNγ+IL-2-TNFα+ or IFNγ$^+$IL-2$^-$TNFα$^-$ producing CD4+ T cells. The frequency of antigen specific CD4$^+$ T cells is further detailed in Table 17.

All dose amounts of synthetic consensus MUC16 full length constructs induced a frequency of CD4$^+$CD107a$^+$ T cells that was greater than naïve (0.08%±0.04%) but only the pGX1438 construct at all doses was significantly more robust.

Specifically, the frequency of pGX1435 antigen specific CD4$^+$CD107a$^+$ T cells was 0.27%±0.14%, 0.32%±0.37%, and 0.64%±0.34% in the 10 µg (p=0.011), 30 µg (p=0.297), and 50 µg (p=0.008) dose amounts groups, respectively (FIG. 21A). The cytokine profile of pGX1435 specific CD4$^+$CD107a$^+$ T cells was similar across dose amount groups and was comprised mainly of IFNγ$^+$IL-2$^+$TNFα$^+$ and IFNγ$^+$IL-2$^-$TNFα$^+$ cells (FIG. 22A).

The frequency of pGX1438 antigen specific CD4+ CD107a+ T cells was 0.40%±0.18%, 0.54%±0.36%, and 0.53%±0.25% in the 10 µg (p=0.004), 30 µg (p=0.029), and 50 µg (p=0.004) dose amount groups, respectively (FIG. 21B). The cytokine profile of pGX1438 specific CD4$^+$ CD107a$^+$ T cells was similar across dose amount groups and was comprised mainly of IFNγ$^+$IL-2$^+$TNFα$^+$ and IFNγ$^+$IL-2$^-$TNFα$^+$ cells (FIG. 22B).

The frequency of pGX1439 antigen specific CD4+ CD107a+ T cells was 0.26%±0.18%, 0.36%±0.18%, and 0.50%±0.25% in the 10 µg (p=0.069), 30 µg (p=0.008), and 50 µg (p=0.006) dose groups, respectively (FIG. 22C). The cytokine profile of pGX1439 specific CD4$^+$CD107a$^+$ T cells was similar across dose groups and was comprised mainly of IFNγ$^+$IL-2$^+$TNFα$^+$ and IFNγ$^+$IL-2$^-$TNFα$^+$ cells (FIG. 22C). The frequency of antigen specific CD4$^+$ T cells with cytolytic potential is further detailed in Table 17.

TABLE 17

| Product Code | Group | Dose amount | % CD4$^+$ ± Std. Dev. | % CD4$^+$ p-value | % CD4$^+$CD107a$^+$ ± Std. Dev. | % CD4$^+$CD107a$^+$ p-value |
|---|---|---|---|---|---|---|
| Synthetic Consensus Muc16 Fusion (pGX1435) CD4$^+$ and CD4$^+$CD107a$^+$T cells ||||||| 
| pGX0001 | Naive | 30 µg | 0.29 ± 0.23 | n/a | 0.08 ± 0.04 | n/a |
| pGX1435 | Immunized | 10 µg | 1.34 ± 0.45 | <0.001 | 0.27 ± 0.14 | 0.011 |
|  |  | 30 µg | 2.27 ± 1.38 | 0.020 | 0.32 ± 0.37 | 0.297 |
|  |  | 50 µg | 3.12 ± 1.45 | 0.004 | 0.64 ± 0.34 | 0.008 |
| Synthetic Consensus Muc16 Synthetic Consensus Muc16 Furin Cleavage (pGX1438) CD4$^+$ and CD4$^+$CD107a$^+$ T cells ||||||| 
| pGX0001 | Naive | 30 µg | 0.29 ± 0.23 | n/a | 0.08 ± 0.04 | n/a |
| pGX1438 | Immunized | 10 µg | 3.12 ± 1.19 | 0.001 | 0.40 ± 0.18 | 0.004 |
|  |  | 30 µg | 3.73 ± 1.48 | 0.001 | 0.54 ± 0.36 | 0.029 |
|  |  | 50 µg | 4.06 ± 1.87 | 0.003 | 0.53 ± 0.25 | 0.004 |
| Synthetic Consensus Muc16 Dual Promoter (pGX1439) CD4$^+$ and CD4$^+$CD107a$^+$ T cells ||||||| 
| pGX0001 | Naive | 30 µg | 0.29 ± 0.23 | n/a | 0.08 ± 0.04 | n/a |
| pGX1439 | Immunized | 10 µg | 1.99 ± 0.99 | 0.007 | 0.26 ± 0.18 | 0.069 |
|  |  | 30 µg | 2.71 ± 0.51 | <0.001 | 0.36 ± 0.18 | 0.008 |
|  |  | 50 µg | 3.25 ± 1.29 | 0.001 | 0.50 ± 0.25 | 0.006 |

Statistical significance assumed at p ≤ 0.05.

p-values reported are relative to naïve (pGX0001 immunized mice).

Figure 23A:
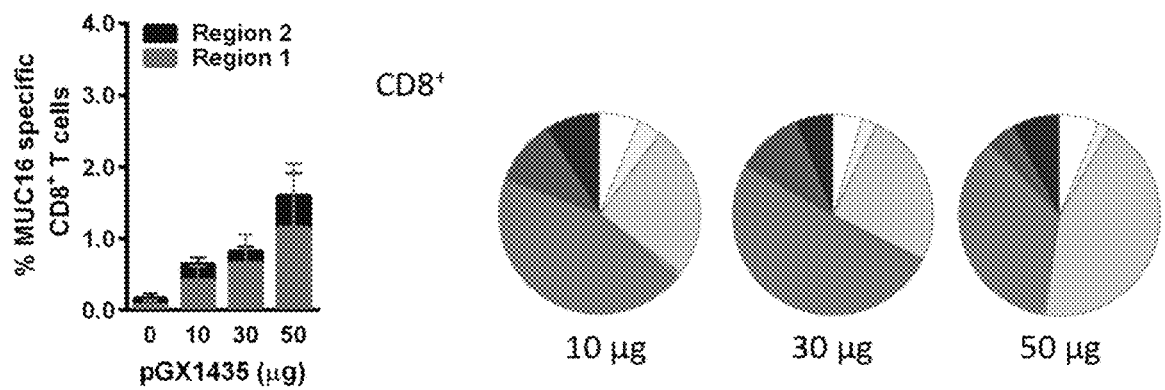
FIGS. 23A-23C illustrate cellular immune responses induced by pGX1435 (FIG. 23A), pGX1438 (FIG. 23B), and pGX1439 (FIG. 23C) in the CD8+ T cell compartment.
Figure 23B:
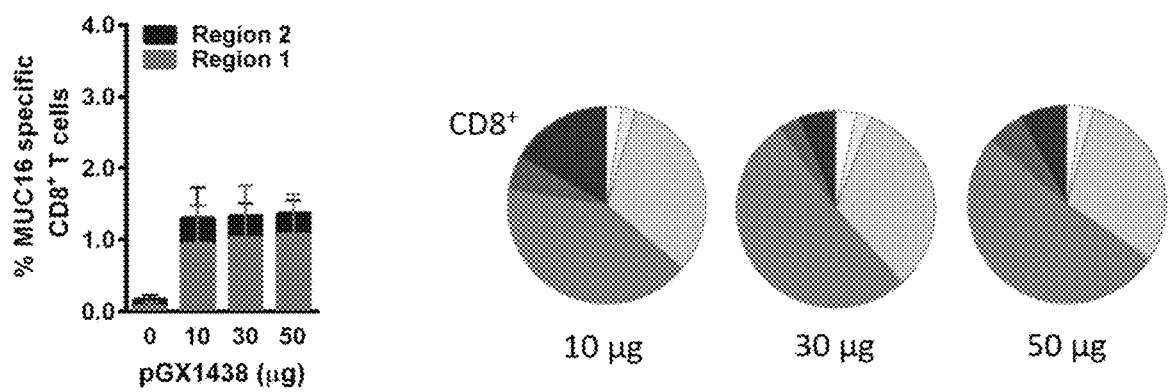
Figure 23C:
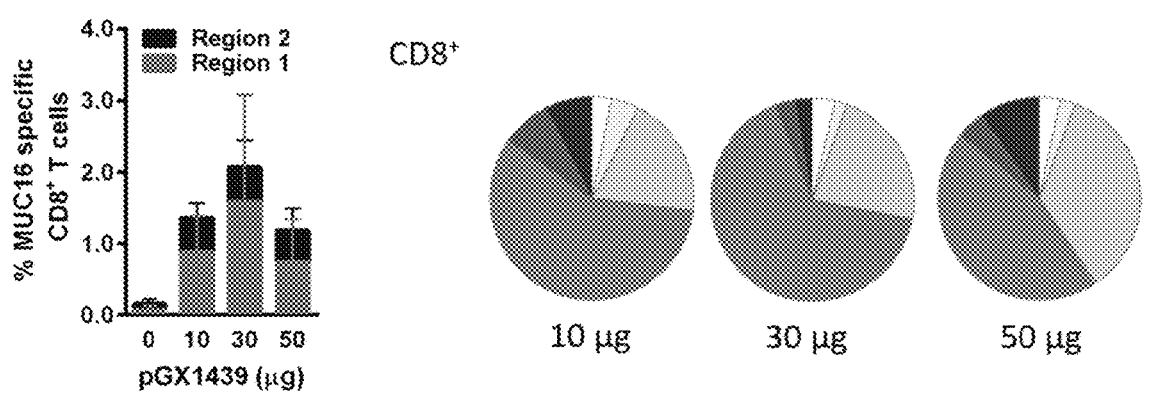

The frequency of antigen specific CD8+ T cells induced by synthetic consensus MUC16 full length constructs increased over control (0.13%±0.15%) in all dose groups for all constructs (FIGS. 23A-23C). Specifically, the frequency of antigen specific CD8+ T responses in the groups immunized with 10 μg (0.65%±0.28%, p=0.007), 30 μg (0.82%±0.46%, p=0.022), and 50 μg (1.60±1.08%, p=0.034) of pGX1435 was significantly more robust compared to naïve. Synthetic consensus MUC16 pGX1435 specific CD8+ T cell responses were dose-dependent and consisted mainly of IFNγ+IL-2−TNFα− and IFNγ+IL-2−TNFα+ producing CD8+ T cells (FIG. 23A).

The frequency of antigen specific CD8+ T responses in the groups immunized with 10 μg (1.30%±0.79%, p=0.024), 30 μg (1.33%±0.87%, p=0.034), and 50 μg (1.36%±0.71%, p=0.010) of pGX1438 was also significantly more robust compared to naïve. Synthetic consensus MUC16 pGX1438 specific CD8+ T cell responses were dose-independent, with very little difference between the doses, and consisted mainly of IFNγ+IL-2−TNFα− and IFNγ+IL-2−TNFα+ producing CD8+ T cells (FIG. 23B).

The frequency of antigen specific CD8+ T responses in the groups immunized with 10 μg (1.36%±0.62%, p=0.004), 30 μg (2.07%±1.77%, p=0.089), and 50 μg (1.19%±0.69%, p=0.020) of pGX1439 was more robust compared to naïve. Synthetic consensus MUC16 pGX1439 specific CD8+ T cell responses were dose-independent and consisted mainly of IFNγ+IL-2−TNFα− and IFNγ+IL-2−TNFα+ producing CD8+ T cells (FIG. 23C). The frequency of antigen specific CD8+ T cells is further detailed in Table 18.

Figure 24A:
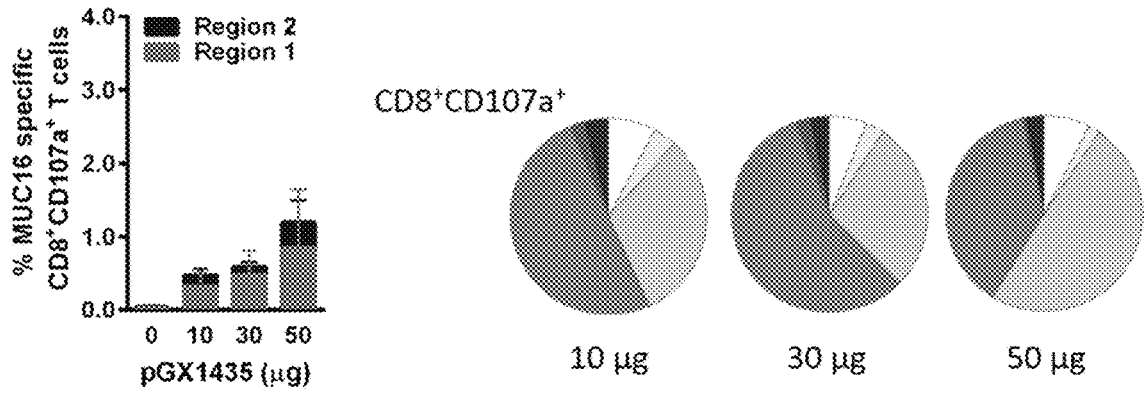
FIGS. 24A-24C illustrate the cytolytic immune responses and cytokine profile induced by pGX1435 (FIG. 24A), pGX1438 (FIG. 24B), and pGX1439 (FIG. 24C) in the CD8+ T cell compartment.
Figure 24B:
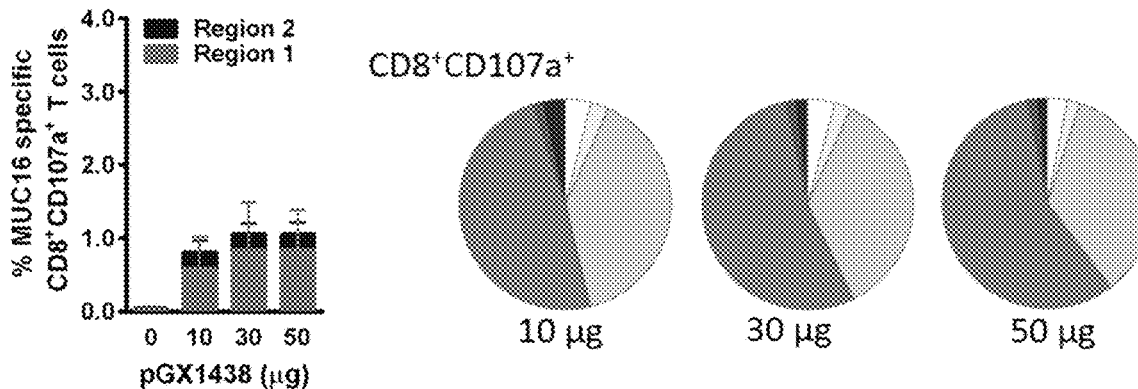
Figure 24C:
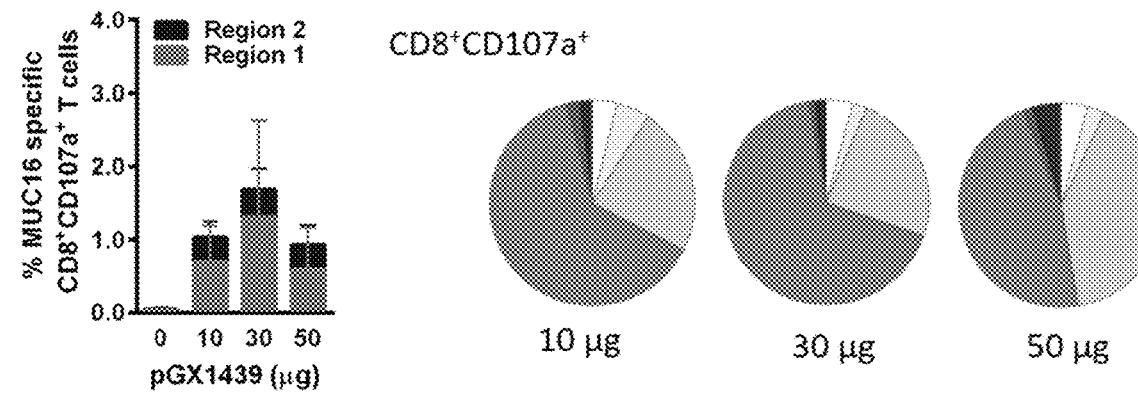

Similar to the pattern of antigen specific CD8+ T cells, synthetic consensus MUC16 full length constructs induced a significant change in the frequency of CD8+CD107a+ T cells among all groups compared to naïve (0.05%±0.04%), with the exception of pGX1439 at the 30 μg dose amount (FIGS. 24A-24C). Specifically, the frequency of antigen specific CD8+CD107a+ T cells was 0.47±0.23%, 0.59±0.34%, and 1.19±0.90% in the 10 μg (p=0.005), 30 μg (p=0.013), and 50 μg (p=0.043) dose amount groups of pGX1435, respectively (FIG. 24A). The cytokine profile of pGX1435 specific CD8+CD107a+ T cells was similar across dose amount groups and the majority was comprised of IFNγ+IL-2−TNFα− and IFNγ+IL-2−TNFα+ cells (FIG. 23A).

The frequency of antigen specific CD8+CD107a+ T cells was 0.80%±0.48%, 1.05%±0.77%, and 1.05%±0.65% in the 10 μg (p=0.016), 30 μg (p=0.039), and 50 μg (p=0.016) dose amount groups of pGX1438, respectively (FIG. 23B). The cytokine profile of pGX1438 specific CD8+CD107a+ T cells was similar across dose amount groups and the majority was comprised of IFNγ+IL-2−TNFα− and IFNγ+IL-2−TNFα+ cells (FIG. 24B).

The frequency of antigen specific CD8+CD107a+ T cells was 1.04%±0.65%, 1.68%±1.54%, and 0.93%±0.68% in the 10 μg (p=0.018), 30 μg (p=0.094), and 50 μg (p=0.038) dose amount groups of pGX1439, respectively (FIG. 23C). The cytokine profile of pGX1439 specific CD8+CD107a+ T cells was similar across dose amount groups and the majority was comprised of IFNγ+IL-2−TNFα− and IFNγ+IL-2−TNFα+ cells (FIG. 24C). The frequency of antigen specific CD8+ T cells with cytolytic potential is further detailed in Table 18.

TABLE 18

| Product Code | Group | Dose amount | % CD8+ ± Std. Dev. | % CD8+ p-value | % CD8+CD107a+ ± Std. Dev. | % CD8+CD107a+ p-value |
|---|---|---|---|---|---|---|
| Synthetic consensus Muc16 Fusion (pGX1435) CD8+ and CD8+CD107a+ T cells | | | | | | |
| pGX0001 | Naive | 30 μg | 0.13 ± 0.15 | n/a | 0.05 ± 0.04 | n/a |
| pGX1435 | Immunized | 10 μg | 0.65 ± 0.28 | 0.007 | 0.47 ± 0.23 | 0.005 |
| | | 30 μg | 0.82 ± 0.46 | 0.022 | 0.59 ± 0.34 | 0.013 |
| | | 50 μg | 1.60 ± 1.08 | 0.034 | 1.19 ± 0.90 | 0.043 |
| Synthetic consensus Muc16 Furin Cleavage (pGX1438) CD8+ and CD8+CD107a+ T cells | | | | | | |
| pGX0001 | Naive | 30 μg | 0.13 ± 0.15 | n/a | 0.05 ± 0.04 | n/a |
| pGX1438 | Immunized | 10 μg | 1.30 ± 0.79 | 0.024 | 0.80 ± 0.48 | 0.016 |
| | | 30 μg | 1.33 ± 0.87 | 0.034 | 1.05 ± 0.77 | 0.039 |
| | | 50 μg | 1.36 ± 0.71 | 0.010 | 1.05 ± 0.65 | 0.016 |
| Synthetic Consensus Muc16 Dual Promoter (pGX1439) CD8+ and CD8+CD107a+ T cells | | | | | | |
| pGX0001 | Naive | 30 μg | 0.13 ± 0.15 | n/a | 0.05 ± 0.04 | n/a |
| pGX1439 | Immunized | 10 μg | 1.36 ± 0.62 | 0.004 | 1.04 ± 0.65 | 0.018 |
| | | 30 μg | 2.07 ± 1.77 | 0.089 | 1.68 ± 1.54 | 0.094 |
| | | 50 μg | 1.19 ± 0.69 | 0.020 | 0.93 ± 0.68 | 0.038 |

Statistical significance assumed at p ≤ 0.05.

p-values reported are relative to naïve (pGX0001 immunized mice).

Synthetic consensus MUC16 partial length constructs elicited strong responses in the CD4$^+$ T cell compartment (FIGS. 25A-25B and FIGS. 26A-26B). The magnitude of synthetic consensus MUC16 pGX1436 construct specific CD4$^+$ T cells was dose-independent (FIG. 25A). Specifically, synthetic consensus MUC16 pGX1436 CD4$^+$ T cells were 1.74%±0.79%, 2.18%±1.15%, and 1.32%±1.74% at the 10 μg, 30 μg, and 50 μg dose amounts, respectively. Synthetic consensus MUC16 pGX1436 CD4$^+$ T cells were significantly greater than naïve (0.17%±0.10%) at the 10 μg (p=0.003) and 30 μg (p=0.007) dose amounts but not at the 50 μg (p=0.359) dose amount of pGX1436. Synthetic consensus MUC16 pGX1436 specific CD4$^+$ T cell responses consisted mainly of IFNγ$^+$IL-2$^+$TNFα$^+$, IFNγ$^+$IL-2$^-$TNFα$^+$ or IFNγ$^+$IL-2$^-$TNFα$^-$ producing CD4$^+$ T cells. The frequency of pGX1436 antigen specific CD4$^+$CD107a$^+$ T cells was 0.45%±0.28%, 0.31%±0.26%, and 0.23%±0.30% in the 10 μg (p=0.020), 30 μg (p=0.080), and 50 μg (p=0.369) dose amount groups, respectively (FIG. 25B). The cytokine profile of pGX1436 specific CD4$^+$CD107a$^+$ T cells was similar across dose amount groups and was comprised mainly of IFNγ$^+$IL-2$^+$TNFα$^+$ and IFNγ$^+$IL-2$^-$TNFα$^+$ cells (FIG. 25B). The frequency of antigen specific CD4$^+$ T cells with cytolytic potential is further detailed in Table 19.

Figure 26A:
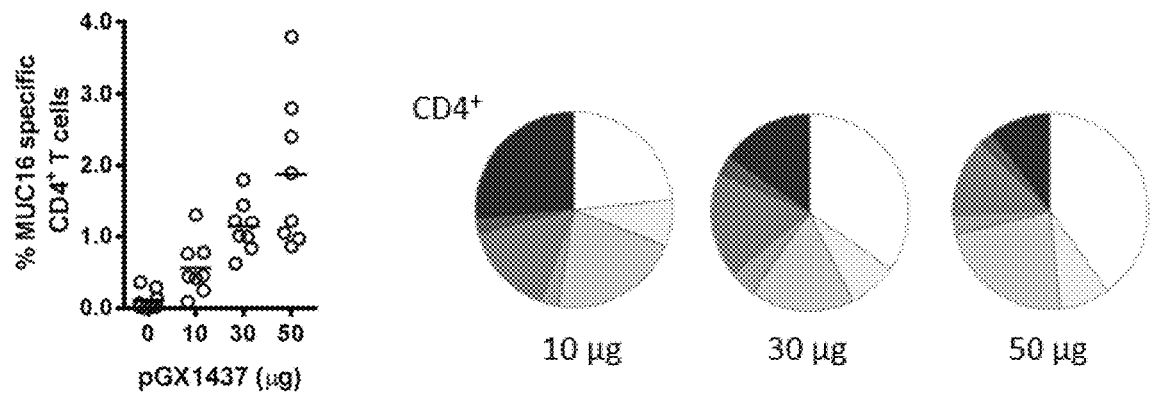
FIGS. 26A-26B illustrate cellular immune responses induced by pGX1437 in the CD4+ T cell compartment (FIG. 26A) and the cytolytic immune responses and profile of specific CD4+ T cell responses for partial length construct pGX1437 (FIG. 26B).
Figure 26B:
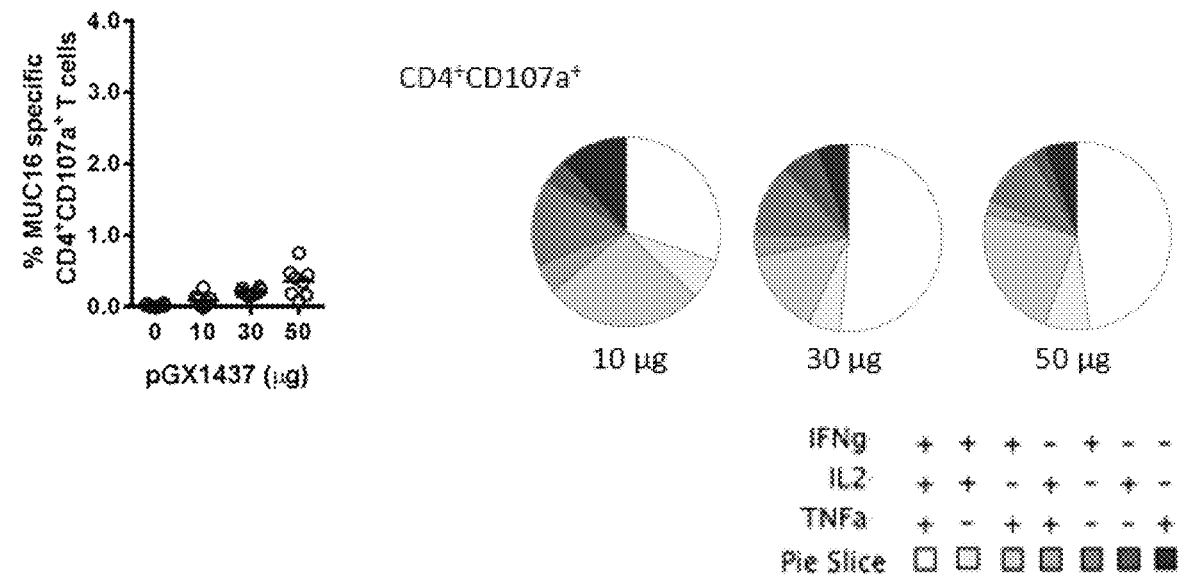

The magnitude of synthetic consensus MUC16 pGX1437 construct specific CD4$^+$ T cells was dose-dependent (FIG. 26A). Specifically, synthetic consensus MUC16 pGX1437 CD4+ T cells were 0.56%±0.38%, 1.14%±0.36%, and 1.87%±1.05% at the 10 30m, and 50 μg dose amounts, respectively. Synthetic consensus MUC16 pGX1437 CD4+ T cells were significantly greater than naïve (0.21%±0.14%) at the 30 μg (p<0.001) and 50 μg (p=0.011) but not at the 10 μg (p=0.063) dose amount of pGX1437. Synthetic consensus MUC16 pGX1437 specific CD4+ T cell responses consisted mainly of IFNγ$^+$IL-2$^+$TNFα$^+$, IFNγ$^+$IL-2$^-$TNFα$^+$ or IFNγ$^-$IL-2$^-$TNFα$^+$ producing CD4$^+$ T cells. The frequency of pGX1437 antigen specific CD4$^+$CD107a$^+$ T cells was 0.09%±0.09%, 0.21%±0.05%, and 0.36%±0.21% in the 10 μg (p=0.335), 30 μg (p<0.001), and 50 μg (p=0.016) dose amount groups, respectively (FIG. 26B). The cytokine profile of pGX1437 specific CD4$^+$CD107a$^+$ T cells was similar across dose amount groups and was comprised mainly of IFNγ$^+$IL-2$^+$TNFα$^+$ and IFNγ$^+$IL-2$^-$TNFα$^+$ cells (FIG. 26B). The frequency of antigen specific CD4$^+$ T cells with cytolytic potential is further detailed in Table 19.

Figure 27A:
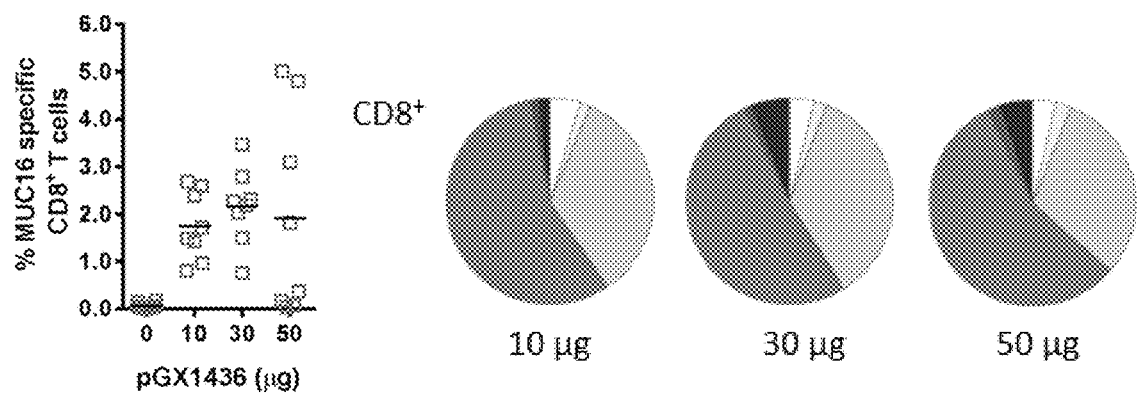
FIGS. 27A-27B illustrate cellular immune responses induced by pGX1436 in the CD8+ T cell compartment (FIG. 27A) and cytolytic immune responses and profile of specific CD8+ T cell responses for partial length constructs (FIG. 27B).
Figure 27B:
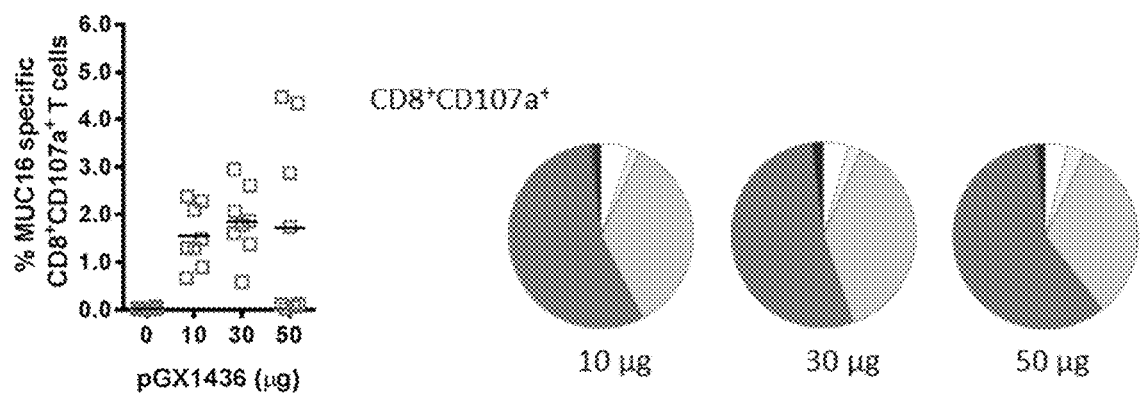

Synthetic consensus MUC16 partial length constructs elicited robust responses in the CD8$^+$ T cell compartment (FIGS. 27A-27B and FIGS. 28A-28B). The magnitude of synthetic consensus MUC16 pGX1436 construct specific CD8$^+$ T cells was dose-independent (FIG. 27A). Specifically, synthetic consensus MUC16 pGX1436 CD8$^+$ T cells were 1.76%±0.73%, 2.17%±0.81%, and 1.92%±2.13% at the 10 30 and 50 μg dose amounts, respectively. Synthetic consensus MUC16 pGX1436 CD8$^+$ T cells were significantly greater than naïve (0.06%±0.08%) at the 10 μg (p=0.002) and 30 μg (p=0.001) but not at the 50 μg (p=0.192) dose amounts of pGX1436. Synthetic consensus MUC16 pGX1436 specific CD8$^+$ T cell responses consisted mainly of IFNγ$^+$IL-2$^-$TNFα$^-$ or IFNγ$^+$IL-2$^-$TNFα$^+$ producing CD8+ T cells. The frequency of pGX1436 antigen specific CD8$^+$CD107a$^+$ T cells was 1.55%±0.64%, 1.86%±0.73%, and 1.72%±1.95% in the 10 μg (p=0.001), 30 μg (p=0.001), and 50 μg (p=0.193) dose amount groups, respectively (FIG. 26B). The cytokine profile of pGX1436 specific CD8$^+$CD107a$^+$ T cells was similar across dose amount groups and was comprised mainly of IFNγ$^+$IL-2$^-$TNFα$^-$ and IFNγ$^+$IL-2$^-$TNFα$^+$ cells (FIG. 27B). Overall, CD8$^+$ T cell responses to Region 1 induced by pGX1435 are significantly lower than pGX1436 (FIG. 29A). The frequency of antigen specific CD8$^+$ T cells with cytolytic potential is further detailed in Table 20.

Figure 28A:
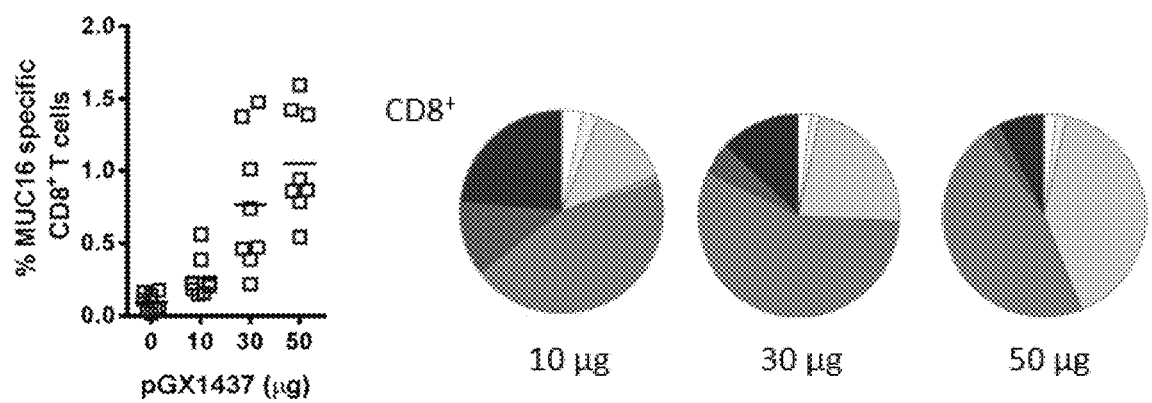
FIGS. 28A-28B illustrate cellular immune responses induced by pGX1437 in the CD8+ T cell compartment (FIG. 28A) and the cytolytic immune responses and profile of specific CD8+ T cell responses for partial length constructs (FIG. 28B).
Figure 28B:
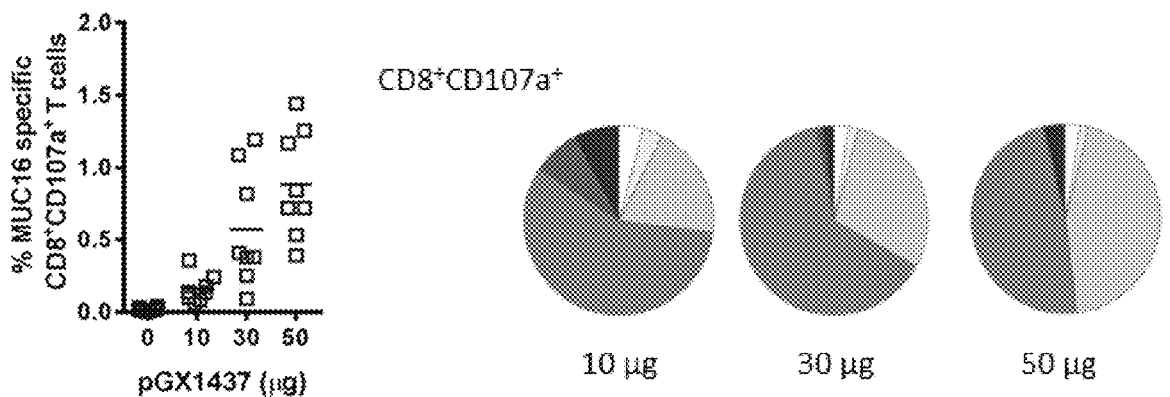

The magnitude of synthetic consensus MUC16 pGX1437 construct specific CD8$^+$ T cells was dose-dependent (FIG. 28A). Specifically, synthetic consensus MUC16 pGX1437 CD8$^+$ T cells were 0.26%±0.14%, 0.77%±0.47%, and 0.89%±0.37% at the 10 μg, 30 μg, and 50 μg dose amounts, respectively. Synthetic consensus MUC16 pGX1437 CD8$^+$ T cells were significantly greater than naïve (0.07%±0.07%) at the 30 μg (p=0.025) and 50 μg (p=0.001) but not at the 10 μg (p=0.069) dose amount of pGX1437. Synthetic consensus MUC16 pGX1437 specific CD8$^+$ T cell responses consisted mainly of IFNγ$^+$IL-2$^-$ TNFα$^+$ or IFNγ$^+$IL-2$^-$TNFα$^-$ producing CD8$^+$ T cells. The frequency of pGX1437 antigen specific CD8$^+$CD107a$^+$ T cells was 0.16%±0.10%, 0.58%±0.40%, and 0.89%±0.37% in the 10 μg (p=0.022), 30 μg (p=0.030), and 50 μg (p=0.002) dose amount groups, respectively (FIG. 28B). The cytokine profile of pGX1437 specific CD8$^+$CD107a$^+$ T cells was similar across dose amount groups and was comprised mainly of IFNγ$^+$IL-2$^-$TNFα$^-$ and IFNγ$^+$IL-2$^-$TNFα$^+$ cells (FIG. 28B). Overall, CD8$^+$ T cell responses to Region 2 induced by pGX1435 and pGX1438 are significantly lower than pGX1437 (FIG. 29B). The frequency of antigen specific CD8$^+$ T cells with cytolytic potential is further detailed in Table 20.

TABLE 19

| Product Code | Group | Dose amount | % CD4$^+$ ± Std. Dev. | % CD4$^+$ p-value | % CD4$^+$CD107a$^+$ ± Std. Dev. | % CD4$^+$CD107a$^+$ p-value |
|---|---|---|---|---|---|---|
| Synthetic Consensus Muc16 "Region 1" (pGX1436) CD4$^+$ and CD4$^+$CD107a$^+$ T cells ||||||||
| pGX0001 | Naïve | 30 μg | 0.17 ± 0.10 | n/a | 0.04 ± 0.03 | n/a |
| pGX1436 | Immunized | 10 μg | 1.74 ± 0.79 | 0.003 | 0.45 ± 0.28 | 0.020 |
|  |  | 30 μg | 2.18 ± 1.15 | 0.007 | 0.31 ± 0.26 | 0.080 |
|  |  | 50 μg | 1.32 ± 1.74 | 0.359 | 0.23 ± 0.30 | 0.369 |
| Synthetic Consensus "Muc16 Region 2" (pGX1437) CD4$^+$ and CD4$^+$CD107a$^+$ T cells ||||||||
| pGX0001 | Naïve | 30 μg | 0.21 ± 0.14 | n/a | 0.02 ± 0.02 | n/a |
| pGX1437 | Immunized | 10 μg | 0.56 ± 0.38 | 0.063 | 0.09 ± 0.09 | 0.335 |
|  |  | 30 μg | 1.14 ± 0.36 | <0.001 | 0.21 ± 0.05 | <0.001 |
|  |  | 50 μg | 1.87 ± 1.05 | 0.011 | 0.36 ± 0.21 | 0.016 |

Statistical significance assumed at p ≤ 0.05.

p-values reported are relative to naïve (pGX0001 immunized mice).

TABLE 20

| Product Code | Group | Dose amount | % CD8+ ± Std. Dev. | % CD8+ p-value | % CD8+CD107a+ ± Std. Dev. | % CD8+CD107a+ p-value |
|---|---|---|---|---|---|---|
| Synthetic Consensus Muc16 "Region 1" (pGX1436) CD8+ and CD8+CD107a+ T cells ||||||||
| pGX0001 | Naive | 30 µg | 0.06 ± 0.08 | n/a | 0.03 ± 0.03 | n/a |
| pGX1436 | Immunized | 10 µg | 1.76 ± 0.73 | 0.002 | 1.55 ± 0.64 | 0.001 |
|  |  | 30 µg | 2.17 ± 0.81 | 0.001 | 1.86 ± 0.73 | 0.001 |
|  |  | 50 µg | 1.92 ± 2.13 | 0.192 | 1.72 ± 1.95 | 0.193 |
| Synthetic Consensus "Muc16 Region 2" (pGX1437) CD8+ and CD8+CD107a+ T cells ||||||||
| pGX0001 | Naive | 30 µg | 0.07 ± 0.07 | n/a | 0.03 ± 0.02 | n/a |
| pGX1437 | Immunized | 10 µg | 0.26 ± 0.14 | 0.069 | 0.16 ± 0.10 | 0.022 |
|  |  | 30 µg | 0.77 ± 0.47 | 0.025 | 0.58 ± 0.40 | 0.030 |
|  |  | 50 µg | 0.89 ± 0.37 | 0.001 | 0.89 ± 0.37 | 0.002 |

Statistical significance assumed at $p \leq 0.05$.
p-values reported are relative to naïve (pGX0001 immunized mice).

Statistical Analysis

Statistical analysis was completed using IBM SPSS Statistics 22 (IBM Corporation). Analysis between groups was performed using an ANOVA with post-hoc Tukey's Honest Significant Difference (HSD) to adjust for multiple comparisons. Homogeneity of variance was confirmed using the F statistic prior to multiple comparisons. For all statistical analysis, a p-value of 0.050 was considered significant.

CONCLUSION

Figures 30A, 30B, 30C:
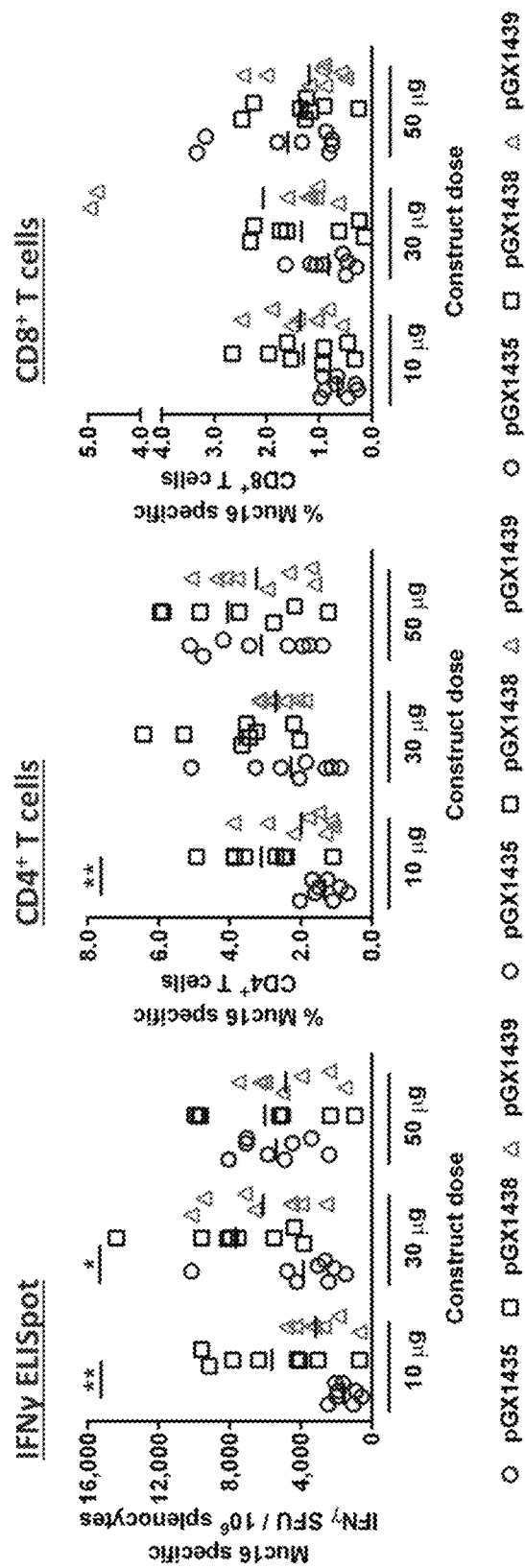
FIGS. 30A-30C provide a summary of IFNγ (FIG. 30A), CD4+ (FIG. 30B) and CD8+ T (FIG. 30C) cell data for full length constructs disclosed herein.

Overall, the full length MUC16 constructs pGX1438 (furin cleavage) and pGX1439 (dual promoter) induced more robust immune responses compared to pGX1435 (fusion) (FIGS. 30A-C). Compared to pGX1435, pGX1438 induced significantly more robust responses by IFNγ ELISpot at the 10 µg and 30 µg dose amounts. Also, in the CD4+ T cell compartment pGX1438 elicited significantly more robust responses compared to pGX1435 at the 10 µg dose amount. There were no other significant differences in the magnitude of response induced by the three full-length MUC16 constructs, however, there was a trend towards more robust CD8+ T cell responses induced by pGX1438 and pGX1439.

Furthermore, pGX1438 and pGX1439 induced responses to Region 1 equivalent to pGX1436 and induced responses to Region 2 equivalent to pGX1437 as determined by IFNγ ELISpot and in the CD4+ T cell compartment. Only pGX1439 induced responses equivalent to pGX1437 in the CD8+ T cell compartment.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modification to the disclosed embodiments, including without limitation those relating to the chemical structures, substituents, derivatives, intermediates, syntheses, compositions, formulations, or methods of use of the invention, may be made without departing from the spirit and scope thereof.

TABLE 21

Synthetic consensus MUC16 IRC + R59 DNA Coding Sequence

| SEQ ID NO. | SEQUENCE |
|---|---|
| 1 | atggactgga cctggattct gttcctggtg gcagcagcaa cccgcgtgca ctccacagca gcaggacctc tgctggtgcc attcaccctg aactttacca tcacaaatct gcagtacgag gaggatatgc accaccagg cagcagaaag ttcaacacca cagagagggt gctgcagggc ctgctgggac caatgtttaa gaataccagc gtgggcctgc tgtattccgg atgcaggctg acactgctgc gctccgagaa ggacggagca gcaaccggcg tggatgccat ctgtacacac aggctggacc ccaagagccc tggcctggat cgggagcagc tgtactggga gctgtcccag ctgaccaacg gcatcaagga gctgggcccc tacacactgg accgcaacag cctgtatgtg aatggcttta cccaccggag ctccgtgcca aataccagca cacccggcac ctccacagtg gatctgggca cctccggcac accatctagc ctgccttctc caaccgcagc aggaccactg ctggtgcctt tcacactgaa ctttaccatt accaatctgc agtatgaaga ggacatgagg catcctggca gcagaaagtt caacacgaca gagagagtgc tgcaaggcct gctgaagcca ctgtttaaga atacctctgt gggccccctg tatagtggct gtagactgac actgctgcgc cccgaaaaag atggcgccgc cactggagtc gacgccatct gtacacacag actggacccc aagtctcccg gcctgaacag agaacagctg tattgggaac tgagcaagct gaccaatggc atcacagagc tgggccctta caccctggac agaaactctc tgtatgtgaa tggcttcacc cacaggacat ctgtgcctac cacaagcacc ccaggcacct ccaccgtcga tctgggcacc agcggcacac ctttttagcct gccatcccct accaccgccg gaccactgct ggtgcccttc accctgaact ttaccataac caatctgcag tatgaggagg acatgcaccg gccccggcagc agaaagttca acactacaga gagagtgctg cagggcctgt tatcccctat ctttaagaat tcctctgtgg gccactgta cagcggatgc aggctgacct ctctgcggcc cgaaaaagac ggagcagcaa caggaatgga tgccgtgtgc ctgtaccacc caaacccaa gaggccaggc ctggatcgcg agcagctgta ttgggagctg agccagctga cccacaatat cacagagctg ggccccctact ctctggacag ggatagcctg tatgtgaacg gcttcaccca ccagaattcc |

TABLE 21-continued

Synthetic consensus MUC16 IRC + R59 DNA Coding Sequence

SEQ
ID
NO. SEQUENCE

```
gtgcccacca catctacacc tggcaccagc acagtgtact gggccaccac aggcacccct
agctcctttc caggacacac agcacctgga ccactgctga tcccattcac cctgaacttt
accattacaa atctgcacta tgaggagaac atgcagcacc ccggcagccg caagttcaat
accacagagc gggtgctgca aggcctgctg aagccgctgt ttaagaacac cagcgtggga
cctctgtact ctggctgtcg cctgacactg ctgcggcccg agaagcatgg cgcagcaacc
ggcgtggacg ctatttgcac ccacagactg gaccctaagg ccccaggcct ggatagggag
cgcctgtatt gggaactgtc tcagctgacc aattctatca cagagctggg accatacacc
ctggacaggg attctctgta cgtgaacggc ttcaatccac ggtctagcgt gcccaccaca
agcacccctg gcacctccac agtgcacctg gccacctctg gcacaccctc ctctctgcct
ggacacaccg caagcccct gctggtgctg ttcacaatca actttaccat tactaatctg
agatacgagg agaacatgca ccaccctggc tccagaaagt tcaatactac cgaaagggtg
ctgcaaggcc tgctgcgccc agtgtttaag aacacttccg tgggccccct gtatagcggc
tgtaggctga cactgctgcg ccccaagaag gatggcgcag caaccaaggt cgacgctatc
tgtacataca ggcccgaccc taaatcccca ggcctggacc gggagcagct gtattgggag
ctgtctcagc tgaccactc cattaccgaa ctgggaccct acacctggac cagagattcc
ctgtacgtga atggcttcac acagaggagc tccgtgccta ccacatccat cccaggaacc
cctacagtgg acctgggcac ctccggaacc ccagtgtcta agccaggacc atctgccgca
agccacctgc tgatcctgtt caccctgaac tttaccataa cgaatctgcg gtacgaggag
aacatgtggc caggctcccg gaagttcaat actaccgaga gagtgctgca aggcctgctg
aggcctctgt ttaagaacac tagcgtgggc ccactgtatt ccggctctcg gctgaccctg
ctgcggcccg aaaaagatgg agaggccaca ggcgtggatg ccatctgcac ccacagacct
gacccaacag gacctggcct ggacagggag cagctgtacc tggagctgtc acagctgact
cactccatta ccgagctggg ccctatact ctggataga actccctgta cgtcaacggc
ttcacccacc ggtctagcgt gccaaccaca tctacaggcg tggtgagcga ggaaccctc
accctgaact tcaccatcaa caatctgagg tacatggcag acatgggaca gccaggctct
ctgaagttca acatcaccga taatgtgatg aagcacctgc tgagccctct gtttcagcgg
agcagcctgg gagcaaggta caccggatgc cgcgtgatcg ccctgcggtc cgtgaagaac
ggagcagaga cacgggtgga cctgctgtgc acatatctgg agcctctgag cggaccaggc
ctgcccatca agcaggtgtt ccacgagctg tctcagcaga cccacggaat cacaaggctg
ggaccctact ccctggacaa ggattctctg tacctgaacg ctataatga gcctggcctg
gacgagcccc ctaccacacc caagcctgcc accacatttc tgccacccct gagcgaggca
accacagcaa tgggatacca cctgaagacc ctgacactga acttccacat cagcaatctg
cagtattccc ccgatatggg caagggctct gccaccttta acagcacaga gggcgtgctg
cagcacctgc tgcggcccct gttccagaag agctccatgg gcccttttta cctgggctgc
cagctgatct ccctgaggcc tgaaaaagat ggagcagcaa ccggagtgga taccacatgt
acataccacc cagacccgt gggaccaggc ctggatatcc agcagctgta ctgggaactg
tcccagctga ctcacggcgt gacacagctg ggcttctacg tgctggaccg cgattccctg
tttatcaacg gctacgcccc tcagaatctg tctatccggg gcgagtatca gatcaacttc
cacatcgtga actggaatct gagcaatcct gacccaacct ctagcgagta catcgccctg
ctgcgcgaca tccaggataa ggtgaccaca ctgtataagg gctcccagct gcacgacacc
ttccggtttt gcctggtgac caacctgaca atggattcta tgctggtgac agtgaaggcc
ctgttctcct ctaacctgga ccccagcctg gtggagcagg tgtttctgga taagaccctg
aatgccagct cccactggct gggctccacc taccagctgg tggacatcca cgtgacagag
atggagccaa gcgtgtacca gcccacctct agctcctcta cacagcactt ctacctgaac
tttaccataa ctaatctgcc ctatagccag gatatcgccc agcctggcac cacaaactac
cagcggaaca agagaaatat cgaggacgcc ctgaaccagc tgttcagaaa tagctccatc
aagtcctatt tctctgattg ccaggtgagc acctttaggt ccgtgcctaa ttctcaccac
acaggcgtgg actccctgtg cgccttttct ccactggcaa ggagagtgga tagggtggca
atctacgagg agttcctgag gatgacccgc gccggaacac agtgcaggc ctttaccctg
gacagatcta gcgtgctggt ggatggctat agccctaaca ggaatgagcc actgaccggc
aactccgacc tgcccttctg ggccatcatc ctgatctgtc tggcaggcct gctgggcctg
atcacctgcc tgatctgtgg ctttctggtg tgataa
```

TABLE 22

Synthetic consensus MUC16 IRC + R59 Protein Sequence

SEQ
ID
NO. SEQUENCE

2  MDWTWILFLVAAATRVHSTAAGPLLVPFTLNFTITNLQYEEDMHHPGSRKFNTTERVL
   QGLLGPMFKNTSVGLLYSGCRLTLLRSEKDGAATGVDAICTHRLDPKSPGLDREQLY
   WELSQLTNGIKELGPYTLDRNSLYVNGFTHRSSVPNTSTPGTSTVDLGTSGTPSSLPSPT
   AAGPLLVPFTLNFTITNLQYEEDMRHPGSRKFNTTERVLQGLLKPLFKNTSVGPLYSGC
   RLTLLRPEKDGAATGVDAICTHRLDPKSPGLNREQLYWELSKLTNGITELGPYTLDRN
   SLYVNGFTHRTSVPTTSTPGTSTVDLGTSGTPFSLPSPTTAGPLLVPFTLNFTITNLQYEE
   DMHRPGSRKFNTTERVLQGLLSPIFKNSSVGPLYSGCRLTSLRPEKDGAATGMDAVCL
   YHPNPKRPGLDREQLYWELSQLTHNITELGPYSLDRDSLYVNGFTHQNSVPTTSTPGTS
   TVYWATTGTPSSFPGHTAPGPLLIPFTLNFTITNLHYEENMQHPGSRKFNTTERVLQGL

TABLE 22-continued

Synthetic consensus MUC16 IRC + R59 Protein Sequence

| SEQ ID NO. | SEQUENCE |
|---|---|
| | LKPLFKNTSVGPLYSGCRLTLLRPEKHGAATGVDAICTHRLDPKGPGLDRERLYWELS QLTNSITELGPYTLDRDSLYVNGFNPRSSVPTTSTPGTSTVHLATSGTPSSLPGHTASPL LVLFTINFTITNLRYEENMHHPGSRKFNTTERVLQGLLRPVFKNTSVGPLYSGCRLTLL RPKKDGAATKVDAICTYRPDPKSPGLDREQLYWELSQLTHSITELGPYTLDRDSLYVN GFTQRSSVPTTSIPGTPTVDLGTSGTPVSKPGPSAASHLLILFTLNFTITNLRYEENMWP GSRKFNTTERVLQGLLRPLFKNTSVGPLYSGSRLTLLRPEKDGEATGVDAICTHRPDPT GPGLDREQLYLELSQLTHSITELGPYTLDRDSLYVNGFTHRSSVPTTSTGVVSEEPFTLN FTINNLRYMADMGQPGSLKFNITDNVMKHLLSPLFQRSSLGARYTGCRVIALRSVKNG AETRVDLLCTYLQPLSGPGLPIKQVFHELSQQTHGITRLGPYSLDKDSLYLNGYNEPGL DEPPTTPKPATTFLPPLSEATTAMGYHLKTLTLNFTISNLQYSPDMGKGSATFNSTEGV LQHLLRPLFQKSSMGPFYLGCQLISLRPEKDGAATGVDTTCTYHPDPVGPGLDIQQLY WELSQLTHGVTQLGFYVLDRDSLFINGYAPQNLSIRGEYQINFHIVNWNLSNPDPTSSE YIALLRDIQDKVTTLYKGSQLHDTFRFCLVTNLTMDSMLVTVKALFSSNLDPSLVEQV FLDKTLNASSHWLGSTYQLVDIHVTEMEPSVYQPTSSSSTQHFYLNFTITNLPYSQDIA QPGTTNYQRNKRNIEDALNQLFRNSSIKSYFSDCQVSTFRSVPNSHHTGVDSLCAFSPL ARRVDRVAIYEEFLRMTRAGTQLQAFTLDRSSVLVDGYSPNRNEPLTGNSDLPFWAIIL ICLAGLLGLITCLICGFLV |

TABLE 23

Synthetic consensus MUC16 RMC DNA Coding Sequence

| SEQ ID NO. | SEQUENCE |
|---|---|
| 3 | atggattgga cttggattct gttcctggtc gccgccgcaa ctcgggtgca ttctactgct gctgggccac tgctggtgcc ttttacactg aacttcacca tcacaaatct gcagtacgag gaggacatgc accaccctgg ctctcggaag ttcaacacca cagagagagt gctgcagggc ctgctgggcc caatgtttaa gaataccagc gtgggcctgc tgtattccgg atgccggctg acactgctga tcccagaaa ggacggagca gcaaccggag tggatgccat ctgtacacac aggctggacc caaagtcccc aggcctggat agagagcagc tgtactggga gctgtctcag ctgaccaacg gcatcaagga gctgggcccc tacacactgg accggaacag cctgtatgtg aatggcttta cccacagaag ctccgtgcca ataccagca cacccggcac ctccacagtg gatctgggca cctctggcac accttctagc ctgccaagcc ctaccgcagc aggaccactg ctggtgccct tcacactgaa ctttaccatt accaatctgc agtatgaaga ggacatgagg cacccaggct cccgcaagtt caacactacc gagcgggtgc tgcaaggcct gctgaagcct ctgtttaaga atacctctgt gggcccactg tatagtggct gccggctgac actgctgcgg cccgaaaaag acggagcagc aaccggcgtg gatgctattt gcacccagag ctggacccc aagagcccag gcctgaaccg cgaacagctg tattgggagc tgtccaagct gacccaatggc atcacagagc tgggcccta cacccctggac agaaattccc tgtacgtgaa tggcttcacc caccgcacat ctgtgcctac cacaagcacc ccaggcacct ccacagtgga tctgggcacc tccggcacac ccttttccct gccatctcca accacagcag gacctctgct ggtgccattc accctgaact ttaccattac taatctgcag tatgaagaag acatgcacag gcctggctct cgcaagttca acactactga gagggtgctg cagggcctgt taagcccaat ctttaagaat tcctctgtgg gccctctgta ttccggatgc aggctgacct ctctgcgccc agaaaaagat ggagcagcaa caggaatgga tgccgtgtgc ctgtaccacc taacccaaa gcggcccggc ctggacaggg agcagctgta ttgggaactg agccagctga cccacaatat cacagagctg ggcccttact ctctggaccg cgatagcctg tatgtgaacg gcttcaccca cagaattcc gtgcccacca tctctacacc tggcaccagc acagtgtact gggccaccac aggcaccccc agctcctttc ctggacacac agcaccagga cctctgctga tcccttcac cctgaacttt accataacaa atctgcacta tgaggagaac atgcagcacc tggcagcag aagttcaat accacagagc gcgtgctgca aggcctgctg aagccgctgt taagaacac agcgtggga ccactgtaca gcggctgcag gctgaccctg ctgcgcctg agaagcatgg cgccgccacc ggcgtggatg ctatctgcac acatagactg accccaagg gacctggcct ggatagggag agactgtact gggaactgtc ccagctgacc aactcaatta cagagctggg cccatacacc ctggaccggg attctctgta cgtgaacgg ttcaatccaa gatctagcgt ccctaccaca tctaccctg gacaagtac cgtgcatctg ctacaagcg gaactccttc aagtctgcct ggacactgat aa |

TABLE 24

Synthetic consensus MUC16 RMC Protein Sequence

| SEQ ID NO. | SEQUENCE |
|---|---|
| 4 | MDWTWILFLVAAATRVHSTAAGPLLVPFTLNFTITNLQYEEDMHHPGSRKFNTTERVL QGLLGPMFKNTSVGLLYSGCRLTLLRSEKDGAATGVDAICTHRLDPKSPGLDREQLY WELSQLTNGIKELGPYTLDRNSLYVNGFTHRSSVPNTSTPGTSTVDLGTSGTPSSLPSPT AAGPLLVPFTLNFTITNLQYEEDMRHPGSRKFNTTERVLQGLLKPLFKNTSVGPLYSGC RLTLLRPEKDGAATGVDAICTHRLDPKSPGLNREQLYWELSKLTNGITELGPYTLDRN SLYVNGFTHRTSVPTTSTPGTSTVDLGTSGTPFSLPSPTTAGPLLVPFTLNFTITNLQYEE DMHRPGSRKFNTTERVLQGLLSPIFKNSSVGPLYSGCRLTSLRPEKDGAATGMDAVCL YHPNPKRPGLDREQLYWELSQLTHNITELGPYSLDRDSLYVNGFTHQNSVPTTSTPGTS TVYWATTGTPSSFPGHTAPGPLLIPFTLNFTITNLHYEENMQHPGSRKFNTTERVLQGL LKPLFKNTSVGPLYSGCRLTLLRPEKHGAATGVDAICTHRLDPKGPGLDRERLYWELS QLTNSITELGPYTLDRDSLYVNGFNPRSSVPTTSTPGTSTVHLATSGTPSSLPGH |

TABLE 25

Synthetic consensus MUC16 NRC DNA Coding Sequence

| SEQ ID NO. | SEQUENCE |
|---|---|
| 5 | atggactgga cttggattct gttcctggtc gctgccgcca cccgcgtgca tagtgccgca tctcacctgc tgattctgtt caccctgaac ttcaccatca caaatctgcg gtacgaggag aacatgtggc caggcagccg caagttcaat accacagagc gggtgctgca gggcctgctg cggcccctgt ttaagaacac ctccgtgggc ccctgtatt ctggcagcag gctgaccctg ctgcgcccag agaaggacgg agaggcaaca ggcgtggatg ccatctgcac ccacaggcct gacccaacag gaccaggcct ggatagggag cagctgtacc tggagctgag ccagctgacc cactccatca cagagctggg accatacacc ctggacaggg attccctgta tgtgaacggc tttacccaca gaagctccgt gccaccaca tctacaggcg tggtgagcga ggagcccttc accctgaact tcaccatcaa caatctgagg tacatggcag acatgggaca gccaggcagc ctgaagttca acatcaccga taatgtgatg aagcacctgc tgtccccctct gtttcagcgg tctagcctgg agcaaggta caccggctgc agagtgatcg ccctgaggtc cgtgaagaac ggagcagaga cacgggtgga cctgctgtgc acatatctgc agcctctgag cggaccaggc ctgcctatca agcaggtgtt ccacgagctg tctcagcaga cccacggaat cacgcctg ggaccttact ccctggacaa ggattctctg tacctgaacg ctataatga gccaggcctg gacgagcccc taccacacc aagcctgcc accacattc tgccaccct gagcgaggca accacagcaa tgggatacca cctgaagacc ctgacactga acttcaccat cagcaatctg cagtattccc ccgatatggg caagggctct gccaccttta atagcacaga gggcgtgctg cagcacctgc tgaggcctct gttccagaag tcctctatgg gcccttcta cctgggatgc cagctgatct ccctgcgccc tgagaaggac ggagcagcaa ccggagtgga taccacatgt acataccacc cagaccccgt gggaccaggc ctggatatcc agcagctgta ttgggaactg tcccagctga cccacggcgt gacacagctg ggcttctatg tgctggaccg ggattctctg tttatcaacg gctacgcccc tcagaatctg agcatcagag gcgagtatca gatcaacttc cacatcgtga actggaatct gtctaatcct gatccaacca gctccgagta catcgccctg ctgcgggaca tccaggataa ggtgaccaca ctgtataagg cagccagct gcacgacacc ttcagatttt gtctggtgac caacctgaca atggattcca tgctggtgac agtgaaggcc ctgttctcta gcaacctgga cccttctctg gtggagcagg tgtttctgga taagaccctg aatgcctcct ctcactggct gggctctacc taccagctgg tggacatcca cgtgacagag atggagccaa gcgtgatca gcccaccagc tcctctagca cacagcactt ctacctgaac tttaccatca caaatctgcc ctatagccag gatatcgccc agcctggcac cacaaaactac cagaggaaca agcgcaatat cgaggacgcc ctgaaccagc tgttcaggaa ttccctctatc aagtcctatt tctctgattg ccaggtgagc acctttcgct ccgtgccaaa ttctcaccac acaggcgtgg actccctgtg cgccttttct ccctggcac ggagagtgga tagggtggca atctacgagg agttcctgcg gatgaccaga gccggcacac agctgcaggc ctttaccctg gacaggagct ccgtgctggt ggatggctat agccctaacc gcaatgagcc actgacaggc aattccgacc tgcccttctg gccatcatc ctgatttgcc tggctggact gctgggctg attacctgtc tgatttgtgg gttcctggtg tgataa |

TABLE 26

Synthetic consensus MUC16 NRC Protein Sequence

| SEQ ID NO. | SEQUENCE |
|---|---|
| 6 | MDWTWILFLVAAATRVHSTAAGPLLVPFTLNFTITNLQYEEDMHHPGSRKFNTTERVL<br>QGLLGPMFKNTSVGLLYSGCRLTLLRSEKDGAATGVDAICTHRLDPKSPGLDREQLY<br>WELSQLTNGIKELGPYTLDRNSLYVNGFTHRSSVPNTSTPGTSTVDLGTSGTPSSLPSPT<br>AAGPLLVPFTLNFTITNLQYEEDMRHPGSRKFNTTERVLQGLLKPLFKNTSVGPLYSGC<br>RLTLLRPEKDGAATGVDAICTHRLDPKSPGLNREQLYWELSKLTNGITELGPYTLDRN<br>SLYVNGFTHRTSVPTTSTPGTSTVDLGTSGTPFSLPSPTTAGPLLVPFTLNFTITNLQYEE<br>DMHRPGSRKFNTTERVLQGLLSPIFKNSSVGPLYSGCRLTSLRPEKDGAATGMDAVCL<br>YHPNPKRPGLDREQLYWELSQLTHNITELGPYSLDRDSLYVNGFTHQNSVPTTSTPGTS<br>TVYWATTGTPSSFPGHTAPGPLLIPFTLNFTITNLHYEENMQHPGSRKFNTTERVLQGL<br>LKPLFKNTSVGPLYSGCRLTURPEKHGAATGVDAICTHRLDPKGPGLDRERLYWELS<br>QLTNSITELGPYTLDRDSLYVNGFNPRSSVPTTSTPGTSTVHLATSGTPSSLPGH |

TABLE 27

Synthetic consensus MUC16 IRC DNA Coding Sequence

| SEQ ID NO. | SEQUENCE |
|---|---|
| 7 | atggactgga cctggattct gttcctggtg gcagcagcaa ccagggtgca ctccacagca<br>gcaggacctc tgctggtgcc attcaccctg aactttacca tcacaaatct gcagtacgag<br>gaggatatgc accccccgg cagccgcaag ttcaacacca cagagcgggt gctgcagggc<br>ctgctgggac ctatgtttaa gaataccagc gtgggcctgc tgtattccgg atgcaggctg<br>acactgctgc gctccgagaa ggacggagca gcaaccggtg tggatgccat ctgtacacac<br>aggctggacc caaagtctcc cggcctggat cgcgagcagc tgtactggga gctgagccag<br>ctgaccaacg gcatcaagga gctgggcccc tacacactgg accggaacag cctgtatgtg<br>aatggcttca cccacagaag ctccgtgcca atacctcca cacccggcac tctacagtg<br>gatctgggca cctctggcac accctctagc ctgcctagcc caaccgcagg aggaccactg<br>ctggtgcctt tcacactgaa ctttaccatt accaatctgc agtatgaaga ggacatgcgg<br>caccctggca gcagaaagtt caacactacc gagcgcgtgc tgcaaggcct gctgaagcca<br>ctgtttaaga atacctctgt gggcccctg tatagtggct gtagactgac actgctgcgc<br>cctgaaaaag atggcgccgc cactggagtc gacgctattt gcacccacag gctggacccc<br>aagtccccag gcctgaacag agaacagctg tattgggagc tgtctaagct gaccaatggc<br>atcacagagc tgggcccata cacccctggac aggaactctc tgtacgtcaa tggcttcacc<br>caccgcacaa gcgtgcctac cacatccacc ccaggcacct ctaccgtcga tctgggcacc<br>agcggcacac cattttcct gccatctcct accaccgccg gaccactgc ggtgccttc<br>accctgaact ttaccataac caatctgcag tatgaggagg acatgcaccg gcccggctct<br>agaaagttca acactactga acggtgctg caaggcctgt taagccctat ctttaagaat<br>tcctctgtgg gcccactgta cagcggatgc aggctgacct ctctgcggcc cgaaaagac<br>ggagcagcaa caggaatgga tgccgtgtgc ctgtaccacc caaacccaa gaggcctggc<br>ctggacagag agcagctgta ttgggaactg tcccagctga ccacaatat cacagagctg<br>ggcccctaca gcctggacag agattccctg tatgtgaacg gcttcaccca ccagaattct<br>gtgcccacca caagcacacc tggcacctcc acagtgtact gggcaccac aggcacccct<br>agctcctttc caggacacac agcacctgga ccactgctga tccctttcac cctgaacttt<br>accattacaa atctgcacta tgaggagaac atgcagcacc cagcagcag aaagttcaat<br>accacagaga gggtgctgca aggcctgctg aagccgctgt ttaagaacac cagcgtggga<br>cctctgtact ctgctgtcg cctgacactg ctgcggccg agaagcatgg cgcagcaacc<br>ggcgtggacg ctatttgcac tcatagactg gaccccaagg gacctggcct ggatagggag<br>agactgtact gggaactgtc tcagctgacc aattccatta cagagctggg cccttacacc<br>ctggaccggg acagcctgta cgtcaacggc ttcaatccaa gatctagcgt gcccaccaca<br>tccacccctg gcacctctac agtgcacctg gccaccagcg gaacaccctc ctctctgcct<br>ggacacaggg gaaggaagcg gagaagcgcc gcatcccacc tgctgatcct gttcaccctg<br>aactttacca taacgaatct gagatacgag gagaacatgt ggcctggctc ccgcaagttc<br>aatactaccg aacgggtgct gcagggcctg ctgcggcccc tgtttaagaa cacttccgtg<br>ggcccctgt attctggcag caggctgacc ctgctgcgcc cagagaagga cggagaggca<br>acaggcgtgg atgccatctg cacccacagg cccgaccta caggaccagg cctggatagg<br>gagcagctgt acctggagct gtcccagctg actcactcaa ttaccgaact gggaccttac<br>accctggaca gggatagtct gtacgtgaat ggcttcaccc atcgcagctc cgtgccaacc<br>acatctacag gcgtggtgag cgaggaaccc ttcacccctga acttcaccat caacaatctg<br>aggtacatgg ccgacatggg ccagccaggc tccctgaagt caacatcac cgataatgtg<br>atgaagcacc tgctgtctcc cctgtttcag aggtctagcc tgggagcaag gtacaccgga<br>tgcagagtga tcgccctgag gtccgtgaag aacggagcag agacacgtg ggacctgctg<br>tgcacatatc tgcagcctct gagcggacca ggcctgccca tcaagcaggt gttccacgag<br>ctgtcccagc agaccacagg aatcacaagg ctgggacctt actccctgga caaggattct<br>ctgtacctga acggctataa tgagccaggc tggacgagc ccctaccac accaaagccc<br>gccaccacat ttctccaccc cctgagcgag gcaaccaacg caatgggata ccacctgaag<br>accctgacac tgaacttcac catcagcaat ctgcagtatt ccccgatat gggcaagggc<br>tctgccacct taacagcac agagggcgtg ctgcagcacc tgctgcggcc tctgttccag<br>aagtcctcta tgggcccctt ctacctggga tgccagctga tctccctgcg gcccgaaaag<br>gatggagcag caaccggagt ggataccaca tgtacatacc ccctgacccc agtgggacca |

TABLE 27-continued

Synthetic consensus MUC16 IRC DNA Coding Sequence

| SEQ ID NO. | SEQUENCE |
|---|---|
| | ggcctggata tccagcaatt atattgggaa ctgagtcagc tgacccacgg cgtgacacag ctgggcttct atgtgctgga cagggatagc ctgtttatca acggctacgc cccacagaat ctgtccatcc gcggcgagta tcagatcaac ttccacatcg tgaactggaa tctgagcaat cccgacccta ccagctccga gtacatcgcc ctgctgaggg acatccagga taaggtgacc acactgtata agggctccca gctgcacgac accttccgct tttgcctggt gaccaacctg acaatggatt ctatgctggt gacagtgaag gccctgttct ctagcaacct ggaccccagc ctggtggagc aggtgtttct ggataagacc ctgaatgcct cctctcactg gctgggcagc acctaccagc tggtggacat ccagtgaca gagatggagc catccgtgta tcagcccacc agctcctcta gcacacagca cttctacctg aactttacca taactaatct gccctatagc caggatatcg cccagcctgg caccacaaac taccagcgga caagagaaa tatcgaggac gccctgaacc agctgttccg gaattcctct atcaagtctt atttcagcga ttgccaggtg tccaccttta gatctgtgcc aaatagccac cacacaggcg tggactccc gtgcgccttt tctcccctgg caaggagggt ggataggtg gcaatctacg aggagttcct gaggatgacc cgcgccggaa cacagctgca ggcctttacc ctggaccgga gctccgtgct ggtggatggc tattccccta acagaaatga gccactgaca ggcaactctg acctgccctt ctgggccatc atcctgatct gtctggcagg cctgctgggc ctgatcacct gcctgatctg tggctttctg gtgtgataa |

TABLE 28

Synthetic consensus MUC16 IRC Protein Sequence

| SEQ ID NO. | SEQUENCE |
|---|---|
| 8 | MDWTWILFLVAAATRVHSTAAGPLLVPFTLNFTITNLQYEEDMHHPGSRKFNTTERVL QGLLGPMFKNTSVGLLYSGCRLTLLRSEKDGAATGVDAICTHRLDPKSPGLDREQLY WELSQLTNGIKELGPYTLDRNSLYVNGFTHRSSVPNTSTPGTSTVDLGTSGTPSSLPSPT AAGPLLVPFTLNFTITNLQYEEDMRHPGSRKFNTTERVLQGLLKPLFKNTSVGPLYSGC RLTLLRPEKDGAATGVDAICTHRLDPKSPGLNREQLYWELSKLTNGITELGPYTLDRN SLYVNGFTHRTSVPTTSTPGTSTVDLGTSGTPFSLPSPTTAGPLLVPFTLNFTITNLQYEE DMHRPGSRKFNTTERVLQGLLSPIFKNSSVGPLYSGCRLTSLRPEKDGAATGMDAVCL YHPNPKRPGLDREQLYWELSQLTHNITELGPYSLDRDSLYVNGFTHQNSVPTTSTPGTS TVYWATTGTPSSFPGHTAPGPLLIPFTLNFTITNLHYEENMQHPGSRKFNTTERVLQGL LKPLFKNTSVGPLYSGCRLTLLRPEKHGAATGVDAICTHRLDPKGPGLDRERLYWELS QLTNSITELGPYTLDRDSLYVNGFNPRSSVPTTSTPGTSTVHLATSGTPSSLPGHRGRKR RSAASHLLILFTLNFTITNLRYEENMWPGSRKFNTTERVLQGLLRPLFKNTSVGPLYSG SRLTLLRPEKDGEATGVDAICTHRPDPTGPGLDREQLYLELSQLTHSITELGPYTLDRD SLYVNGFTHRSSVPTTSTGVVSEEPFTLNFTINNLRYMADMGQPGSLKFNITDNVMKH LLSPLFQRSSLGARYTGCRVIALRSVKNGAETRVDLLCTYLQPLSGPGLPIKQVFHELS QQTHGITRLGPYSLDKDSLYLNGYNEPGLDEPPTTPKPATTFLPPLSEATTAMGYHLKT LTLNFTISNLQYSPDMGKGSATFNSTEGVLQHLLRPLFQKSSMGPFYLGCQLISLRPEK DGAATGVDTTCTYHPDPVGPGLDIQQLYWELSQLTHGVTQLGFYVLDRDSLFINGYA PQNLSIRGEYQINFHIVNWNLSNPDPTSSEYIALLRDIQDKVTTLYKGSQLHDTFRFCLV TNLTMDSMLVTVKALFSSNLDPSLVEQVFLDKTLNASSHWLGSTYQLVDIHVTEMEPS VYQPTSSSSTQHFYLNFTITNLPYSQDIAQPGTTNYQRNKRNIEDALNQLFRNSSIKSYF SDCQVSTFRSVPNSHHTGVDSLCAFSPLARRVDRVAIYEEFLRMTRAGTQLQAFTLDR SSVLVDGYSPNRNEPLTGNSDLPFWAIILICLAGLLGLITCLICGFLV |

What is claimed is:

1. A nucleic acid molecule comprising one or more nucleic acid sequences selected from the group consisting of:
   (a) a nucleic acid sequence that encodes amino acids 19-1490 of SEQ ID NO: 2;
   (b) a nucleic acid sequence that encodes a protein that is at least 95% identical to amino acids 19-1490 of SEQ ID NO: 2, wherein the protein comprises at least one repeat micro-consensus (RMC) of RMC1-RMC4 of SEQ ID NO: 2;
   (c) a nucleic acid sequence that encodes SEQ ID NO: 2;
   (d) a nucleic acid sequence that encodes a protein that is at least 95% identical to SEQ ID NO: 2, wherein the protein comprises at least one RMC of RMC1-RMC4 of SEQ ID NO: 2;
   (e) a nucleic acid sequence that encodes amino acids 19-642 of SEQ ID NO: 4;
   (f) a nucleic acid sequence that encodes a protein that is at least 95% identical to amino acids 19-642 of SEQ ID NO: 4, wherein the protein comprises at least one RMC of RMC1-RMC4 of SEQ ID NO: 4;
   (g) a nucleic acid sequence that encodes SEQ ID NO: 4;
   (h) a nucleic acid sequence that encodes a protein that is at least 95% identical to SEQ ID NO: 4, wherein the protein comprises at least one RMC of RMC1-RMC4 of SEQ ID NO: 4;
   (i) a nucleic acid sequence that encodes amino acids 19-710 of SEQ ID NO: 6;
   (j) a nucleic acid sequence that encodes a protein that is at least 95% identical to amino acids 19-710 of SEQ ID NO: 6, wherein the protein comprises an alanine at amino acid position 628, an alanine at amino acid position 651, and an alanine at amino acid position 657 relative to SEQ ID NO: 6;
   (k) a nucleic acid sequence that encodes SEQ ID NO: 6; and
   (l) a nucleic acid sequence that encodes a protein that is at least 95% identical to SEQ ID NO: 6, wherein the protein comprises an alanine at amino acid position 628, an alanine at amino acid position 651, and an alanine at amino acid position 657 relative to SEQ ID NO: 6.

2. A nucleic acid molecule comprising one or more nucleic acid sequences selected from the group consisting of:
   (a) nucleotides 55-4470 of SEQ ID NO: 1;
   (b) a fragment that is at least 95% identical to nucleotides 55-4470 of SEQ ID NO: 1, wherein the fragment encodes at least one RMC of RMC1-RMC4 of SEQ ID NO: 2;
   (c) SEQ ID NO: 1;
   (d) a fragment that is at least 95% identical to SEQ ID NO: 1, wherein the fragment encodes at least one RMC of RMC1-RMC4 of SEQ ID NO: 2;
   (e) nucleotides 55-1926 of SEQ ID NO: 3;
   (f) a fragment that is at least 95% identical to nucleotides 55-1926 of SEQ ID NO: 3, wherein the fragment encodes at least one RMC of RMC1-RMC4 of SEQ ID NO: 4;
   (g) SEQ ID NO: 3;
   (h) a fragment that is at least 95% identical to SEQ ID NO: 3, wherein the fragment encodes at least one RMC of RMC1-RMC4 of SEQ ID NO: 4;
   (i) nucleotides 55-2130 of SEQ ID NO: 5;
   (j) a fragment that is at least 95% identical to nucleotides 55-2130 of SEQ ID NO: 5, wherein the fragment encodes an alanine at amino acid position 628, an alanine at amino acid position 651, and an alanine at amino acid position 657 relative to SEQ ID NO: 6;
   (k) SEQ ID NO: 5; and
   (l) a fragment that is at least 95% identical to SEQ ID NO: 5, wherein the fragment encodes an alanine at amino acid position 628, an alanine at amino acid position 651, and an alanine at amino acid position 657 relative to SEQ ID NO: 6.

3. A vector comprising the nucleic acid molecule of claim 1.

4. A vector comprising the nucleic acid molecule of claim 2.

5. The vector of claim 3, wherein the nucleic acid molecule is operably linked to a regulatory element selected from a promoter and a poly-adenylation signal.

6. The vector of claim 5, wherein the promoter is a human cytomegalovirus immediate-early promoter (hCMV promoter).

7. The vector of claim 5, wherein the poly-adenylation signal is a bovine growth hormone poly-adenylation signal (bGH polyA).

8. The vector of claim 3, wherein the vector is a plasmid or a viral vector.

9. A composition comprising one or more nucleic acid molecules as set forth in claim 1.

10. The composition according to claim 9 further comprising a pharmaceutically acceptable carrier.

11. A vaccine comprising the nucleic acid molecule of claim 2.

12. A vaccine comprising the nucleic acid molecule of claim 1.

13. The vaccine of claim 11, wherein the nucleic acid molecule comprises an expression vector.

14. The vaccine of claim 11, further comprising a pharmaceutically acceptable excipient.

15. The vaccine of claim 11, further comprising an adjuvant.

16. The vaccine of claim 15, wherein the adjuvant is IL-12, IL-15, IL-28, or RANTES.

* * * * *